United States Patent
Hoemann et al.

(10) Patent No.: US 11,844,874 B2
(45) Date of Patent: Dec. 19, 2023

(54) LYOPHILIZED POLYMER SCAFFOLD COMPOSITIONS, PROCESSES FOR PREPARATION AND USE IN ANABOLIC WOUND REPAIR

(71) Applicant: ORTHO REGENERATIVE TECHNOLOGIES INC., Kirkland (CA)

(72) Inventors: Caroline Hoemann, Montreal (CA); Daniel Veilleux, Montreal (CA); Michael D. Buschmann, Montreal (CA)

(73) Assignee: ORTHO REGENERATIVE TECHNOLOGIES INC., Kirkland (CA)

( * ) Notice: Subject to any disclaimer, the term of this patent is extended or adjusted under 35 U.S.C. 154(b) by 0 days.

(21) Appl. No.: 15/119,748

(22) PCT Filed: Feb. 20, 2015

(86) PCT No.: PCT/CA2015/050130
§ 371 (c)(1),
(2) Date: Aug. 18, 2016

(87) PCT Pub. No.: WO2015/123779
PCT Pub. Date: Aug. 27, 2015

(65) Prior Publication Data
US 2017/0056550 A1    Mar. 2, 2017

Related U.S. Application Data

(60) Provisional application No. 61/942,547, filed on Feb. 20, 2014.

(51) Int. Cl.
*A61L 27/50* (2006.01)
*A61L 27/20* (2006.01)
(Continued)

(52) U.S. Cl.
CPC .......... *A61L 27/20* (2013.01); *A61K 9/0024* (2013.01); *A61K 9/19* (2013.01); *A61K 31/721* (2013.01);
(Continued)

(58) Field of Classification Search
CPC ........ A61K 35/16; A61K 9/19; A61K 31/721; A61K 31/722; A61K 38/1866;
(Continued)

(56) References Cited

U.S. PATENT DOCUMENTS

| 2007/0021703 A1 | 1/2007 | McCarthy | |
| 2007/0116768 A1* | 5/2007 | Chorny | C08L 5/02 424/489 |

(Continued)

FOREIGN PATENT DOCUMENTS

| CA | 2386586 A1 | 4/2001 |
| CA | 2672936 A1 | 6/2008 |

(Continued)

OTHER PUBLICATIONS

Wang et al. Protonation constants of chitosan with different molecular weight and degree of deacetylation. Carbohydrate Polymers(2006), v65, p. 194-201. (Year: 2006).*

(Continued)

*Primary Examiner* — Sean C. Barron
(74) *Attorney, Agent, or Firm* — Eric L. Lane; Green Patent Law

(57) ABSTRACT

The present application relates to a lyophilized scaffold composition having at least one polysaccharide wherein said scaffold is substantially solid and capable of being formed into a desired shape; wherein the at least one polysaccharide has a protonation level resulting in controlled rehydration of said scaffold, such that when said scaffold is contacted with at least one of a neutral aqueous solution, blood, blood (Continued)

derived fluid and combinations thereof, said scaffold forms a microparticle dispersion and stimulates tissue remodeling and anabolic wound repair, a process for preparing a lyophilized scaffold composition and the use of a lyophilized scaffold composition for wound repair in a mammal.

20 Claims, 37 Drawing Sheets

(51) Int. Cl.
  *A61L 27/02*    (2006.01)
  *A61L 27/54*    (2006.01)
  *A61K 31/722*    (2006.01)
  *C08L 5/08*    (2006.01)
  *A61K 31/721*    (2006.01)
  *C08L 5/02*    (2006.01)
  *C08B 37/08*    (2006.01)
  *C08B 37/02*    (2006.01)
  *A61L 27/56*    (2006.01)
  *A61K 35/16*    (2015.01)
  *A61K 8/37*    (2006.01)
  *A61K 38/20*    (2006.01)
  *A61K 38/18*    (2006.01)
  *A61K 38/21*    (2006.01)
  *A61K 38/48*    (2006.01)
  *A61K 38/19*    (2006.01)
  *A61K 9/19*    (2006.01)
  *A61K 9/00*    (2006.01)
  *A61K 38/37*    (2006.01)

(52) U.S. Cl.
  CPC ............ *A61K 31/722* (2013.01); *A61K 35/16* (2013.01); *A61K 38/1866* (2013.01); *A61K 38/193* (2013.01); *A61K 38/195* (2013.01); *A61K 38/20* (2013.01); *A61K 38/21* (2013.01); *A61K 38/37* (2013.01); *A61K 38/482* (2013.01); *A61K 38/4833* (2013.01); *A61L 27/025* (2013.01); *A61L 27/50* (2013.01); *A61L 27/54* (2013.01); *A61L 27/56* (2013.01); *C08B 37/003* (2013.01); *C08B 37/0021* (2013.01); *C08L 5/02* (2013.01); *C08L 5/08* (2013.01); *C12Y 304/21005* (2013.01); *C12Y 304/21059* (2013.01); *A61L 2300/252* (2013.01); *A61L 2300/412* (2013.01); *A61L 2430/06* (2013.01)

(58) Field of Classification Search
  CPC .... A61K 38/193; A61K 38/195; A61K 38/20; A61K 38/21; A61K 38/37; A61K 38/482; A61K 38/4833; A61K 9/0024; C08L 5/02; C08L 5/08; C08B 37/0021; C08B 37/003; C12Y 304/21005; C12Y 304/21059; A61L 27/20; A61L 27/025; A61L 27/54; A61L 27/56; A61L 27/50; A61L 2300/252; A61L 2300/412; A61L 2430/06
See application file for complete search history.

(56) References Cited

U.S. PATENT DOCUMENTS

| | | | |
|---|---|---|---|
| 2009/0004230 A1 | 1/2009 | Chuetz et al. | |
| 2010/0272669 A1 | 10/2010 | Malessa et al. | |
| 2012/0100185 A1* | 4/2012 | Wen | A61P 43/00 424/400 |

FOREIGN PATENT DOCUMENTS

| | | |
|---|---|---|
| CA | 2814783 A1 | 5/2011 |
| CA | 2814784 A1 | 5/2011 |
| JP | 2010-254688 | 11/2010 |
| WO | WO 2007/111416 A1 | 10/2007 |

OTHER PUBLICATIONS

Evans. "pKa's of Inorganic and Oxo-Acids", retrieved from http://evans.rc.fas.harvard.edu/pdf/evans_pKa_table.pdf. (Year: 2005).*
Yamada et al. Chitosan Oligomers as Potential and Safe Absorption Enhancers for Improving the Pulmonary Absorption of Interferon-a in Rats. J Pharm Sci 94:2432-2440, 2005. (Year: 2005).*
Sleijfer et al. Side effects of interferon-(alpha) therapy. Pharm World Sci (2005) 27: 423-431. (Year: 2005).*
De La Riva et al. VEGF-controlled release within a bone defect from alginate/chitosan/PLA-H scaffolds. European Journal of Pharmaceutics and Biopharmaceutics 73 (2009) 50-58. (Year: 2009).*
IUPAC. Definition of "Oligomeric Molecule" Compendium of Chemical Terminology, 2nd ed. (the "Gold Book"). Compiled by A. D. McNaught and A. Wilkinson. Blackwell Scientific Publications, Oxford (1997). (Year: 1997).*
Chu et al. Therapeutic angiogenesis: controlled delivery of angiogenic factors. Ther. Deliv. (2012), 3(6), 34 page reprint. (Year: 2012).*
Ko et al. Preparation and characterization of chitosan microparticles intended for controlled drug delivery. Preparation and characterization of chitosan microparticles intended for controlled drug delivery. International Journal of Pharmaceutics (2002), 249, 165-174 (Year: 2002).*
Liang et al. Development of dextran microparticles loaded with IL-1Ra of high-encapsulation efficiency and high-bioactivity by a novel method without exposing IL-1Ra to water-oil interfaces. Powder Technology (2013), 235, 299-302. (Year: 2013).*
Reves et al. Lyophilization to Improve Drug Delivery For Chitosan-Calcium Phosphate Bone Scaffold Construct: A Preliminary Investigation. J Biomed Mater Res Part B: Appl Biomater 90B: 1-10, 2009. (Year: 2009).*
Chua et al. Chitosan Microparticles and Nanoparticles as Biocompatible Delivery Vehicles for Peptide and Protein-Based Immunocontraceptive Vaccines. Mol. Pharmaceutics 2012, 9, 81-90. (Year: 2012).*
Cruz et al. Chitosan microparticles as injectable scaffolds for tissue engineering. J Tissue Eng Regen Med 2008; 2: 378-380. (Year: 2008).*
Nicolete et al. Leukotriene B4-loaded microspheres: a new therapeutic strategy to modulate cell activation. BMC Immunology (2008), 9(36), 11 pages. (Year: 2008).*
Nah et al. Spectroscopic Characterization and Preparation of Low Molecular, Water-Soluble Chitosan with Free-Amine Group by Novel Method. J Polym Sci Part A: Polym Chem (2002), 40: 3796-3803. (Year: 2002).*
Thein-Han et al. Biomimetic chitosan-nanohydroxyapatite composite scaffolds for bone tissue engineering. Acta Biomaterialia (2009), 5, 1182-1197. (Year: 2009).*
Qin et al. Water-solubility of chitosan and its antimicrobial activity. Carbohydrate Polymers (2006), 63, 367-374. (Year: 2006).*
D. Maurer The Significance of pH Stability for Cell Cultures. Internet Article, 2002, 2 pages. (Year: 2002).*
Technical Note T11-011. pH of Distilled Water. Bibby Scientific, 2011, 1 page. (Year: 2011).*
C. Higgins An introduction to acid-base balance in health and disease. Internet Article, 2004, 16 pages. (Year: 2004).*
English Translation of Office Action dated Oct. 2, 2018 in related Japanese Patent Application No. 2016-553410.
Patois, E. et al. "Novel thermosensitive chitosan hydrogels: in vivo evaluation" J. Biomed. Mater. Res. A Nov. 2009, vol. 91 (No. 2), pp. 324-330.
International Search Report and Written Opinion dated Jun. 15, 2015 in related International Application No. PCT/CA2015/050130.
Database WPI Week 201371, Thomson Scientific, AN 2013-N96850 XP002771144 & CN 103028135A (Wuhan Aolvxin Bio Tech Co) Apr. 10, 2013.

(56) References Cited

OTHER PUBLICATIONS

Database WPI Week 200727, Thomson Scientific, AN 2007-277911 XP002771145 & KR 20050104704 A (Hyusung Corp) Nov. 3, 2005.
Croisier, Florence et al. "Chitosan-based biomaterials for tissue engineering," European Polymer J. vol. 49, No. 4, Jan. 23, 2013.
Extended European Search Report dated Jul. 10, 2017 in related European Patent Application No. 15752604.7.

* cited by examiner

LEGEND
R = clotting time
K = time it takes for amplitude to increase from 2 to 20 mm.
α = angle (rate of clot formation, degrees)
MA = maximal amplitude (maximal clot tensile strength, mm)

Slow in situ rehydration of a freeze-dried chitosan-HCl scaffold (Formulation 5, arrow, 10 kDa, 10 mg/mL, no lyoprotectant) to one of two bleeding microdrill holes 3 week granulation tissue implant-treated (formulations #4 and #5: 10 kDa chitosan-HCl, 5 or 10 mg/mL, 80% protonation)

Arginase-1+ macrophages

RAM-11+ macrophages

3 week granulation tissue implant-treated (formulations #4 and #5 )

Angiogenic blood vessels Gomori Trichrome

Safranin O-Fast green

3 week granulation tissue implant-treated (formulations #6 and #7 )

→ Angiogenic blood vessels
Gomori Trichrome

G) Formulation #7
Dextran-S only

H) Formulation #6
Dextran-S/chitosan

Formulation #4 (C5*) & #5 (C10*)

A) Freeze-dried implants inside petri dishes

Formulation #34　　#33　　#29
20 mg/mL　　10 mg/mL　　5 mg/mL

B) In vivo treated sheep defect -- Implant delivered to bleeding microdrill hole Formulation #33

C) In vivo sheep untreated bleeding microdrill defects

E) Sheep defect at day 1 post-operative

F) In vivo sheep defect freeze-dried chitosan 1 day residency shown by rhodamine-chitosan tracer

G) In vivo sheep defect freeze-dried chitosan 1 day residency shown by rhodamine-chitosan tracer in 3 microdrill holes (10 mg/mL, arrows)

H) in vivo implant appearance: in situ rehydration in microdrill hole (5 mg/mL)

B) Micro-CT measures of non-mineralized drill hole area over time at 0 to −1.5 mm below the cartilage defect surface

9 MONTH REPAIR TISSUES

CONTROL – Left knee

Legend
△ Exposed mineral indicating area of failed resurfacing

╲ plane of histology section

← resurfaced microdrill hole

TREATED – Right knee

9 MONTH REPAIR TISSUES
Safranin O-Fast Green

CONTROL – Left knee

TREATED – Right knee, microdrill holes treated with formulation #33

Legend

▷ Exposed mineral indicating area of failed resurfacing

↘ edge of cartilage defect

1, 2, 3 resurfaced microdrill holes

NC: native cartilage

SC: subchondral callus

**9 MONTH REPAIR TISSUES
Safranin O-Fast Green**

▷ Exposed mineral indicating area of failed resurfacing

CONTROL – Left knee

TREATED – Right knee

9 MONTH REPAIR TISSUES
Safranin O-Fast Green
Hyaline-like repair tissue

CONTROL – Left knee

TREATED – Right knee

LYOPHILIZED POLYMER SCAFFOLD COMPOSITIONS, PROCESSES FOR PREPARATION AND USE IN ANABOLIC WOUND REPAIR

FIELD

This disclosure relates to freeze-dried polymer compositions for use in implantation in bleeding subchondral bone defects and/or bleeding meniscal trephination channels and/or and/or bleeding tendon insertion sites and/or bleeding rotator cuff repair sites, i) promoting residency of the coagulum and ii) stimulating therapeutic effects on bone marrow-derived articular cartilage repair and meniscal repair.

BACKGROUND

Trauma or repetitive damage to the articular cartilage layer may lead to degeneration of the non-calcified tissue and the development of a symptomatic focal cartilage lesion. To prevent or delay meniscal damage and global knee degeneration, Outerbridge Grade III and IV lesions that approach or violate the osteochondral junction are often treated by surgical cartilage repair therapy. Cartilage repair therapies begin with a debridement step, where all degenerated articular cartilage is removed from the lesion area with a curette or shaver, to expose the subchondral bone underlying the lesion. In cell-assisted therapies, the debrided lesion is then treated by applying autologous cells using a biomaterial scaffold or tissue flap to retain the cells in the lesion. By another approach, bone marrow stimulation therapies such as microfracture, involve the creation of bone holes ~2 mm in diameter and 2 to 4 mm deep in the base of the debrided cartilage defect (Steadman J R, Rodkey W G, Singleton S B, Briggs K K: Microfracture technique for full-thickness chondral defects: technique and clinical results, Operative Techniques in Orthopaedics 1997, 7:300-304; Mithoefer K, Williams R J, 3rd, Warren R F, Potter H G, Spock C R, Jones E C, Wickiewicz T L, Marx R G: The microfracture technique for the treatment of articular cartilage lesions in the knee. A prospective cohort study, J Bone Joint Surg-Am Vol 2005, 87:1911-1920) to stimulate repair tissue formation by cells that migrate from the trabecular bone marrow into the cartilage lesion. However it has been reported that the repair tissues elicited by cell-assisted or microfracture therapies are most frequently fibrous tissue or fibrocartilage (Knutsen G, Engebretsen L, Ludvigsen T C, Drogset J O, Grontvedt T, Solheim E, Strand T, Roberts S, Isaksen V, Johansen C: Autologous chondrocyte implantation compared with microfracture in the knee—A randomized trial, J Bone Joint Surg-Am Vol 2004, 86A:455-464; Saris D B, Vanlauwe J, Victor J, Haspl M, Bohnsack M, Fortems Y, Vandekerckhove B, Almqvist K, et al: Characterized chondrocyte implantation results in better structural repair when treating symptomatic cartilage defects of the knee in a randomized controlled trial versus microfracture, Am J Sports Med 2008, 36:235-246), tissues with weak biomechanical properties and limited durability compared to hyaline articular cartilage. In two distinct randomized controlled clinical trials with 40 patients per treatment group, the clinical benefit of cell therapy was not superior to microfracture at 5 years post-surgery (Knutsen G, Engebretsen L, Ludvigsen T C, Drogset J O, Grontvedt T, Solheim E, Strand T, Roberts S, Isaksen V, Johansen C: Autologous chondrocyte implantation compared with microfracture in the knee—A randomized trial, J Bone Joint Surg-Am Vol 2004, 86A:455-464; Saris D B, Vanlauwe J, Victor J, Haspl M, Bohnsack M, Fortems Y, Vandekerckhove B, Almqvist K, et al.: Characterized chondrocyte implantation results in better structural repair when treating symptomatic cartilage defects of the knee in a randomized controlled trial versus microfracture, Am J Sports Med 2008, 36:235-246; Knutsen G, Drogset J O, Engebretsen L, Grontvedt T, Isaksen V, Ludvigsen T C, Roberts S, Solheim E, Strand T, Johansen O: A Randomized trial comparing autologous chondrocyte implantation with microfracture, J Bone Joint Surg-Am Vol 2007, 89A:2105-2112; Vanlauwe J, Saris D B F, Victor J, Almqvist K F, Bellemans J, Luyten F P, for the TA, Group EXTS: Five-Year Outcome of Characterized Chondrocyte Implantation Versus Microfracture for Symptomatic Cartilage Defects of the Knee: Early Treatment Matters, The American Journal of Sports Medicine 2011, 39 2566-2574). Microfracture, otherwise known as "bone marrow stimulation" therapy, offers a less expensive alternative to cell therapy in treating focal cartilage lesions, with a similar probability of a therapeutic response. It is known that skeletally aged knees have an attenuated cartilage repair response to marrow stimulation (Kreuz P C, Erggelet C, Steinwachs M R, Krause S J, Lahm A, Niemeyer P, Ghanem N, Uhl M, Sudkamp N: Microfracture of chondral defects in the knee associated with different results in patients aged 40 years or younger?, Arthroscopy-the Journal of Arthroscopic and Related Surgery 2006, 22:1180-1186). Adjunct treatments that improve the quality and durability of bone marrow-elicited repair tissue are therefore desired, especially for chronic lesions with evidence of subchondral bone sclerosis (Hoemann C D, Gosselin Y, Chen H, Sun J, Hurtig M, Carli A, Stanish W D: Characterization of initial microfracture defects in human condyles, Journal of Knee Surgery 2013; 26(5):347-55).

Liquid chitosan formulations have been developed that successfully stimulate a more hyaline articular cartilage repair in animal microfracture defects (Hoemann C D, Hurtig M, Rossomacha E, Sun J, Chevrier A, Shive M S, Buschmann M D: Chitosan-glycerol phosphate/blood implants improve hyaline cartilage repair in ovine microfracture defects, J Bone Joint Surg-Am Vol 2005, 87A:2671-2686) and generate increased repair tissue fill at 1 year post-operative in human compared to microfracture-alone (Stanish W D, McCormack R, Forriol C F, Mohtadi N, Pelet S, Desnoyers J, Restrepo A, Shive M S: Novel scaffold-based BST-CarGel® treatment results in superior cartilage repair in a randomized controlled trial compared to microfracture. Better structural repair at 12 months in terms of repair tissue quantity and quality. J. Bone Joint Surg-Am Vol 2013, 95(18):1640-50) however current formulations and methods are limited by several practical considerations.

In one application, a chitosan solution was prepared with biodegradable medium-viscosity chitosan with 75% to 85% degree of deacetylation (DDA) and disodium glycerol phosphate. The chitosan solution was then mixed at a 1:3 v/v ratio with autologous whole blood and flooded over a cartilage lesion treated by bone marrow stimulation (Hoemann C D, Hurtig M, Rossomacha E, Sun J, Chevrier A, Shive M S, Buschmann M D: Chitosan-glycerol phosphate/blood implants improve hyaline cartilage repair in ovine microfracture defects, J Bone Joint Surg-Am Vol 2005, 87A:2671-2686). The implant solidified in situ through blood coagulation, fibrin polymerization, and by the transitioning of chitosan from soluble chains at pH 6, to microparticles at blood pH 7, during which chitosan chains form complexes with anionic blood proteins such as complement C3 (Marchand C, Rivard G E, Sun J, Hoemann C D:

Solidification mechanisms of chitosan-glycerol phosphate/blood implant for articular cartilage repair, Osteoarthritis Cartilage 2009, 17:953-960; Marchand C, Bachand J, Perinet J, Baraghis E, Lamarre M, Rivard G E, De Crescenzo G, Hoemann C D: C3, C5, and factor B bind to chitosan without complement activation, Journal of Biomedical Materials Research Part A 2010, 93A:1429-1441). The in situ-solidified chitosan-blood implant transiently concentrates neutrophils, macrophages, alternatively activated arginase-1+ macrophages and osteoclasts near the top of the subchondral bone defect, which stimulates angiogenesis, bone remodeling, mesenchymal stromal cell migration towards the cartilage lesion, and formation of cartilage-regenerating chondrogenic foci near the articular surface (Hoemann C D, Chen G P, Marchand C, Sun J, Tran-Khanh N, Chevrier A, Thibault M, Fernandes M G J, et al. Scaffold-guided subchondral bone repair: implication of neutrophils and alternatively activated arginase-1+ macrophages. Am. J. Sports Med. 2010; 38(9): 1845-56; Chen G, Sun J, Lascau-Coman V, Chevrier A, Marchand C, Hoemann C D. Acute osteoclast activity following subchondral drilling is promoted by chitosan and associated with improved cartilage repair tissue integration. Cartilage, 2011: 2: 173-185; Chevrier A, Hoemann C D, Sun J, Buschmann M D. Chitosan-glycerol phosphate/blood implants increase cell recruitment, transient vascularization and subchondral bone remodeling in drilled cartilage defects. Osteoarthritis & Cartilage 2007 15:316-327). In human subjects, the liquid chitosan/blood mixture was prepared ex vivo, with a phlebotomy, then injected as a liquid mixture over the microfracture cartilage lesion through a mini-arthrotomy along with a 15 minute wait-time for in situ solidification (WO200200272-A, WO2011060553-A1; Shive M S, Hoemann C D, Restrepo A, Hurtig M B, Duval N, Ranger P, Stanish W, Buschmann M D: BST-CarGel: In Situ ChondroInduction for Cartilage Repair, Operative Techniques in Orthopaedics 2006, 16:271-278). During the wait time for in situ solidification, the cartilage was exposed to the air. Creation of an implant with the same therapeutic responses that does not require a phlebotomy, ex vivo manipulation and a 15 minute wait time during the arthrotomy for in situ solidification would be very advantageous.

In other prior art, liquid chitosan formulations were mixed with autologous whole blood and pre-solidified to form an elastic cylindrical blood clot implant containing highly dispersed chitosan microparticles (Hoemann C, Sun J, Hurtig M, Guzman-Morales J, Hubert-Lafantaisie C: Presolidified composition for use in repairing tissue of a patient, comprises a blood component, a salt and a polymer, the blood component, salt and polymer being mixed and solidified in a recipient before administration to the patient, WO2011060554-A1). The hybrid implant can be prepared in advance of the arthrotomy step, and therefore reduces arthrotomy time, and allows treatment of defects that are not horizontally positioned (WO2011060554-A1). In a rabbit osteochondral repair model, chitosan formulations with low molecular weight (10 kDa, 40 kDa) were shown to stimulate therapeutic osteochondral wound repair responses during 3 weeks post-operative in skeletally aged rabbits (Lafantaisie-Favreau C H, Guzman-Morales J, Sun J, Chen G P, Harris A, Smith T D, Carli A, Henderson J, Stanish W D, Hoemann C D: Subchondral pre-solidified chitosan/blood implants elicit reproducible early osteochondral wound-repair responses including neutrophil and stromal cell chemotaxis, bone resorption and repair, enhanced repair tissue integration and delayed matrix deposition, BMC Musculoskeletal Disorders 2013, 14:27), including chemotaxis of neutrophils, mesenchymal stromal cells and osteoclasts, inhibition of rapid fibrocartilage formation, and bone remodeling. However chitosan clearance kinetics can also influence repair because, in the rabbit, where high metabolism drives rapid wound repair, the 150 kDa chitosan formulation was cleared too slowly, leading to excessive apoptotic neutrophil accumulation and greater bone resorption, which is an undesired effect. Implantation of a pre-solidified implant created from an aqueous solution of 10 kDa chitosan dispersed in whole blood stimulated more bone remodeling and a more hyaline-like cartilage repair compared to drilling alone, at 70 days after press-fitting into rabbit osteochondral defects (Guzman-Morales J, Lafantaisie-Favreau C H, Chen G, Hoemann C D: Subchondral chitosan/blood implant-guided bone plate resorption and woven bone repair is coupled to hyaline cartilage regeneration from microdrill holes in aged rabbit knees, Osteoarthritis and Cartilage 2014, 22:323). It is known how to create a blood clot containing dispersed chitosan microparticles by combining liquid chitosan solution and blood. However knowledge of how to create a blood clot containing dispersed chitosan microparticles directly from a freeze-dried chitosan formulation is currently lacking.

Implants consisting of chitosan microparticles in blood coagulum are known to elicit neutrophils and alternatively activated macrophages to other sites including subcutaneous implants (Hoemann C D, Chen G, Marchand C, Sun J, Tran-Khanh N, Chevrier A, Thibault M, Fernandes M G J, Poubelle P E, Shive M S, Centola M, El-Gabalawy H: Scaffold-guided subchondral bone repair: implication of neutrophils and alternatively activated arginase-1+ macrophages, Am J Sports Med 2010, 38:1845-1856). Therefore implants generated from freeze-dried chitosan scaffolds that disperse as microparticles in blood or blood-derived fluids may be used to stimulate the revascularization and repair of other joint tissues including the meniscus (Chevrier A, Nelea M, Hurtig M B, Hoemann C D, Buschmann M D: Meniscus Structure in Human, Sheep, and Rabbit for Animal Models of Meniscus Repair, Journal of Orthopaedic Research 2009, 27:1197-1203).

Liquid chitosan formulations, according to the solution pH and osmolality, will precipitate, gel, or undergo spontaneous hydrolysis over time at room temperature (WO2011060553-A1). Low molecular mass chitosan solutions that form spontaneously by long-term storage of liquid chitosan can still be used to prepare a liquid chitosan-blood implant but lack in ease-of-use for in situ solidification of the resulting aqueous mixture, because a liquid low-viscosity polymer-blood mixture is difficult to retain in a cartilage defect, and because joint contours are curved. Given that hydrolysis alters the chitosan structure and biophysical behavior, a method for maintaining chitosan molecular weight during storage is needed. An off-the-shelf chitosan formulation that maintains polymer molecular weight during prolonged storage at room temperature, that can be used to create a hybrid polysaccharide-blood implant containing dispersed chitosan microparticles, that does not require a 15 minute wait time for implantation, has controlled mechanical properties and a specific shape (rigid with mechanical integrity, not flakes), and that can be delivered and retained in an osteochondral defect is desired. A chitosan device that avoids time-consuming intra-operative wait time for implant ex vivo preparation and does not require a 15 minute wait time for in situ solidification, that is easy to deliver to marrow stimulation defects, and that allows for long-term room temperature storage without any alteration in the chitosan molecular weight would be very advantageous.

Several lyophilized chitosan-acetic acid formulations with distinct degree of deacetylation and molecular mass were implanted into osteochondral defects in a rabbit model, and shown to have detrimental effects on bone and cartilage repair (Abarrategi A, Lopiz-Morales Y, Ramos V, Civantos A, Lopez-Duran L, Marco F, Lopez-Lacomba J L: Chitosan scaffolds for osteochondral tissue regeneration, Journal of Biomedical Materials Research Part A 2010, 95A:1132-1141). In the study by Abarrategi et al 2010, defects were created in the medial femoral condyle of N=3 rabbits with 3.0 to 3.4 kg body mass, which is skeletally immature according to data published by Masoud et al 1986 (Masoud I, Shapiro F, Kent R, Moses A: A longitudinal study of the growth of the New Zealand white rabbit: Cumulative and biweekly incremental growth rates for body length, body weight, femoral length, and tibial length, Journal of Orthopaedic Research 1986, 4:221-231). Treatment of an osteochondral rabbit defect with chitosan-acetic acid lyophilized scaffold (80% DDA-500 kDa, 90% DDA-500 kDa, 90% DDA-9 kDa) failed to improve or reduced the histological cartilage repair tissue scores compared to untreated osteochondral defects. It was reported that overall histological scores were improved in N=3 defects treated by 10 kDa chitosan 83% DDA with or without 18% w/w calcium carbonate mineral content, compared to untreated defects at 3 months post-operative (Abarrategi A, Lopiz-Morales Y, Ramos V, Civantos A, Lopez-Duran L, Marco F, Lopez-Lacomba J L: Chitosan scaffolds for osteochondral tissue regeneration, Journal of Biomedical Materials Research Part A 2010, 95A:1132-1141). However, high overall histology scores for 10 kDa 83% DDA chitosan-treated defects, were contradicted by accompanying histology images showing glycosaminoglycan-depleted extracellular matrix and poor structural integrity of the repair tissue (Abarrategi A, Lopiz-Morales Y, Ramos V, Civantos A, Lopez-Duran L, Marco F, Lopez-Lacomba J L: Chitosan scaffolds for osteochondral tissue regeneration, Journal of Biomedical Materials Research Part A 2010, 95A:1132-1141). Moreover, given the high spontaneous repair potential of immature rabbit osteochondral defects (Shapiro F, Koide S, Glimcher M J: Cell Origin and Differentiation in the Repair of Full-Thickness Defects of Articular Cartilage, J Bone Joint Surg-Am Vol 1993, 75A:532-553; Wei X C, Messner K: Maturation-dependent durability of spontaneous cartilage repair in rabbit knee joint, J Biomed Mater Res 1999, 46:539-548) and given the lack of evidence that the implants were retained in vivo in the treated defects, results of this study could be explained by failure of the implant to reside in the treated defect. Another freeze-dried chitosan scaffold has been patented for hemostatic activity, but the formulation includes a non-porous collagen phase to allow high mechanical properties that are incompatible with microparticle dispersion in a coagulum (Mehta R D: Accelerated wound healing systems and their production method. Edited by MEHTA R D (MEHT-Individual), IN200701721-I3). Another freeze-dried chitosan sponge was previously conceived but the scaffold was intended to remain a solid after implanting to allow prolonged drug delivery (Moon H, Byung J A: Porous drug delivery type functional scaffolds preparing method, involves controlling pore size by dissolving chitin/chitosan in solution of lactic and acetic acid or hydrochloric acid, and pouring solution into scaffold-forming mold. Edited by BYUNG J A (BYUN-Individual) MOON H (MOON-Individual) UNIV EULJI IND COOP (UYEU-Non-standard) WELLBEING CO LTD (WELL-Non-standard), KR2008016216-A).

Other polymer implants have been previously developed with ease-of-use for implanting in a bleeding osteochondral defect, but show inconsistent cartilage repair efficacy and frequently inhibit bone repair. Solid hydrogels, sponges, cross-linked polymers or cylinders of synthetic polyglycolic acid (PGLA)/tri-polyphosphate (TruFit®, Smith & Nephew), degrade slowly in the subchondral bone defect, inhibit subchondral bone regeneration and show inconsistent articular cartilage repair (Hoemann C D, Sun J, Legare A, McKee M D, Buschmann M D: Tissue engineering of cartilage using an injectable and adhesive chitosan-based cell-delivery vehicle, Osteoarthritis Cartilage 2005, 13:318-329; Streitparth F, Schoettle P, Schlichting K, Schell H, Fischbach F, Denecke T, Duda G N, Schroeder R J: Osteochondral Defect Repair after Implantation of Biodegradable Scaffolds: Indirect Magnetic Resonance Arthrography and Histopathologic Correlation, Acta Radiologica 2009, 50:765-774; Carmont M R, Carey-Smith R, Saithna A, Dhillon M, Thompson P, Spalding T: Delayed Incorporation of a TruFit Plug: Perseverance Is Recommended, Arthroscopy: The Journal of Arthroscopic & Related Surgery 2009, 25:810-814; Barber F A, Dockery W D: A Computed Tomography Scan Assessment of Synthetic Multiphase Polymer Scaffolds Used for Osteochondral Defect Repair, Arthroscopy-the Journal of Arthroscopic and Related Surgery 2010, 27:60-64). The TruFit PGLA scaffold that was shown to inhibit bone repair also has toxic degradation products (PGLA degrades to lactic acid and glycolic acid). In another approach, a solid membrane implant of porcine collagen type I and collagen type III (Chondro-Gide®, Geislich) was implanted over a full-thickness cartilage defect treated by microfracture, but proof-of-efficacy in eliciting cartilage repair as a cell-free scaffold is absent (Bartlett W, Skinner J A, Gooding C R, Carrington R W J, Flanagan A M, Briggs T W R, Bentley G: Autologous chondrocyte implantation versus matrix-induced autologous chondrocyte implantation for osteochondral defects of the knee, J Bone Joint Surg-Br Vol 2005, 87B:640-645). Polymers that biodegrade with a kinetics that is paralleled by granulation tissue formation are therefore desired because they have the potential to amplify natural wound repair responses, without physically interfering with cell migration into the bone lesion, and have the potential to stimulate wound repair responses that restore an osteochondral tissue with better biomechanical properties compared to implants that lead to soft tissue repair instead of mineralized bone repair of the subchondral bone plate, or large tissue voids in the subchondral bone space.

In designing an implant for augmented microfracture repair, there is a balance to strike between rigid polymers that degrade slowly and block subchondral bone regeneration, and collagen membranes that have low intrinsic wound repair bioactivity. The key property of a therapeutic implant applied to bleeding bone is chemotactic activity—the ability of the implant to attract cells, and the appropriate cell types, to the microfractured bone channels. Homogeneously dispersed chitosan microparticle in the initial blood clot, and appropriate in situ degradation kinetics by leukocytes, were shown to stimulate angiogenesis in subchondral bone defects (Mathieu C, Chevrier A, Lascau-Coman V, Rivard G E, Hoemann C D: Stereological analysis of subchondral angiogenesis induced by chitosan and coagulation factors in microdrilled articular cartilage defects, Osteoarthritis Cartilage 2013, 21:849-859) and transient resorption and repair of the subchondral bone plate (Bell A D, Lascau-Coman V, Sun J, Chen G, Lowerison M W, Hurtig M B, Hoemann C D: Bone-Induced Chondroinduction in Sheep Jamshidi Biopsy Defects with and without Treatment by Subchondral Chitosan-Blood Implant: 1-Day, 3-Week, and 3-Month Repair, Cartilage 2013, 4:131-143; Lafantaisie-Favreau C H, Guzman-Morales J, Sun J, Chen G P, Harris A, Smith T D, Carli A, Henderson J, Stanish W D, Hoemann C D: Subchondral pre-solidified chitosan/blood implants elicit reproducible early osteochondral wound-repair responses including neutrophil and stromal cell chemotaxis, bone resorption and repair, enhanced repair tissue integration and delayed matrix deposition, BMC Musculoskeletal Disorders 2013, 14; Guzman-Morales J, Lafantaisie-Favreau C H, Chen G, Hoemann C D: Subchondral chitosan/blood implant-guided bone plate resorption and woven bone repair is coupled to hyaline cartilage regeneration from microdrill holes in aged rabbit knees, Osteoarthritis and Cartilage 2014, 22:323), which can lead to chondroinduction at the base of the articular cartilage lesion and cartilage regeneration (WO2011060554-A1).

A solid polysaccharide implant formulation that can be shaped into a form that permits delivery to a bleeding defect, that reproducibly rehydrates and disperses in blood, and forms microparticles that reside in the defect, that attract macrophages and induce angiogenesis and local bone remodeling and osteochondral repair is desired.

Given the current state of the art, a chitosan implant is needed that responds to at least one of the following criteria:

a. The implant has a rigid 3-dimensional structure and maintains structural integrity in order to be formed into specific shapes (for example but not limited to cored with a biopsy punch into a cylinder, or trimmed with a scalpel, or dried in the shape of a cone or cylinder).

b. The freeze-dried chitosan scaffold rehydrates slowly enough to allow controlled physical deposition in the marrow stimulation bone defect and retention of chitosan particles in the defect.

c. The freeze-dried chitosan disperses as microparticles after the scaffold becomes imbibed with whole blood, blood plasma, serum, or other blood fractions (i.e. platelet-rich plasma, leukocyte fraction, citrated plasma), and promotes residency of the coagulum in a bone defect.

d. Freeze-dried chitosan after rehydration in blood biointerfaces with molecular species in blood and forms similar blood protein-chitosan complexes as those formed when liquid chitosan is mixed into whole blood or blood plasma (i.e., chitosan-complement C3 or chitosan-complement C5, Factor B, or prothrombin) (Marchand C, Bachand J, Perinet J, Baraghis E, Lamarre M, Rivard G E, De Crescenzo G, Hoemann C D: C3, C5, and factor B bind to chitosan without complement activation, Journal of Biomedical Materials Research Part A 2010, 93A:1429-1441; Lafantaisie-Favreau C-H, Desgagné M, Osseiran S, De Crescenzo G, Rivard G-E, Hoemann C D: Chitosan trapping of anionic coagulation factors during soluble-microparticle transition. Transactions Canadian Connective Tissue Conference, 2013, Montreal, Quebec).

e. Blood plasma after combining with the implant scaffold coagulates in situ through the extrinsic or intrinsic coagulation cascade or direct thrombin activation resulting in fibrin clot formation.

f. The implant, after introducing into subchondral bone defects, provides at least one of elicits more neutrophils, macrophages and angiogenic blood vessels than untreated defects, promotes subchondral bone plate resorption and repair, stimulates chondro-induction at the base of the cartilage lesion, leading to improved resurfacing of the lesion with hyaline-like repair cartilage.

g. The implant, after introducing into a meniscal tear or trephination channel, or rotator cuff repair site, provides at least one of elicits more macrophages, angiogenic blood vessels and mesenchymal stem cells than untreated defects, and thereby restoring biomechanical integrity to the ruptured connective tissue.

h. For dental sinus augmentation, tendon insertion sites, and bone void filler applications, the implant promotes angiogenesis and woven bone formation while minimizing bone resorption.

i. The implant, prior to freeze-drying, may be further incorporated with peptides, oligosaccharides, collagen, atelocollagen, clotting factors, chemotactic factors, bioactive lipids, bioactive factors, minerals, but not limited to these additives.

j. For item (i), the peptide may be a cationic amphiphilic peptide and/or a biomimetic peptide that stimulates neutrophil chemotaxis without activating neutrophil degranulation.

SUMMARY

As used herein, the term "controlled rehydration agent" refers to a substance whose composition or formulation controls the rate of rehydration of a lyophilized material.

In one aspect, there is provided a lyophilized scaffold composition comprising at least one polysaccharide, wherein said scaffold is substantially solid and capable of being formed into a desired shape; wherein the at least one polysaccharide has a protonation level resulting in controlled rehydration of said scaffold, such that when said scaffold is contacted with at least one of a neutral aqueous solution, blood, blood derived fluid and combinations thereof, said scaffold:

i) forms a microparticle dispersion and at least one of the following:
ii) stimulates tissue remodeling;
iii) stimulates anabolic wound repair;
iv) stabilizes a clot, preferably a fibrin clot, blood clot or combination thereof;
v) stimulates neutrophil chemotaxis;
vi) stimulates macrophage chemotaxis;
vii) stimulates angiogenesis;
viii) stimulates mesenchymal cell chemotaxis;
ix) suppresses fibrosis;
x) stimulates osteoclast formation and bone resorption;
xi) stimulates woven bone repair; and combinations thereof.

In another aspect, there is provided a process for preparing a lyophilized scaffold composition comprising at least one polysaccharide and optionally at least one controlled rehydration agent, wherein the at least one polysaccharide has a protonation level resulting in controlled rehydration and microparticle dispersion when contacted with at least one of a neutral aqueous solution, blood, blood derived fluid and combinations thereof; comprising the steps of a) Contacting the at least one polysaccharide with water in the presence of an acid to form an aqueous mixture,
b) Sterilizing the aqueous mixture, and
c) Lyophilizing the aqueous mixture to give a lyophilized scaffold composition.

In one aspect there is provided a lyophilized scaffold composition comprising at least one polysaccharide, wherein said composition rehydrates in a controlled manner.

In one embodiment, said composition further comprises at least one controlled rehydration agent. Preferably the polysaccharide is selected from chitosan, dextran and combinations thereof. Preferably the chitosan has a molecular weight of from about 5,000 Daltons (Da) to about 400,000 Da, more preferably from about 8,000 Da to about 350,000 Da and most preferably from about 10,000 Da to about 300,000 Da. If present in the formulation, the at least one controlled rehydration agent is preferably selected from the group consisting of low molecular mass chitosan, ultra-low molecular mass chitosan, chitosan oligomers, monomeric glucosamine and N-acetyl glucosamine. In a preferred embodiment, the lyophilized polysaccharide is in the form of a scaffold. In another preferred embodiment the lyophilized polysaccharide is porous, preferably highly porous, more preferably very highly porous, most preferably ultraporous.

In another aspect, there is provided the use of a lyophilized scaffold composition comprising at least one polysaccharide and optionally at least one controlled rehydration agent, wherein the at least one polysaccharide has a protonation level resulting in controlled rehydration and microparticle dispersion when contacted with at least one of a neutral aqueous solution, blood, blood derived fluid and combinations thereof, to modify a blood coagulum and promote wound repair in a mammal.

In another embodiment, the at least one controlled rehydration agent is selected from an acid. The acid is selected to provide an optimal level of polysaccharide protonation state. More preferably the acid is a pharmaceutically acceptable acid. Most preferably the acid is selected from the group consisting of hydrochloric acid, lactic acid, acetic acid and combinations thereof. In one embodiment, when chitosan is the at least one polysaccharide, the at least one controlled rehydration agent comprises an acid which generates a protonation state between 70% and 100% protonation of free amine groups, preferably between 80% and 98% protonation. In one embodiment, for a chitosan having a molecular weight no more than about 10,000 Da, said protonation state is preferably between 80% and 100% protonation. In another embodiment, for a chitosan having a molecular weight greater than 10,000 Da, said protonation state is preferably between 90% and 100%.

In another embodiment, the lyophilized polysaccharide is in the form of a pharmaceutically acceptable acid salt.

In another embodiment, the lyophilized polysaccharide composition further comprises at least one mineral selected from the group consisting of calcium carbonate, calcium phosphate, polytriphosphate, hydroxyapatite and combinations thereof.

In another aspect there is provided a lyophilized chitosan scaffold composition comprising chitosan and at least one controlled rehydration agent. Preferably the chitosan has a molecular weight from about 5,000 Da to about 400,000 Da, more preferably from about 8,000 Da to about 350,000 Da and most preferably from about 10,000 Da to about 300,000 Da. The at least one controlled rehydration agent is selected from the group consisting of ultra-low molecular mass chitosan, chitosan oligomers, monomeric glucosamine and N-acetyl glucosamine. In a preferred embodiment, the chitosan is in the form of a scaffold. In another preferred embodiment the chitosan is porous, preferably highly porous, more preferably very highly porous, most preferably ultraporous.

In another embodiment, the at least one controlled rehydration agent is selected from an acid. The acid is selected to provide an optimal level of chitosan protonation state. More preferably the acid is a pharmaceutically acceptable acid. Most preferably the acid is selected from the group consisting of hydrochloric acid, lactic acid, acetic acid and combinations thereof. The at least one controlled rehydration agent comprises an acid which generates a protonation state between 70% and 100% protonation of free amine groups, preferably between 80% and 98% protonation. In one embodiment, for a chitosan having a molecular weight no more than about 10,000 Da, said protonation state is preferably between 80% and 100% protonation. In another embodiment, for a chitosan having a molecular weight greater than 10,000 Da, said protonation state is preferably between 90% and 100%.

In another embodiment, the lyophilized chitosan scaffold composition further comprises at least one chitosan amino sugar selected from but not limited to glucosamine and N-acetyl glucosamine.

In another embodiment, the chitosan preferably has a degree of deacylation (DDA) of from about 50% to about 100%, more preferably from about 70% to about 90% and most preferably about 80%.

In another embodiment, the chitosan is in the form of a pharmaceutically acceptable acid salt. Preferably the acid is an inorganic acid, more preferably a hydrohalic acid. Most preferably the acid is hydrochloric acid. Preferably the inorganic acid is present from about 70% to about 110% molar ratio with free amino groups of the chitosan polymer, more preferably from about 75% to about 105% molar ratio and most preferably from about 80% to about 100% molar ratio. Preferably an 80% to 90% molar ratio is preferred for a chitosan of 10,000 Da or less and a 90% to 100% molar ratio is more preferred for a chitosan of above 10,000 Da.

In another embodiment, the lyophilized chitosan scaffold composition further comprises at least one biological therapeutic protein or other factors that stimulate acute innate immune wound repair responses, preferably said at least one biological therapeutic protein or other factors includes but is not limited to cationic amphiphilic anti-microbial peptides or biomimetic peptides that activate cell migration, including but not limited to polypeptides or subfragments of SDF-1/CXCL12, chemokines, CXCL10/IP-10, IL-1 receptor antagonist, G-CSF, GM-CSF, M-CSF, interferon beta, interferon alpha, IL-4, IL-13, IL-10, and peptides, bioactive lipids such as $LTB_4$ or $PGE_2$, or factors that activate neutrophil chemotaxis without inducing degranulation.

In another embodiment, the lyophilized chitosan scaffold composition further comprises at least one biological therapeutic factor that stimulate angiogenesis including but not limited to recombinant factor VIIa (rhFVIIa), thrombin, Tissue Factor, VEGF, tryptase, MMP-13, IL-8, MCP-1.

In another aspect there is provided a process for preparing a lyophilized polysaccharide scaffold composition described herein, comprising the steps of contacting at least one polysaccharide and at least one controlled rehydration agent with water in the presence of an acid under sterile conditions to form an aqueous mixture and lyophilizing the mixture to give the lyophilized polysaccharide scaffold composition. Preferably the at least one polysaccharide is selected the group consisting of chitosan, chitosan amino sugar, dextran and combinations thereof. The chitosan preferably has a molecular weight from about 5,000 Da to about 400,000 Da, more preferably from about 8,000 Da to about 350,000 Da and most preferably from about 10,000 Da to about 300,000 Da. Preferably the at least one controlled rehydration agent is selected from the group consisting of ultra-low molecular mass chitosan, chitosan oligomers, monomeric glucosamine and N-acetyl glucosamine.

In another embodiment of the process, the at least one controlled rehydration agent is selected from an acid. The acid is selected to provide an optimal level of chitosan protonation state. More preferably the acid is a pharmaceutically acceptable acid. Most preferably the acid is selected from the group consisting of hydrochloric acid, lactic acid, acetic acid and combinations thereof. In one embodiment, the at least one controlled rehydration agent comprises an acid which generates a protonation state between 70% and 100% protonation of free amine groups, preferably between 80% and 98% protonation. In one embodiment, for a chitosan having a molecular weight no more than about 10,000 Da, said protonation state is preferably between 80% and 100% protonation. In another embodiment, for a chitosan having a molecular weight greater than 10,000 Da, said protonation state is preferably between 90% and 100%.

In another embodiment of the process, the chitosan preferably has a degree of deacylation (DDA) of from about 50% to about 100%, more preferably from about 70% to about 90% and most preferably about 80%.

The at least one polysaccharide is preferably present in the aqueous mixture in an amount of about 0.2 to about 7% weight by volume (w/v), more preferably about 0.3 to about 5% w/v and most preferably about 0.5 to about 3% w/v. In a preferred embodiment, when the at least one controlled rehydration agent comprising a chitosan monomer or a short-chain chitosan polymer is preferably present in the aqueous mixture in an amount of about 0.2 to about 10% w/v, more preferably about 0.3 to about 7% w/v and most preferably about 0.5 to about 5% w/v.

In a preferred embodiment, when the at least one controlled rehydration agent comprises an acid, the pH of the aqueous mixture is from about 2 to about 6 to provide a chitosan amine protonation state of 100% to about 80%, most preferably from about 2 to about 5.5 to provide a chitosan amine protonation state of 100% to about 90%. In a preferred embodiment, the osmolality of the aqueous mixture is from about 5 to about 200 mOsm.

In another preferred embodiment, the lyophilizing step is carried out under aseptic conditions by controlled cooling the aqueous mixture from about room temperature to about −40° C. to freeze the solution and then drying the mixture. Preferably the cooling rate is about 1° C. per minute. Preferably the drying steps take place under a vacuum, preferably under a vacuum of about 100 m Torr. In one embodiment, the primary drying step may last from about 36 hours to about 54 hours, most preferably about 48 hours. Preferably the secondary drying step is carried out by warming at a rate of 0.05° C. to 0.2° C., more preferably 0.1° C. per minute, preferably from about −40° C. to about 30° C., for a period of time between 6 and 24 hours, preferably 12 hours, and followed by another step of maintaining isothermal temperature at about 30° C. for about 6 hours prior to removing the vacuum.

In another aspect there is provided a process for preparing a lyophilized chitosan scaffold composition comprising the steps of contacting chitosan and at least one controlled rehydration agent with water under sterile conditions in the presence of an acid to form an aqueous mixture, and lyophilizing the mixture to give the lyophilized chitosan scaffold composition. Preferably the composition further comprises a chitosan amino sugar. The chitosan preferably has a molecular weight from about 5,000 Da to about 400,000 Da, more preferably from about 8,000 Da to about 350,000 Da and most preferably from about 10,000 Da to about 300,000 Da. Preferably the at least one controlled rehydration agent is selected from the group consisting of ultra-low molecular mass chitosan, chitosan oligomers, monomeric glucosamine and N-acetyl glucosamine.

In another embodiment of the process, the at least one controlled rehydration agent is selected from an acid. The acid is selected to provide an optimal level of chitosan protonation state. More preferably the acid is a pharmaceutically acceptable acid. Most preferably the acid is selected from the group consisting of hydrochloric acid, lactic acid, acetic acid and combinations thereof.

In another embodiment of the process, the chitosan preferably has a degree of deacylation (DDA) of from about 50% to about 100%, more preferably from about 70% to about 90% and most preferably about 80%.

The chitosan of the process is preferably present in the aqueous mixture in an amount of about 0.2 to about 7% weight by volume (w/v), more preferably about 0.3 to about 5% w/v and most preferably about 0.5 to about 3% w/v. The at least one controlled rehydration agent is preferably present in the aqueous mixture in an amount of about 0.2 to about 10% w/v, more preferably about 0.3 to about 7% w/v and most preferably about 0.5 to about 5% w/v.

In a preferred embodiment of the process, the pH of the aqueous mixture is from about 2 to about 6 to provide a chitosan amine protonation state of 100% to about 80%, most preferably from about 2 to about 5.5 to provide a chitosan amine protonation state of 100% to about 90%. In a preferred embodiment, the osmolality of the aqueous mixture is from about 5 to about 200 mOsm.

In another preferred embodiment of the process, the lyophilizing step is carried out by cooling the aqueous mixture from about room temperature to about −40° C. and drying the mixture. Preferably the cooling is carried out at a cooling rate of about 1° C. per minute. Preferably the drying steps take place under vacuum, preferably a vacuum of about 100 m Torr. The primary drying step can last from about 36 hours to about 54 hours, most preferably about 48 hours. Preferably the secondary drying step is carried out by warming at a rate of 0.05° C. to 0.2° C., more preferably 0.1° C. per minute, preferably from about −40° C. to about 30° C., for a period of time between 6 and 24 hours, preferably 12 hours, and followed by another step of maintaining isothermal temperature at about 30° C. for about 6 hours prior to removing the vacuum.

In another aspect there is provided the use of a lyophilized polysaccharide scaffold composition to promote blood coagulation and wound repair in a mammal. The composition comprises at least one polysaccharide and at least one controlled rehydration agent. Preferably the at least one polysaccharide is selected from chitosan. Preferable the chitosan has a molecular weight of from about 5,000 Daltons (Da) to about 400,000 Da, more preferably from about 8,000 Da to about 350,000 Da and most preferably from about 10,000 Da to about 300,000 Da. Preferably the at least one controlled rehydration agent is selected from the group consisting of ultra-low molecular mass chitosan, chitosan oligomers, monomeric glucosamine and N-acetyl glucosamine. In another embodiment the at least one controlled rehydration agent is selected from the group consisting of dextran of about 2,000 Da to 20,000 Da and most preferably from about 3,000 to 8,000 Da. In a preferred embodiment, the lyophilized composition is in the form of a scaffold. In another preferred embodiment the lyophilized composition may be porous, preferably highly porous, more preferably very highly porous, most preferably ultraporous.

In another embodiment of the use, the at least one controlled rehydration agent is selected from an acid. The acid is selected to provide an optimal level of chitosan protonation state. More preferably the acid is a pharmaceutically acceptable acid. Most preferably the acid is selected from the group consisting of hydrochloric acid, lactic acid, acetic acid and combinations thereof.

In another embodiment, the lyophilized polysaccharide is in the form of a pharmaceutically acceptable acid salt. Preferably the acid is an inorganic acid, more preferably a hydrohalic acid. Most preferably the acid is hydrochloric acid. When the at least one controlled rehydration agent comprises an acid, it generates a protonation state between 70% and 100% protonation of free amine groups, preferably between 80% and 98% protonation. In one embodiment, for a chitosan having a molecular weight no more than about 10,000 Da, said protonation state is preferably between 80% and 100% protonation. In another embodiment, for a chitosan having a molecular weight greater than 10,000 Da, said protonation state is preferably between 90% and 100%.

In one embodiment, wound repair includes, but not be limited to, the processes of angiogenesis, cell chemotaxis, tissue remodeling, viscoelastic extracellular matrix deposition for joint repair, fracture repair, meniscal repair, rotator cuff repair, suppression of fibrosis, revascularization and anabolic tissue regeneration. In another embodiment, the composition is administered in a solid form to the wound site.

In another aspect there is provided a kit for wound repair in a mammal comprising a lyophilized scaffold composition comprising at least one polysaccharide and at least one controlled rehydration agent, a cutting tool, an injection tool, a microdrill or micropick and a shaping tool.

In another aspect, a lyophilized polysaccharide scaffold composition may be combined with whole blood or blood elements, preferably in vivo or in vitro followed by in vivo delivery either following combining with whole blood or blood elements, or after fibrin fiber formation, in order to introduce the composition to a bleeding channel, bleeding wound, or a bleeding surface. Preferably the bleeding channel may be created by a diverse array of surgical tools selected from the group consisting of a drill bit, a burr, an awl, a trephination needle, a K-wire, a hollow tube, a Jamshidi needle and combinations thereof. Preferably the bleeding wound is created by accidental trauma or by surgical manipulation. Preferably the bleeding surface may be generated by a tool selected from the group consisting of a shaver, a curette, a scalpel, a scraper, a knife. In a preferred embodiment, the lyophilized polysaccharide scaffold may be used to treat a bleeding wound selected from the group consisting of subchondral bone, bone, periodontal bone, meniscus, tendon insertion site, rotator cuff, tendon insertion site, skin and combinations thereof, and organs, where anabolic wound repair processes such as neutrophil and macrophage chemotaxis, stem cell chemotaxis, angiogenesis, and tissue remodeling are desired.

Further and other embodiments will become apparent to those skilled in the art.

BRIEF DESCRIPTION OF THE FIGURES

FIG. 8G shows that the freeze-dried chitosan implants at day 1 post-surgery have rehydrated in situ and formed particles in the treated drill holes, as shown by the white arrows pointing to the white punctate signal representing red fluorescent 80 kDa RITC-chitosan microparticles (added as a tracer), and grey signal representing green autofluorescent bone tissues around the microdrill holes. (8H) shows a high-magnification image of in situ rehydrated chitosan particles in blood clot inside a sheep microdrill hole at day 1 post-operative (arrows point to grey reticulated chitosan microparticles).

FIG. 11 shows the macroscopic appearance of 9 month repaired control and contralateral treated repair tissues from 2 different sheep (black arrow, 11A1 vs 11A2, 11C1 vs 11C2) and matching images where black tracings were placed over the exposed bone areas (11B1 vs 11B2, 11D1 vs 11D2, respectively). The graph in (11E) shows by quantitative histomorphometry of defect macroscopic resurfacing that treatment with the chitosan scaffold results in more resurfacing of the full-thickness drilled cartilage defect, compared to drilling-alone.

DETAILED DESCRIPTION

Figure 1:
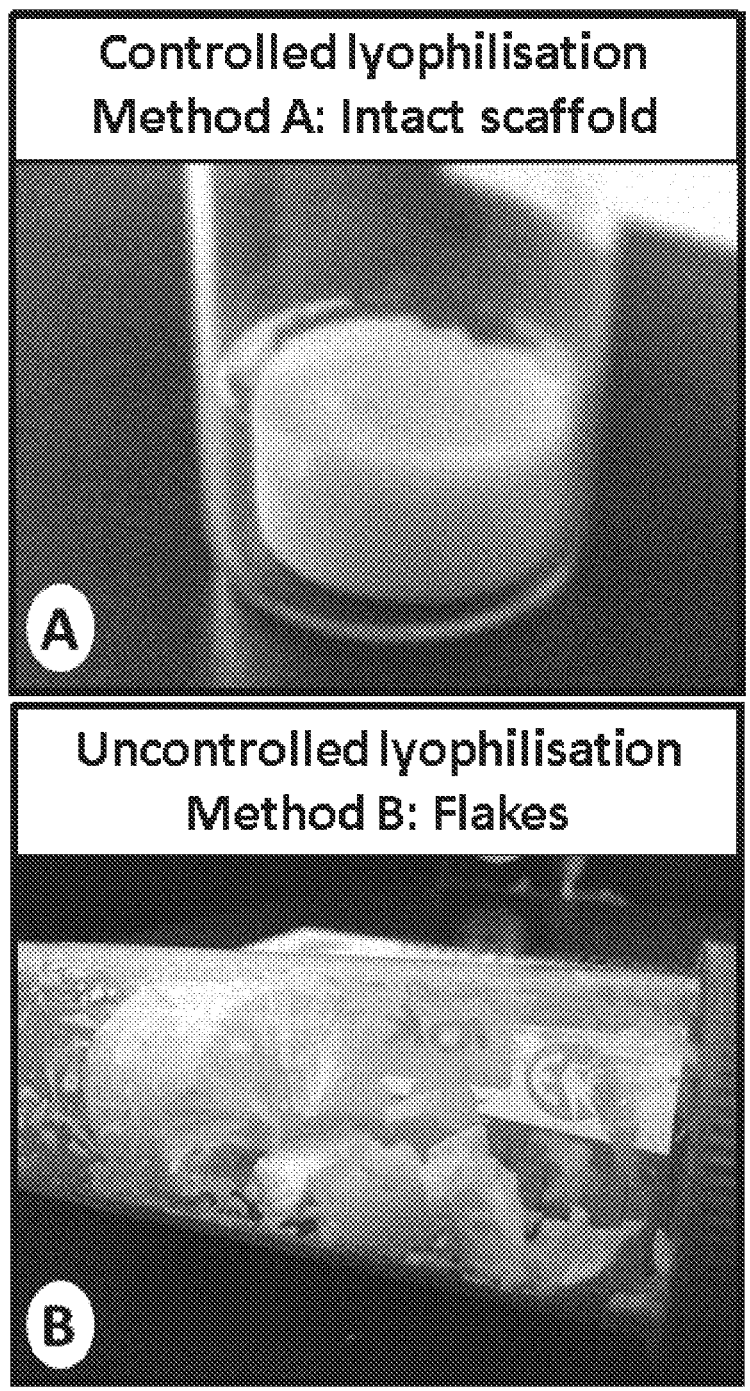
FIG. 1 depicts a freeze-dried composition made by controlled lyophilization presenting with the desired macroscopic appearance and physical properties, versus an uncontrolled lyophilization process leading to sub-optimal macroscopic appearance and physical properties. Controlled freeze-dry condition A (FIG. 1A) produced an intact 3-D cylinder-shaped chitosan scaffold whereas freeze-dry condition B (FIG. 1B) in a standard Labconco apparatus produced chitosan flakes with poor mechanical integrity that cannot be cored or shaped.

In one aspect, there is provided a lyophilized polysaccharide scaffold composition, preferably a lyophilized chitosan scaffold composition, that spontaneously forms a hydrated microparticle dispersion after contact with blood or blood-derived fluids and stimulate anabolic wound repair processes including, but not limited to, neutrophil and macrophage migration, stem cell migration, angiogenesis, cell chemotaxis, tissue remodeling, bone resorption, woven bone repair, suppression of fibrosis, and viscoelastic extracellular matrix deposition for joint repair.

In a preferred embodiment, there is provided a solid lyophilized ultraporous chitosan scaffold which slowly rehydrates in blood, blood plasma, platelet-rich plasma, fibrin glue, or in situ in a bleeding defect, to spontaneously form a resident chitosan microparticle dispersion in the coagulum, in order to stimulate local anabolic processes including recruitment of neutrophils and macrophages, promote angiogenesis, bone remodeling, and enhance cartilage repair tissue volume when directly delivered to bleeding subchondral bone, or to promote angiogenesis in repairing meniscal tears.

The composition may be useful for local delivery of dispersed chitosan microparticles in a fibrin clot, promoting hemostasis for promoting wound remodeling, revascularization, anabolic tissue regeneration. In a further aspect, the composition forms an implant by rehydrating the solid freeze-dried scaffold ex vivo in fibrinogen-containing fluids that are subsequently made to coagulate through thrombin activation and spontaneous fibrin clot formation.

The solid chitosan scaffold composition may be administered more easily to bleeding surgical defects compared to a liquid solution or powder or flakes. The composition dissolves over time post-delivery which permits more control over the location of delivery compared to formulations that dissolve instantly or within a few seconds upon contact with blood. The composition allows for direct administration of the chitosan scaffold to an accessible surgical site which improves ease-of-use and reduces the amount of time to carry out the treatment compared to other methods that require ex-vivo manipulation. In one example, the composition permits control over the mass of scaffold administered to a bleeding surgical site compared to a liquid formulation that can spill out of the lesion site. In one aspect, the composition undergoes delayed rehydration and microparticle dispersion throughout the blood or blood-derived fluid allowing for the chitosan scaffold to become dispersed in the coagulum for efficient retention of the chitosan scaffold at the surgical site. This delayed rehydration being achieved through the use of at least one controlled rehydration agent selected from the group consisting of low molecular mass chitosan, ultra-low molecular mass chitosan, chitosan oligomers, monomeric glucosamine, N-acetyl glucosamine, at least one acid preferably selected from the group consisting of hydrochloric acid, lactic acid and acetic acid.

Improved control over in vivo biodegradation kinetics has unexpectedly been achieved with the composition, compared to prior art aggregated chitosan polymer implants or solid chitosan scaffold formulations that are unable to spontaneously form a microparticle dispersion after contact with blood or blood-derived fluids. Furthermore, the solid and dry chitosan scaffold composition may be kept at room temperature for an extended period of time as would be understood by a person skilled in the art without resulting in modification of the chitosan polymer chain by hydrolytic degradation.

In another aspect there is provided a process for preparing a solid polysaccharide scaffold composition comprising lyophilizing an aqueous mixture of a polymeric cation, preferably comprising chitosan, where water is a porogen occupying ≥80%, preferably ≥90% and most preferably ≥95% of the initial mass of the solution, to give a lyophilized polysaccharide scaffold with a high porosity. In a preferred embodiment, the pH of the aqueous mixture is from about 2 to about 6, most preferably from about 2 to about 5.5. The lyophilization is preferably carried out in at least 3 steps, which include at least a freezing, a primary drying, and a secondary drying step. The freezing step can be carried out by cooling the aqueous mixture under a slight vacuum, at about 600 Torr to about 400 Torr, more preferably 500 Torr, preferably from about room temperature to about −40° C. Preferably the cooling is carried out at a cooling rate of about 1° C. per minute. Preferably, the primary drying step takes place under a vacuum, preferably of about 100 mTorr. Preferably, the primary drying step takes place at constant shelf temperature, preferably at about −40° C. The primary drying step may last from about 36 hours to about 54 hours, most preferably about 48 hours. Preferably the secondary drying step is carried out by warming at a rate of 0.05° C. to 0.2° C., more preferably 0.1° C. per minute, preferably from about −40° C. to about 30° C., for a period of time between 6 and 24 hours, preferably 12 hours, and followed by another step of maintaining isothermal temperature at about 30° C. for about 6 hours prior to removing the vacuum. The vials are preferably brought to room pressure by purging with argon followed by storage at 4° C. to 25° C. The resulting lyophilized polysaccharide scaffold composition has sufficient mechanical resiliency to be shaped with a razor or biopsy punch or Jamshidi needle.

In another aspect, there is provided a lyophilized composition comprising a cationic polysaccharide, preferably chitosan, formulated with an appropriate protonation state and osmolality for spontaneous microparticle dispersion after rehydration in blood plasma. The composition is lyophilized from an aqueous mixture such that the water acts as a porogen to generate a semi-rigid mass with a very highly porous structure. The dispersion of polysaccharide as microparticles in blood or blood-derived liquids and subsequent blood coagulation is controlled by the molecular weight and protonation state of the polysaccharide solution at the time of lyophilization. Chitosan protonation is preferably from about 80% to about 100% for a chitosan of 10 kDa and less and at least about 90% to about 100% for a chitosan above 10 kDa. In one embodiment, the cationic polysaccharide is a polymeric cation, preferably chitosan, preferably present an amount of about 0.2 to about 7% weight by volume (w/v), more preferably about 0.3 to about 5% w/v and most preferably about 0.5 to about 3% w/v.

In another embodiment, the composition further comprises a variable proportion of at least one controlled rehydration agent preferably present in an amount of about 0.2 to about 10% w/v, more preferably about 0.3 to about 7% w/v and most preferably about 0.5 to about 5% w/v, the controlled rehydration agent being selected from the group consisting of a low molecular mass chitosan, ultra-low molecular mass chitosan, chitosan oligomers, monomeric glucosamine and N-acetyl glucosamine to control the delayed kinetics of in situ rehydration of polysaccharide in blood plasma. Upon rehydration the polysaccharide polymer chains spontaneously rehydrate and form dispersed microparticles at the pH and ionic strength of liquid blood or other body fluids. The composition being compatible with propagation of the intrinsic coagulation cascade and fibrin clot formation.

In a preferred embodiment, the polysaccharide is selected form chitosan having a molecular weight of from about 5,000 Daltons (Da) to about 400,000 Da, more preferably from about 8,000 Da to about 350,000 Da and most preferably from about 10,000 Da to about 300,000 Da. In a preferred embodiment, the chitosan composition may further comprise chitosan amino sugars (including but not limited to glucosamine or N-acetyl glucosamine) to permit further time-delayed rehydration of lyophilized chitosan in blood plasma or whole blood. In a preferred embodiment, if dextran is present in the composition, the dextran has a molecular weight of about 3,000 to 10,000 Da, and more preferable around 5,000 Da.

In another preferred embodiment, the composition further comprises a pharmaceutically acceptable acid salt. Preferably the acid is an inorganic acid, more preferably a hydrohalic acid. Most preferably the acid is hydrochloric acid. In one embodiment, the inorganic acid is present from about 70% to about 110% molar ratio, more preferably from about 75% to about 105% molar ratio and most preferably from about 80% to about 100% molar ratio. The preferred osmolality of the composition prior to lyophilization is between 5 and 200 mOsm.

Without being bound by theory, it is believed that the use of the composition ensures a more rapid hemostasis, and the attraction of higher numbers of wound repair cells that normally migrate to blood clots, including neutrophils and macrophages, for a longer period of time compared to a natural hematoma that degrades spontaneously within 1 to 2 weeks post-surgery. The use of the composition also indirectly promotes (1) recruitment of blood vessels and mesenchymal stem cells to wounds, (2) recruitment of osteoclasts and blood vessels to subchondral bone defects, (3) subchondral bone plate remodeling, (4) suppression of fibrosis and (5) bone-induced chondroinduction at the base of an articular cartilage lesion, key features of regenerating connective tissues, and endochondral articular cartilage regeneration. In addition, in vivo degradation kinetics are tunable by chitosan molecular mass which remains stable during storage, therefore allowing a novel and inventive way to control the degree of increased cell recruitment and post-implant time frame of blood clot amplification.

The following non-limiting examples are provided.

EXAMPLES

Example 1

Composition and Method to Prepare Mechanically Rigid Lyophilized Chitosan Formulations that can be Cored with a Biopsy Punch or Shaped with a Scalpel Sterile liquid chitosan formulations were prepared with chitosan dissolved in HCl pH 2 to 5.5 (10 kDa, 85 kDa, or 150 kDa, 80% DDA, or 10 kDa 90% DDA) with or without bulking agent or lyoprotectant (sucrose, trehalose, dextrose, sorbitol, glucosamine-HCl, N-acetyl glucosamine). Some formulations contained bulking agent-only. Other formulations contained different ratios of 10 kDa and 150 kDa chitosan. Some chitosan formulations were prepared at 80% protonation of free amine groups of glucosamine monomer and other formulations were prepared at 98% protonation of free amine groups prior to lyophilization. Some chitosan formulations contained trace rhodamine isothiocyanate (RITC) chitosan with matching molecular mass and DDA to permit tracking of chitosan particle dispersion in plasma and water. Solutions were lyophilized under aseptic conditions in glass or plastic vials using 2 distinct methods.

Lyophilization method (A): Sterile liquid formulations were lyophilized under aseptic conditions in glass vials by cooling at 1° C. per minute from 25° C. to −40° C. at about 500 Torr and then submitted to primary drying at −40° C., 100m Torr for 48 hours in a Laboratory Series PLC Freeze-Dryer (Millrock Technologies Inc), followed by a secondary drying cycle where they were gradually warmed from −40° C. to 30° C. at 100 mTorr during 12 hours then kept isothermal at 30° C. for 6 hours. The vials were then brought to room temperature and pressure, purged with argon and stored at 4° C.

Lyophilization method (B): Sterile liquid formulations at room temperature in glass vials or plastic tubes were flash-frozen or placed in a −80° C. freezer then transferred to a standard laboratory freeze-drier (Labconco FreeZone 2.5 liter freeze dry system), the condenser temperature was set to −80° C. and maximal vacuum (<0.133 mBar) for 72 hours, then the vaccum was broken and samples warmed to room temperature. Note that in a standard apparatus such as the Labconco instrument, the sample temperature cannot be controlled precisely at any step, because the sample typically has a different temperature (between 0° C. and −70° C.) than that of the condenser (−80° C.).

Physical handling test: Some scaffolds prepared by lyophilization method (A) were rigid and could be cored with a 1.5 mm inner diameter dermal biopsy punch, while others formed a dense matted scaffold with high entanglement, or fluffy consistency that could not be cored with a biopsy punch (FIG. 1, Tables 1 & 2). In general, scaffolds with good handling properties using low molecular weight chitosan require a minimum of 5 mg/mL sugar, either pure chitosan, 5 or 10 mg/mL chitosan with bulking agent, or a mixture of 2.5 mg/mL chitosan and bulking agent, with chitosan at 80% to 98% chitosan protonation. For chitosans with higher molecular weight (85 to 150 kDa), the best handling properties were discovered to require a higher concentration of chitosan (10 or 20 mg/mL), at full 100% protonation, and did not require a lyoprotectant, to form a rigid scaffold that could be cored with a dermal punch (Table 2). All scaffolds prepared by lyophilization method (B) had unacceptable handling properties, including fluffy material, crumbs, flakey, or a dense matted material that was not rigid and could not be cored with a biopsy punch. (FIG. 1B, Table 3).

TABLE 1

Scaffolds prepared using Lyophylization method A, with 80% protonation of chitosan (pH 4 to 5.5) and resulting properties and biological reactions.

| (formulation) Chitosan tested | [Chitosan] in HCl pH 4.5-5.0 | RITC-chitosan | Bulking agent (Glc = glucosamine; GlcNA = N-acetyl glucosamine) Or additive | Experiment | Physical Handling properties Good: rigid cake that can be cored | Biological reaction R: rehydrate D: dispersed particles S: slow to dissolve A: angiogenic B: bone remodel FBG: foreign body giant cells —: not done | Pass/Fail |
|---|---|---|---|---|---|---|---|
| 1) 10 kDa, 81.9% DDA | 1 mg/mL | yes | none | MD-46.2.2 | Fail | R, D, —, —, —, — | Fail |
| 2) 10 kDa, 81.9% DDA | 5 mg/mL | yes | none | MD-46.2.2 | Good | R, D, —, —, —, — | Pass |
| 3) 10 kDa, 81.9% DDA | 5 mg/mL | yes | NaCl (150 mM) | MD-46.2.2 | Good | R, D, —, —, —, — | Pass |
| 4) 10 kDa, 81.9% DDA | 5 mg/mL | yes | none | MD-46.1 | Good | R, D, S, A, B, NoFBG | Pass |
| 5) 10 kDa, 81.9% DDA | 10 mg/mL | yes | none | MD-46.1 | Good | R, D, S, A, B, NoFBG | Pass |
| 6) 10 kDa, 81.9% DDA | 5 mg/mL | yes | 50 mg/mL dextran-5 | MD-46.1.3 | Good | R, D, S, A, B, (FBG) | Pass |
| 7) none | none | none | 50 mg/mL dextran-5 | MD-46.1.2 | Good | R, —, S, A, No, (FBG) | Pass |

TABLE 1-continued

Scaffolds prepared using Lyophylization method A, with 80% protonation of chitosan (pH 4 to 5.5) and resulting properties and biological reactions.

| (formulation) Chitosan tested | [Chitosan] in HCl pH 4.5-5.0 | RITC-chitosan | Bulking agent (Glc = glucosamine; GlcNA = N-acetyl glucosamine) Or additive | Experiment | Physical Handling properties Good: rigid cake that can be cored | Biological reaction R: rehydrate D: dispersed particles S: slow to dissolve A: angiogenic B: bone remodel FBG: foreign body giant cells —: not done | Pass/Fail |
|---|---|---|---|---|---|---|---|
| 8) 10 kDa, 81.9% DDA | 5 mg/mL | yes | 10 mg/mL Glc-HCl | MD-46.2.2 | Good | R, D, —, —, —, — | Pass |
| 9) 10 kDa, 81.9% DDA | 5 mg/mL | yes | 10 mg/mL GlcNA | MD-46.2.2 | Good | R, D, —, —, —, — | Pass |
| 10) 10 kDa, 81.9% DDA | 5 mg/mL | yes | 10 mg/mL sucrose | MD-46.2.2 | Good | R, D, —, —, —, — | Pass |
| 11) 10 kDa, 81.9% DDA | 4.5 mg/mL | yes | none | MD-46.2.2 | Good | R, D, —, —, —, — | Pass |
| 12) 150 kDa, 81.5% DDA | 0.5 mg/mL | | | | | | |
| 13) 10 kDa, 81.9% DDA | 2.4 mg/mL | yes | 10 mg/mL sucrose | MD-46.1 | Good | R, No, —, —, —, — | Fail |
| 14) 10 kDa, 81.9% DDA | 2.4 mg/mL | yes | 50 mg/mL sucrose | MD-46.1 | Good | R, No, No, No, B, FBG | Fail |
| 15) 10 kDa, 81.9% DDA | 5 mg/mL | yes | 50 mg/mL trehalose | MD-46.1.2 | Good | R, D, No, A, B, FBG | Fail |
| 16) 10 kDa, 81.9% DDA | 2.4 mg/mL | yes | 50 mg/mL sorbitol | MD-46.1 | Good | R, D, No, A, B, FBG | Fail |
| 17) 10 kDa, 81.9% DDA | 1.3 mg/mL | yes | none | MD-46.2.2 | Good | No, No, —, —, — | Fail |
| 18) 150 kDa, 81.5% DDA | 3.8 mg/mL | | | | | | |
| 19) 10 kDa, 81.9% DDA 150 kDa, 81.5% DDA | 3.8 mg/mL 1.3 mg/mL | yes | none | MD-46.2.2 | Fair | No, 35%, —, —, — | Fail |
| 85 kDa, 81.5% DDA | 5 mg/mL | yes | 10 mg/mL sucrose | MD-46.2.2 | Good | No, No, —, —, — | Fail |
| 20) 85 kDa, 81.5% DDA | 5 mg/mL | yes | 10 mg/mL Glc-HCl | MD-46.2.2 | Good | No, 5%, —, —, — | Fail |
| 21) 85 kDa, 81.5% DDA | 5 mg/mL | yes | 10 mg/mL GlcNA | MD-46.2.2 | Good | No, 72%, —, —, — | Fail |
| 22) none | none | none | 50 mg/mL sucrose | MD-46.1.2 | Good | R, —, No, No, No, FBG | Fail |
| 23) none | none | none | 50 mg/mL trehalose | MD-46.1.2 | Good | R, —, No, No, No, FBG | Fail |
| 23A) none | none | None | 50 mg/mL sorbitol | MD-46.1.2 | Good | R, —, No, No, No, FBG | Fail |
| 24) none | none | none | 5 mg/mL dextran-5, or sucrose or trehalose or sorbitol | MD-46.1.1 | Fluffy | R, —, —, —, — | Fail |
| 25) 10 kDa, 81.9% DDA | 2.4 mg/mL | yes | 10 mg/mL dextran-5 | MD-46.1.1 | Fluffy | R, D, —, —, — | Fail |
| 26) 10 kDa, 81.9% DDA | 2.4 mg/mL | yes | 10 mg/mL trehalose | MD-46.1.1 | Fluffy | R, D, —, No, — | Fail |
| 27) 10 kDa, 81.9% DDA | 2.4 mg/mL | yes | 5 mg/mL sorbitol | MD-46.1.2 | Fluffy | R, D, —, —, — | Fail |

TABLE 2

Scaffolds prepared using Lyophylization method A, without bulking agent, at 80% protonation of chitosan (pH 4 to 6.0) or 98% protonation of chitosan (pH 2.5 to 3) and resulting properties and biological reactions.

| Formulation) Chitosan tested | [Chitosan] in HCl | RITC-chitosan | Protonation level of chitosan prior to lyophilization | Experiment | Physical Handling properties Good: rigid cake can core | Biological reaction R: rehydrate D: dispersed particles S: slow to dissolve B: bone remodeling C: cartilage repair at 9 months —: not done | Pass/Fail |
|---|---|---|---|---|---|---|---|
| 28) 10 kDa, 90.2% DDA | 5 mg/mL | yes | 98% (pH 2.5) | MD-46.4 | Good | R, D, —, —, — | Pass |

TABLE 2-continued

Scaffolds prepared using Lyophylization method A, without bulking agent, at 80% protonation of chitosan (pH 4 to 6.0) or 98% protonation of chitosan (pH 2.5 to 3) and resulting properties and biological reactions.

| Formulation) Chitosan tested | [Chitosan] in HCl | RITC-chitosan | Protonation level of chitosan prior to lyophilization | Experiment | Physical Handling properties Good: rigid cake can core | Biological reaction R: rehydrate D: dispersed particles S: slow to dissolve B: bone remodeling C: cartilage repair at 9 months —: not done | Pass/Fail |
|---|---|---|---|---|---|---|---|
| 29) 85 kDa, 80.6% DDA | 5 mg/mL | yes | 98% (pH 2.5) | MD-48.1 | Fluffy | R, Yes in vivo, yes, B, C | Pass |
| 30) 85 kDa, 81.5% DDA | 5 mg/mL | yes | 80% (pH 4.5) | MD-46.2.2 | Matted | No, No, —, —, — | Fail |
| 31) 85 kDa, 80.6% DDA | 20 mg/mL | yes | 80% (pH 4.5) | MD-48.1 | Matted | R, No, S, —, — | Fail |
| 32) 85 kDa, 80.6% DDA | 10 mg/mL + 10 mg/mL sucrose | yes | 98% (pH 2.5) | MD-48.1 | Good | R, No, S, —, — | Fail |
| 33) 85 kDa, 80.6% DDA | 10 mg/mL | yes | 98% (pH 2.5) | MD-48.1 | Good | R, D, S, B, C | Pass |
| 34) 85 kDa, 80.6% DDA | 20 mg/mL | yes | 98% (pH 2.5) | MD-48.1 | Good | R, D, S, B, C | Pass |
| 35) 10 kDa, 81.9% DDA 85 kDa, kDa, 80.6% DDA | 2.5 mg/mL, 2.5 mg/mL | yes | 98% (pH 2.5) | MD-48.1 | Good | R, D, S, B, C | Pass |

TABLE 3

Scaffolds prepared using Lyophilization method B.

| Formulation) Chitosan tested | Chitosan concentration in HCl (80% to 98% protonation) | RITC-chitosan | Bulking agent | Experiment | Physical Handling properties | Biological reaction R: rehydrate D: dispersed A: angiogenic B: bone remodel —: not done | Pass/Fail |
|---|---|---|---|---|---|---|---|
| 36) 10 kDa, 81.9% DDA | 5 mg/mL | yes | none | MD46.2.1 | Fluffy, crumbs | R, D, —, — | Fail |
| 37) 10 kDa, 81.9% DDA | 5 mg/mL | yes | 5 mg/mL sucrose | MD46.2.1 | Fluffy, crumbs | R, D, —, — | Fail |
| 38) 10 kDa, 81.9% DDA | 5 mg/mL | yes | 5 mg/mL glucosamine-HCl | MD46.2.1 | Fluffy, crumbs | R, D, —, — | Fail |
| 39) 85 kDa, 81.5% DDA | 5 mg/mL | yes | none | MD46.2.1 | Fluffy, Matted | Insoluble | Fail |
| 40) 85 kDa, 81.5% DDA | 5 mg/mL | yes | 5 mg/mL sucrose | MD46.2.1 | Fluffy, Matted | Insoluble | Fail |
| 41) 85 kDa, 81.5% DDA | 5 mg/mL in HCl pH 5 | yes | 5 mg/mL glucosamine-HCl | MD46.2.1 | Fluffy, Matted | Insoluble | Fail |
| 42) 10 kDa, 80% DDA (Wako) | 5 mg/mL | yes | none | TEG-19.3 | Flakes | R, D, —, — | Fail |

Example 2

Figure 2:
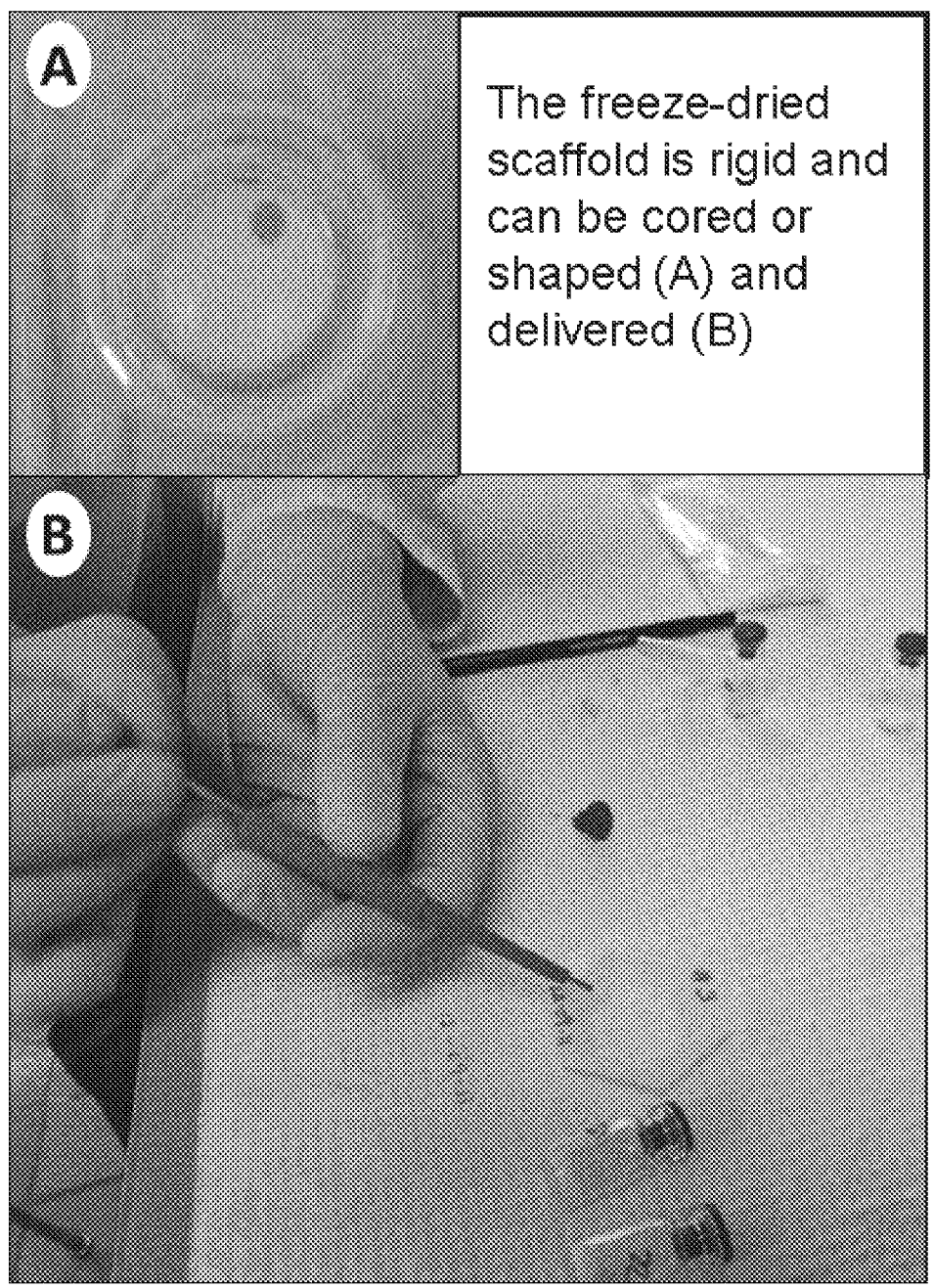
FIG. 2 is a demonstration of chitosan compositions that show the ability to be shaped, delivered with a tool, and to undergo spontaneous microparticle dispersion in coagulating human blood plasma. Chitosan formulations were tested for spontaneous microparticle dispersion in recalcified human citrated plasma in the presence of glass beads to initiate coagulation through the intrinsic coagulation cascade. In this assay, a consistent volume of the freeze-dried chitosan cake was cored and delivered with a dermal biopsy punch (2A-2C) and placed in a 96-well containing 170 µL of human citrated plasma, 10 µL 200 mM $CaCl_2$, and 5 or 10 µL of 10 mg/mL glass beads in $ddH_2O$ (2D). The samples were allowed to rehydrate and coagulate at 37° C. for one hour. Only selected formulations were capable of forming a homogeneous and reticulated microparticle dispersion in blood plasma (2E, 2G, 2I) while other formulations failed to disperse as microparticles (2F, 2H). In a specific example, a lower molecular weight scaffold (10 kDa chitosan-HCl solution freeze-dried at pH 4.5, formulation #2) slowly rehydrated and dispersed as microparticles (2E), while a higher molecular weight scaffold (85 kDa chitosan-HCl solution freeze-dried at pH 4.5, formulation #31) began to rehydrate (2D) but unexpectedly failed to disperse (2F). By lowering the solution pH, a higher molecular weight scaffold (85 kDa chitosan-HCl solution freeze-dried at pH 2.5, formulation #33) slowly rehydrated (2D) and dispersed as microparticles (2G). Combinations of low and high molecular weight chitosan also dispersed as microparticles (2I).
Figure 2:
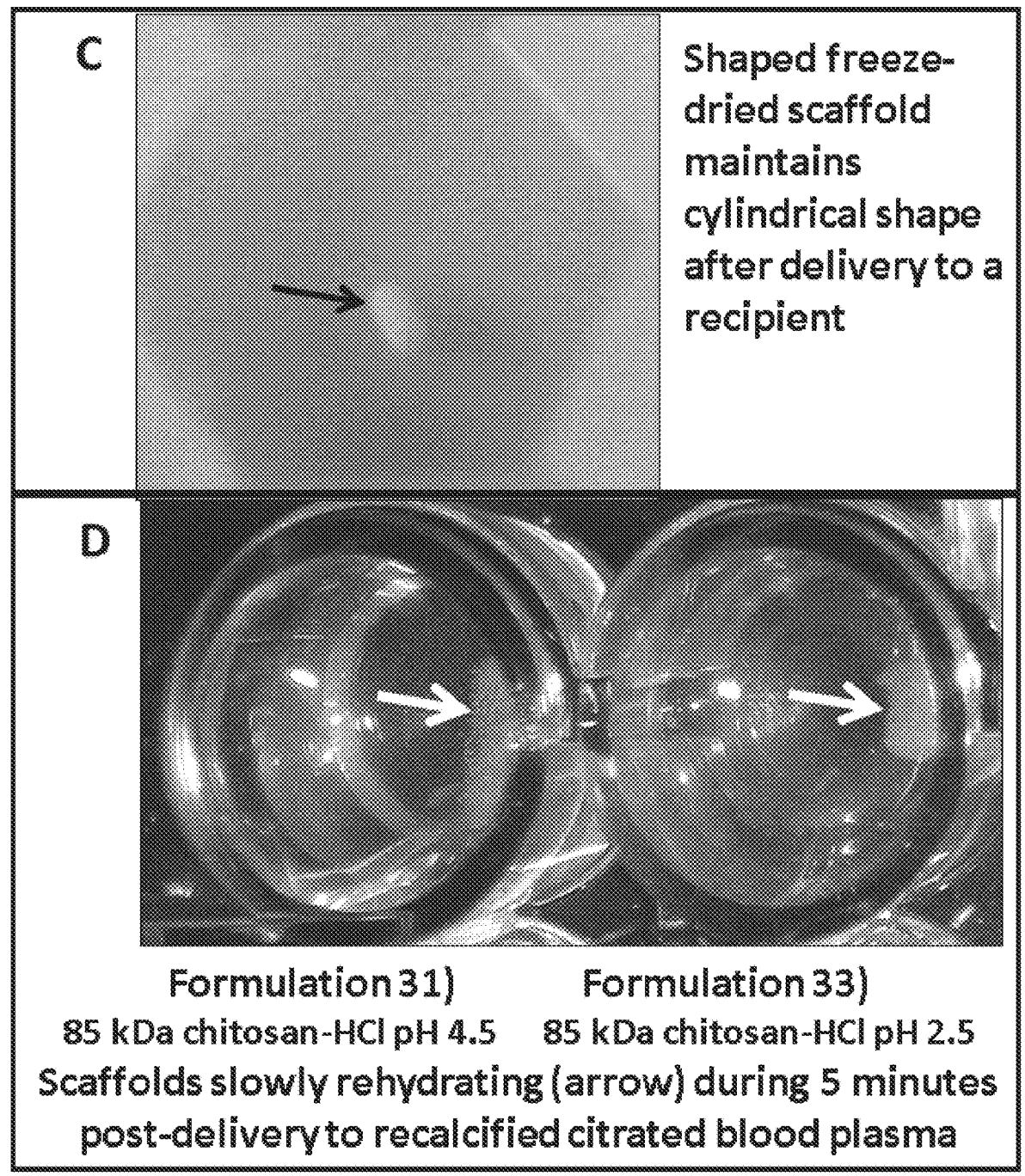
Figure 2:
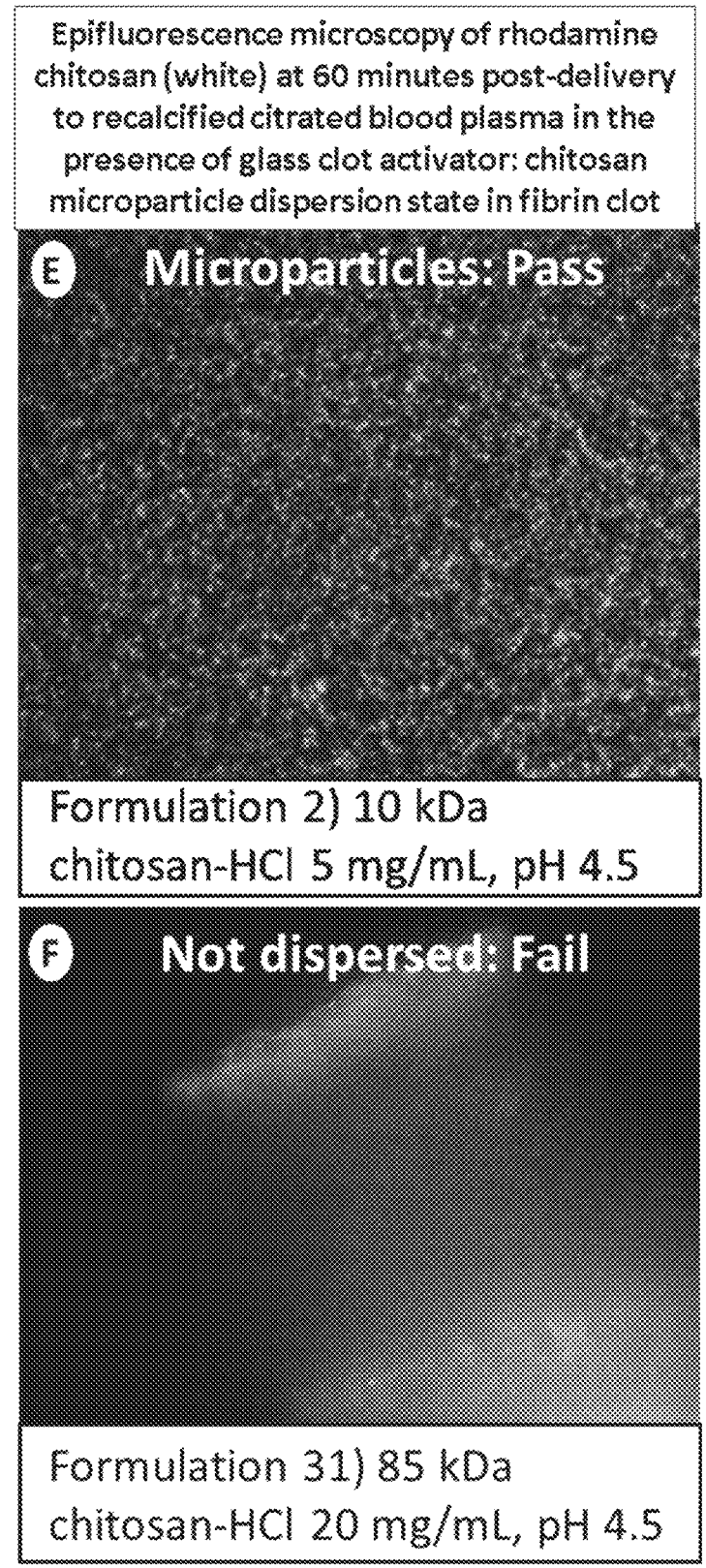
Figure 2:
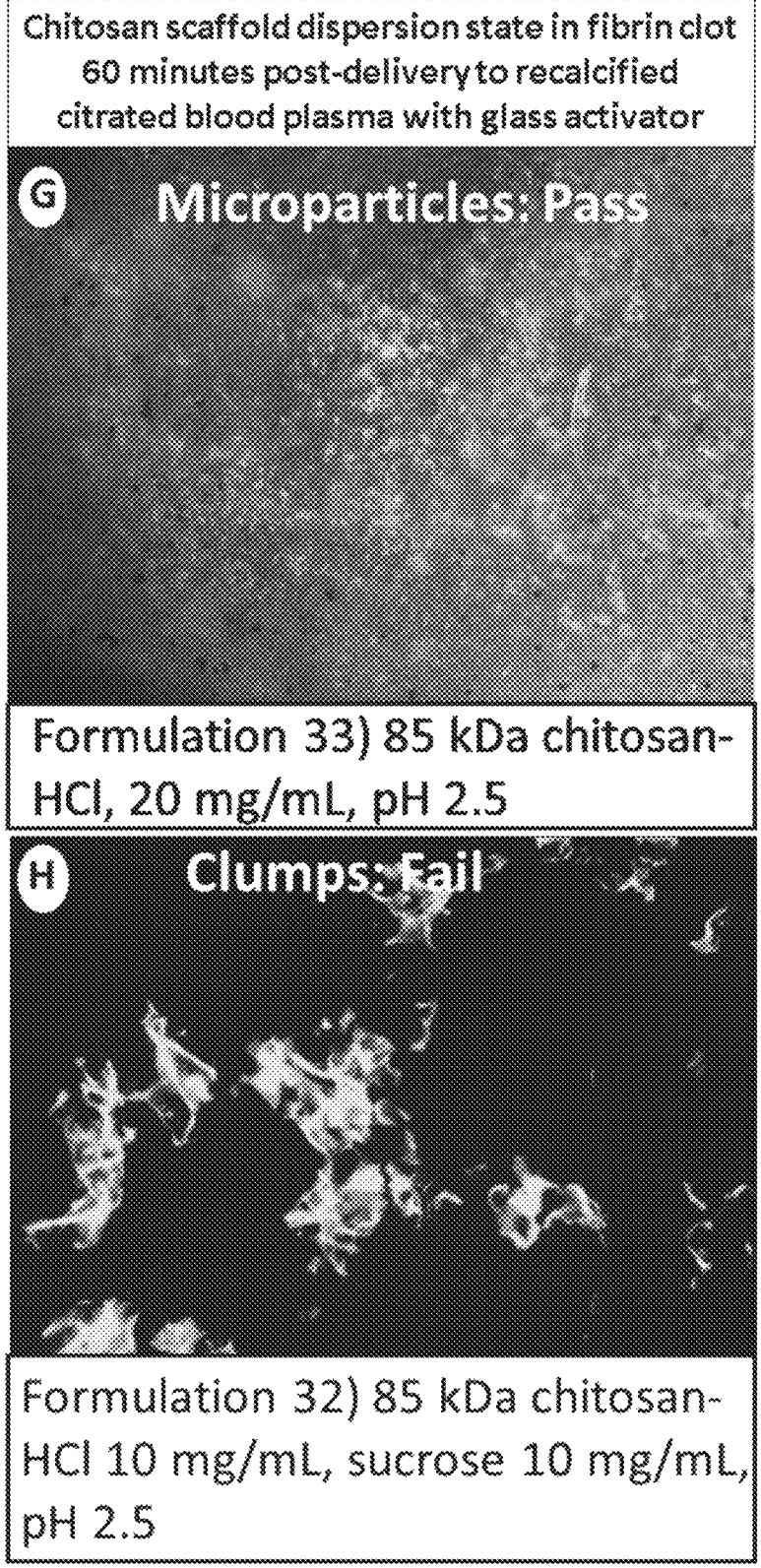
Figure 2:
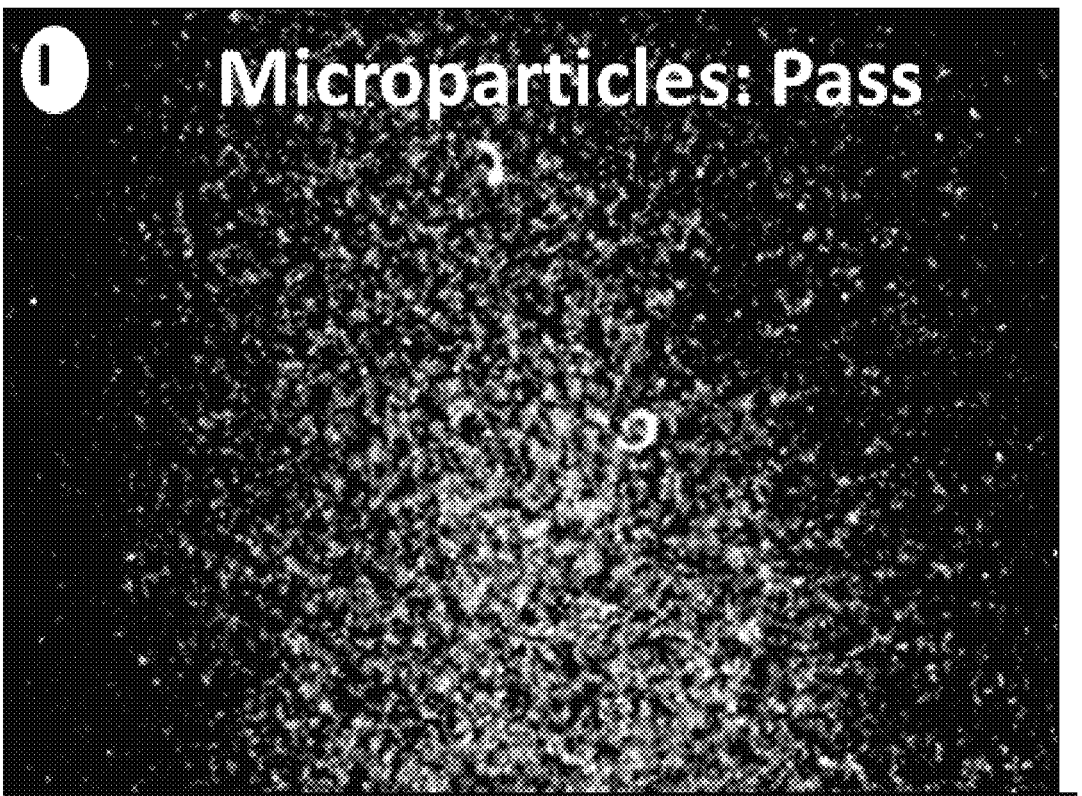

Test to Identify Freeze-Dried Formulations that Permit Chitosan Rehydration and Spontaneous Microparticle Dispersion in Coagulating Human Blood Plasma A clotting and chitosan particle dispersion test was carried out in a 96-well plate with 170 µL human citrated plasma (thawed from a frozen aliquot for 5 minutes at 37° C.), one 1.5 mm diameter scaffold cylinder cored or cut from a lyophilized scaffold, 10 µL 200 mM $CaCl_2$ and 5 µL glass microbeads (10 µm Spherocell borosilicate glass beads at 10 mg/mL in $ddH_2O$). The samples were incubated for 20 minutes to 1 hour at 37° C. to permit coagulation via the contact pathway and fibrin polymerization to take place. Fluorescent images of the RITC-chitosan particles dispersed in the hybrid plasma clot were taken with an inverted fluorescent microscope. Results: All samples coagulated and formed fibrin clots (FIG. 2A-2I). It was discovered that all low molecular mass 10 kDa chitosan formulations dispersed as microparticles in the plasma, with or without bulking agents, and generated a hybrid chitosan microparticle-fibrin clot (FIG. 2E). The 85 kDa chitosan, however, failed to disperse in the plasma, when the chitosan solution is prepared at 80% protonation (FIG. 2F, Table 2). Some particle dispersion was obtained for a 85 kDa chitosan at 5 mg/ml containing an additional 10 mg/mL of N-acetyl glucosamine monomer, but not 10 mg/mL glucosamine monomer. It was then discovered that increasing the protonation level of 80 kDa chitosan to 98% (solution prior to freeze-drying pH 2.5 instead of pH 4.5) creates a freeze-dried scaffold that rehydrates slowly (FIG. 2D, formulation #33), and spontaneously forms a microparticle dispersion in human blood plasma (FIG. 2G). Addition of sucrose lyoprotectant to the freeze-dried scaffold interfered with microparticle dispersion of 85 kDa chitosan even at 98% protonation (FIG. 2H). Mixtures of high and low molecular weight chitosan freeze-dried at 98% protonation also dispersed (FIG. 2I). This experiment revealed that microparticle rehydration and dispersion can be controlled by adjusting chitosan protonation level and chitosan concentration, for chitosans with a wide range of molecular mass. It also revealed that the higher molecular weight formulation is optimally generated with no lyoprotectant.

Figure 3:
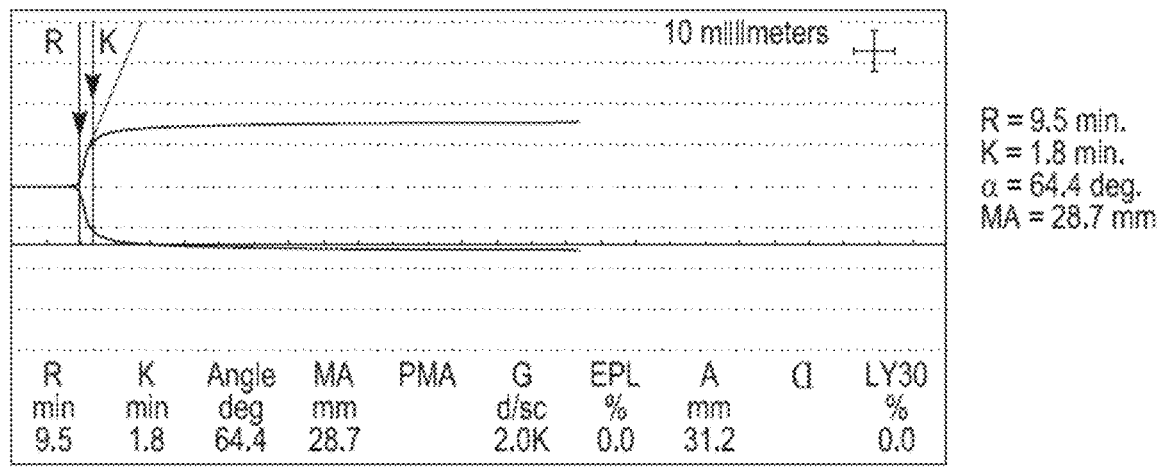
FIG. 3 is a thromboelastography assay of citrated human blood plasma and a chitosan scaffold formulation where the sample was clot-activated with calcium and glass beads immediately or after a delay of 1 to 60 minutes. The assay demonstrates rehydration kinetics of chitosan scaffolds that disperse as microparticles in human blood plasma. In this standardized thromboelastography (TEG) assay with recalcified citrated human blood plasma and glass beads added at time=0, clotting time (parameter R) starts at 7 to 10 minutes post-initiation followed by burst clot kinetics (3A). A chitosan freeze-dried scaffold (formulation #28: 10 kDa, 90% DDA, lyophilization method A, cored with a biopsy punch) was added to citrated plasma and the TEG assay initiated 1 minute later by adding $CaCl_2$ and glass beads. The coagulation time and development of clot tensile strength are slightly delayed (parameters R and K, 3B). It is known that the hydrated 90% DDA chitosan polymer has antithrombin activity. These data demonstrate that the scaffold has become partly rehydrated between the moment the scaffold is in contact with the blood plasma, and the moment of burst thrombin activation (3B). In a third test, the freeze-dried chitosan scaffold (formulation #28: 90% DDA, lyophilization method A) was allowed to rehydrate for 60 minutes after combining with citrated human plasma, followed by addition of clot activator ($CaCl_2$ and glass beads). The TEG trace shows a more delayed clot time (R) and greater suppression of burst coagulation (3C), compared to the same scaffold rehydrated for one minute (3B), due to full chitosan rehydration and association of negatively charged Gla domain-containing clotting factors with positively charged resolubilized chitosan microparticles. The combined data of (3B) and (3C) shows that the inhibitory effect is due to chitosan rehydration and not to the HCl component of the freeze-dried scaffold. In a fourth test, the freeze-dried chitosan scaffold (formulation #33, 85 kDa, 80.6% DDA, pH 2.5), was allowed to rehydrate for 60 minutes in citrated human blood plasma before adding clot activator at 60 minutes (3D). A delay in clotting time and fibrin assembly by the chitosan scaffold is observed, showing that the 85 kDa chitosan has rehydrated prior to thrombin activation. This experiment confirms that the chitosan scaffold has fully rehydrated and formed microparticles that bio-interface with coagulation factors. These data also demonstrate that specific chitosan formulations described herein undergo controlled rehydration that occurs during an interval between 1 and 60 minutes after contact with blood plasma.
Figure 3:
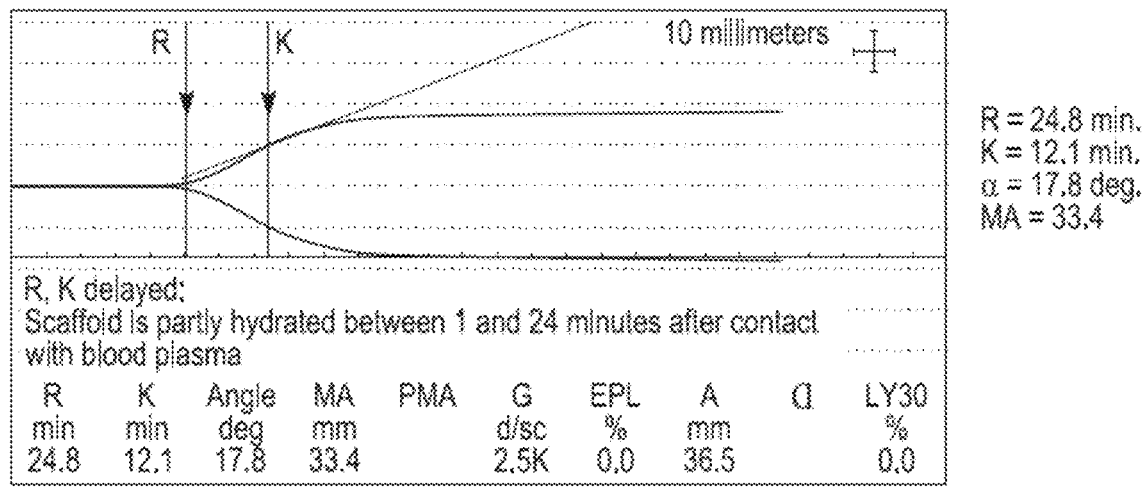
Figure 3:
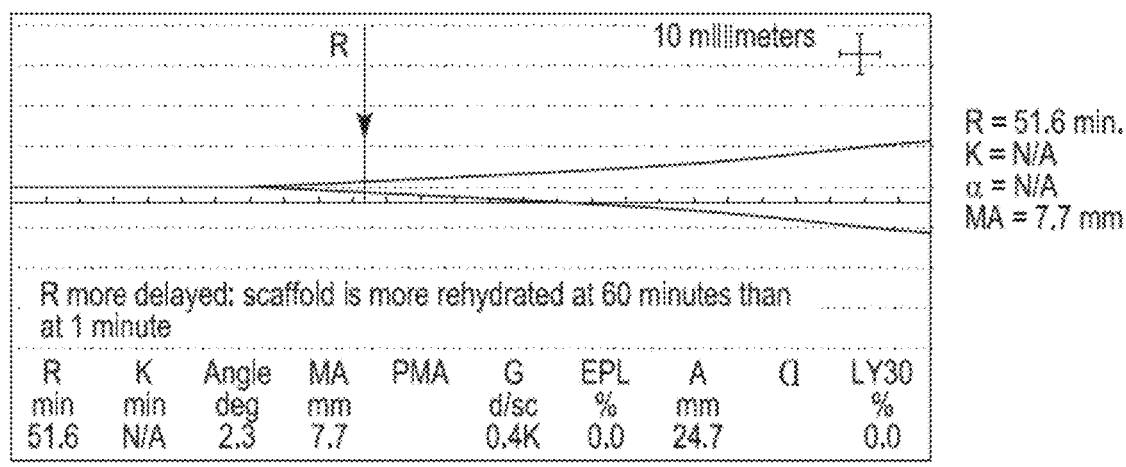
Figure 3:
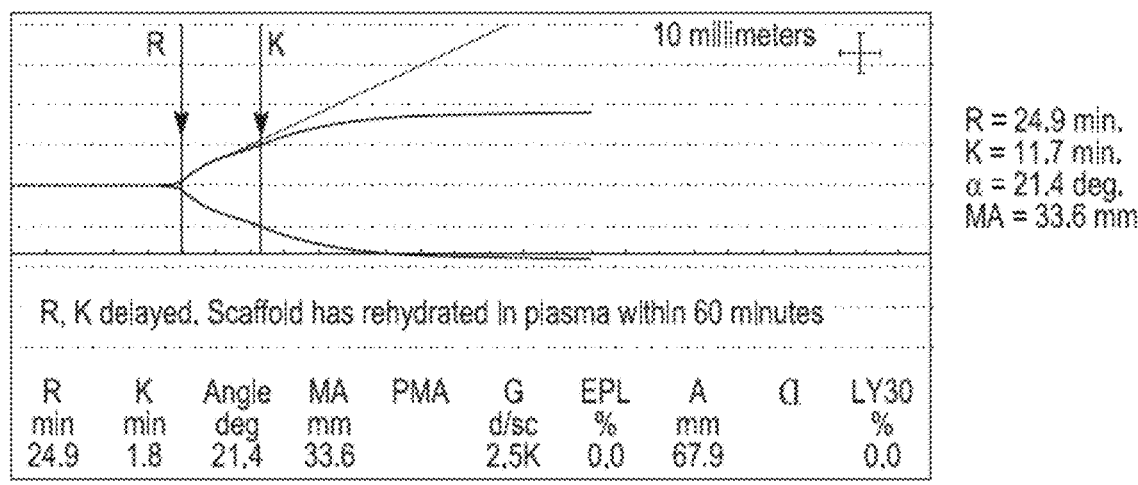

FIG. 3 shows that freeze-dried chitosan scaffold generated using lyophilization method (A) rehydrates slowly in human blood plasma and bio-interfaces as microparticles complexed through electrostatic complexes with negatively charged clotting factor enzymes, which results in delayed coagulation and lower clot tensile strength (FIGS. 3B, 3C & 3D), compared to plasma-alone (FIG. 3A). Altogether these data reveal formulations and a method for generating freeze-dried chitosan scaffolds that rehydrate in blood plasma, spontaneously disperse as microparticles, and interface with blood proteins.

The results of experiments 1 and 2 are shown in Tables 1 and 2, and are summarized as follows:

Formulations that passed the handling test (rigid cake, can be cored, Tables 1-3), rehydration test (category "R" in Tables 1-3) and microparticle dispersion test (category "D", Tables 1-3) required lyophilization method (A), and included ultra-low molecular weight chitosan-HCl (10 kDa, pH 4.5 to pH 5.5) with 5 to 10 mg/mL chitosan-HCl, or 2.4 to 5 mg/mL chitosan and 10 to 50 mg/ml bulking agent, and samples with medium molecular mass chitosan-HCl (~85 kDa, pH 2.5, <60 mOsm) at 10 or 20 mg/mL, and 85 kDa chitosan 5 mg/mL pH 4.5 with 10 mg/mL N-acetyl glucosamine bulking agent, or mixtures of 85 kDa and 10 kDa chitosan (1:1 v/v, pH 4.5).

Formulations that failed the handling test include all samples lyophilized by method (B), and samples lyophilized by method (A) with 10 kDa or 85 kDa chitosan-HCl (pH 2.5 to 5.5) at less than 5 mg/mL, 85 kDa or 150 kDa chitosan 2.5 to 10 mg/mL pH 4.5, and 85 kDa or 150 kDa chitosan 5 mg/mL with lyoprotectant (sucrose or glucosamine-HCl, 10 mg/mL).

Example 3

Figure 4:
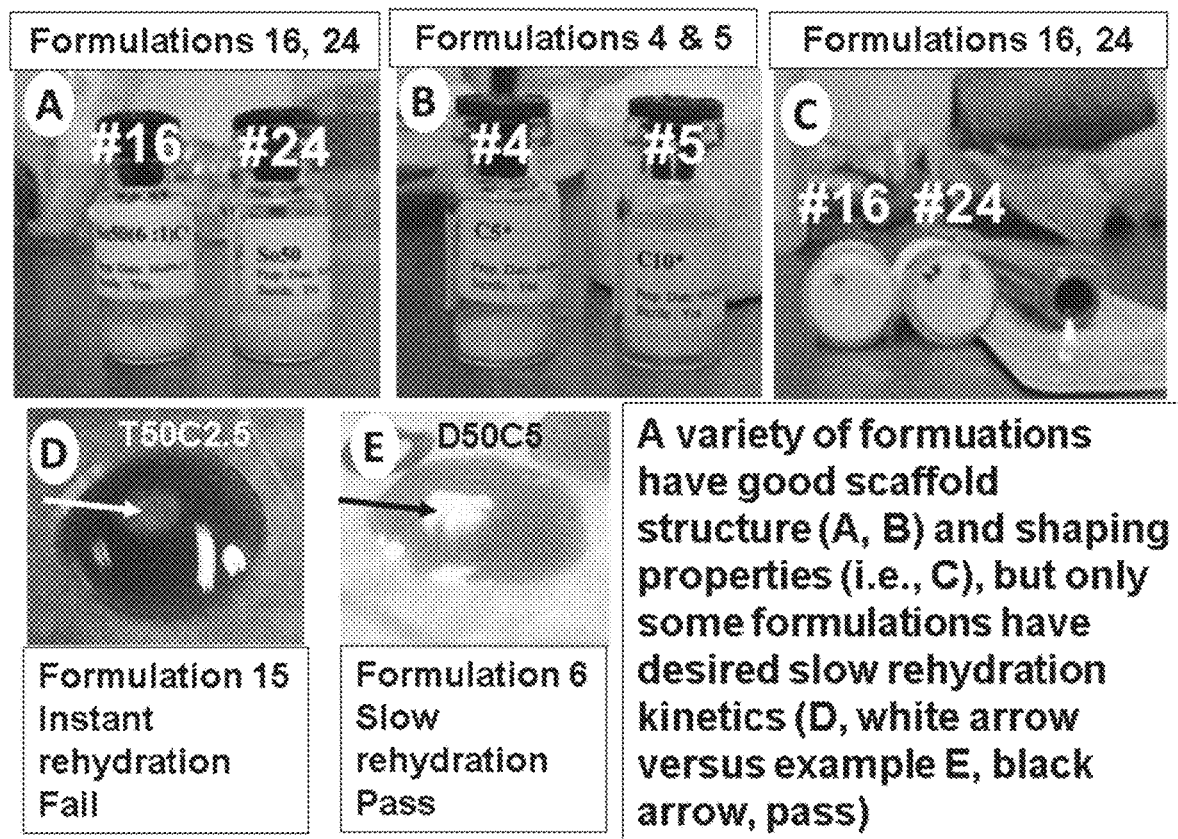
FIG. 4 is a comparison of lyophilized chitosan scaffold implants used in a surgical procedure and demonstrating controlled rehydration in a bleeding bone defect of only selected formulations among a variety of formulations with good handling properties. Freeze-dried chitosan scaffold implants were formed using lyophilization method A (4A, 4B, and 4C), with chitosan (80% DDA, 10K chitosan-HCl, pH 4.5-5.5), without or with lyoprotectant, several different kinds), and lyoprotectant-only (different kinds). Handling properties and ability to core a cylindrical scaffold with a biopsy punch were documented at surgery for all of the tested scaffolds (4C), however only selected scaffolds dissolved with the desired slow rehydration kinetics. (4D) shows an example where the chitosan scaffold with lyoprotectant dissolves instantly while (4E), and (4F to 4I) show in a video sequence in which a distinct chitosan scaffold with dextran-5 instead of lyoprotectant dissolves slowly in contact with whole blood either on a histology slide (4E) or in the bleeding microdrill hole (4G-4I). (4J) shows slow in vivo rehydration of an implant of freeze-dried chitosan with no lyoprotectant (formulation #5) in a bleeding microdrill hole, prior to in situ microparticle dispersion and blood coagulation. (4K) and (4L) show in a video sequence the instant rehydration of a freeze-dried formulation of chitosan and lyoprotectant (formulation #26) leading to formulation rejection due to poor control over implant delivery.
Figure 4:
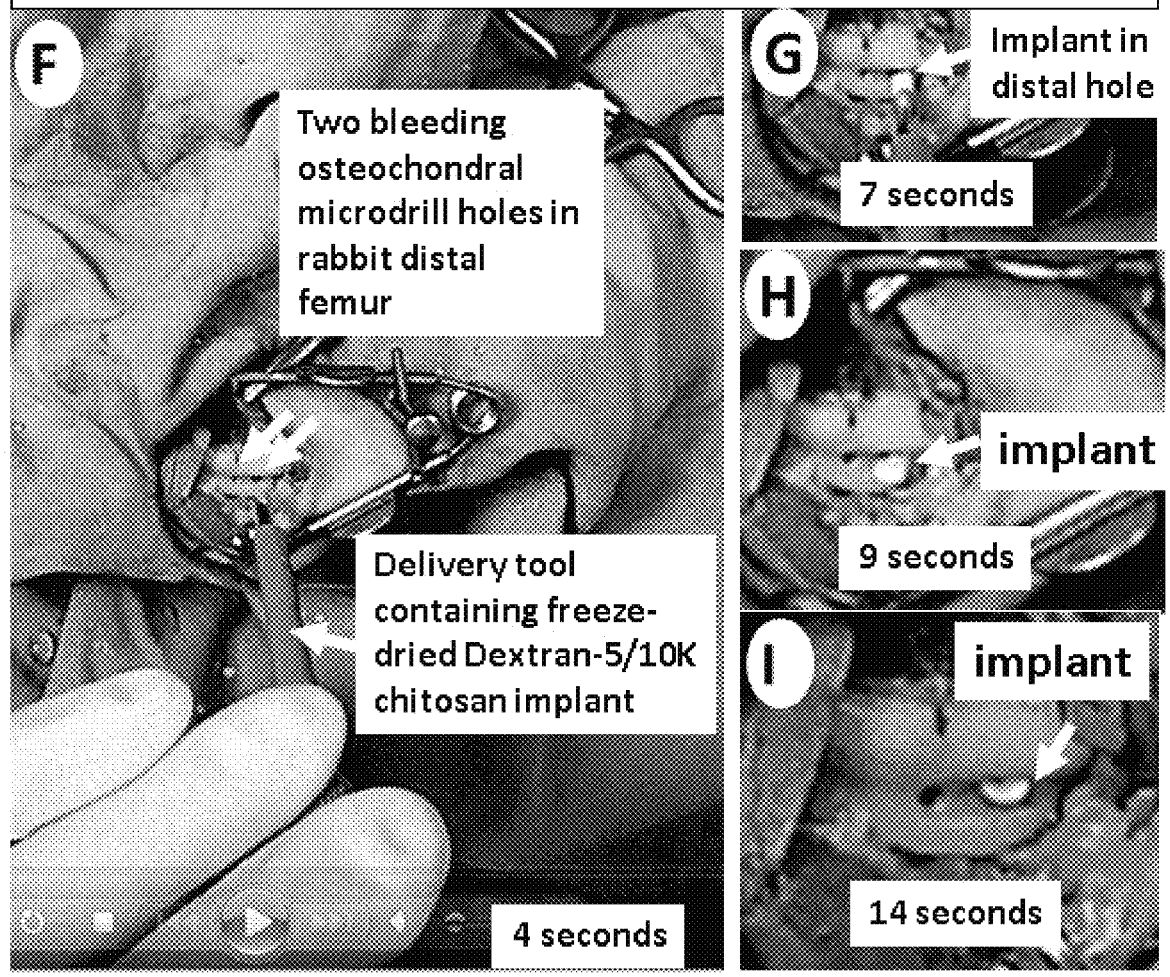
Figure 4:
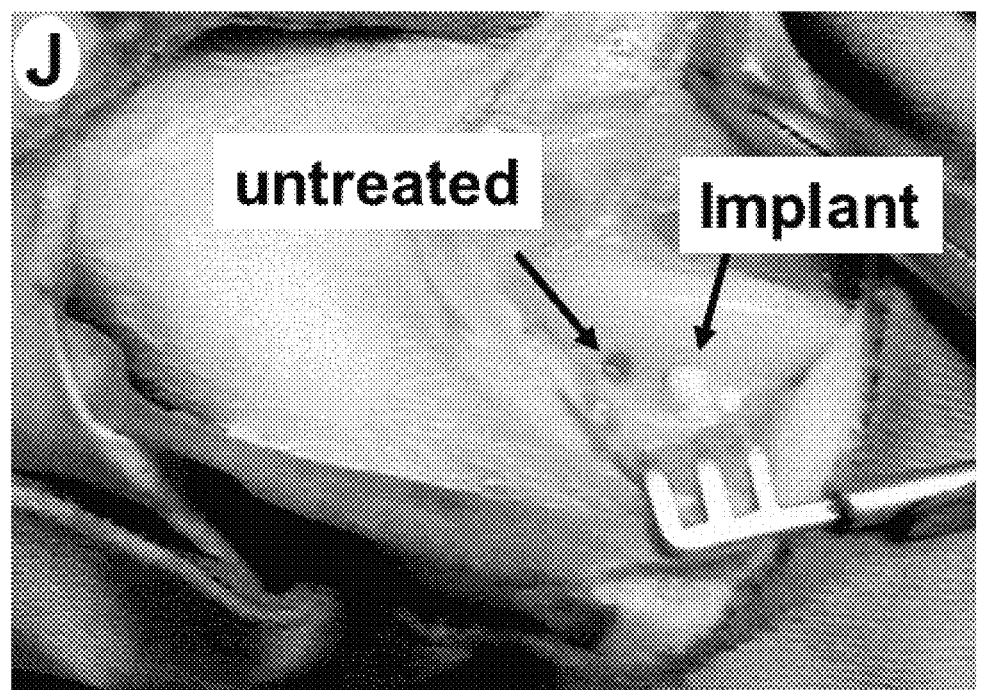
Figure 4:
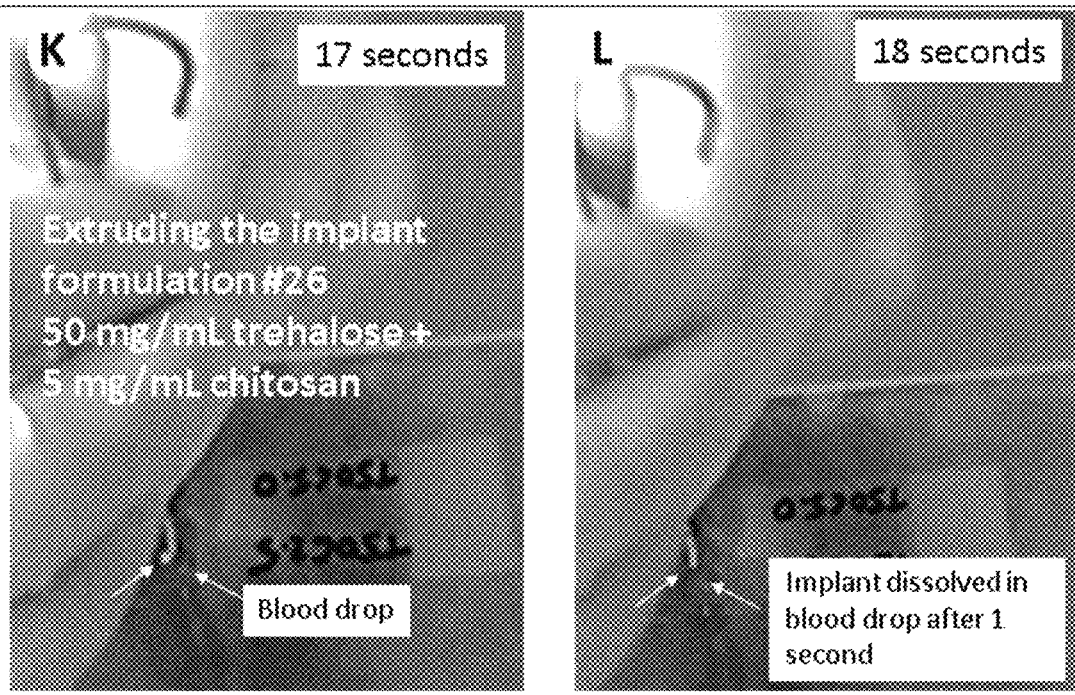

In Vivo Proof-of-Concept in a Rabbit Model to Demonstrate that Freeze-Dried Chitosan Formulations can be Implanted in Bleeding Defects and Stimulate Anabolic Wound Repair Processes In a pilot rabbit study (3 week endpoint to observe in situ angiogenesis and bone remodeling), sterile freeze-dried chitosan implants were created (Table 4), cored with a biopsy punch and directly implanted into 1.5 mm diameter, 2 mm deep drill holes created in a 4×5 mm full-thickness cartilage defect in the rabbit knee trochlea. Sterile chitosan scaffold cakes and lyoprotectant-only cakes were generated by controlled lyophilization method (A). Cylindrically-shaped implants were created intra-operatively using a biopsy punch to core 1.5 mm diameter cylinders from the solid cake (FIG. 4). The proximal 1.5 mm microdrill defect created in the rabbit knee trochlea was treated with lyoprotectant-only implant, while the distal 1.5 mm microdrill defect was treated with lyoprotectant+chitosan. In one rabbit knee, both drill holes were untreated (drill-only) and in another rabbit knee, both drill holes were treated with 5 mg/mL chitosan-HCl (pH 5.5) or 10 mg/mL chitosan-HCl (pH 5.5) implant (no lyoprotectant).

TABLE 4

Lyophilized scaffolds delivered directly to bleeding defects to test their capacity to elicit angiogeniesis and bone remodeling.

| Rabbit | condition proximal hole | distal hole | repair days |
|---|---|---|---|
| 1 left knee | Drill-only | Drill-only | 2 |
| 1 right knee | Drill-only | Drill-only | 2 |
| 2 left knee | 50 mg/mL sucrose (formulation #22) | 50 mg/mL sucrose, 2.4 mg/mL chitosan-HCl 10 kDa pH 5.5, 81.9% DDA, trace RITC-chitosan 10 kDa, 81.9% DDA (formulation #14) | 21 |
| 2 right knee | 5 mg/mL chitosan 10 kDa, 81.9% DDA, trace RITC-chitosan 10 kDa, 81.9% DDA (formulation #4) | 10 mg/mL chitosan-HCl 10 kDa, 81.9% DDA pH 5.5, trace RITC-chitosan 10 kDa, 81.9% DDA (formulation #5) | 21 |
| 3 left knee | 50 mg/mL sorbitol (formulation #23) | 50 mg/mL sorbitol, 2.4 mg/mL chitosan-HCl 10 kDa pH 5.5, 81.9% DDA, trace RITC-chitosan 10 kDa, 81.9% DDA (formulation #16) | 21 |
| 3 right knee | Drill-only | Drill-only | 21 |
| 4 left knee | 50 mg/mL trehalose (formulation #23A) | 50 mg/mL trehalose, 5 mg/mL chitosan-HCl pH 5.5, 10 kDa, 81.9% DDA, trace RITC-chitosan 10 kDa, 81.9% DDA (formulation #15) | 21 |
| 4 right knee | 50 mg/mL dextran-5 (formulation #7) | 50 mg/mL dextran-5, 5 mg/mL chitosan-HCl pH 5.5, 10 kDa, 81.9% DDA, trace RITC-chitosan 10 kDa, 81.9% DDA (formulation #6) | 21 |

Results: In vivo handling properties: It was discovered that some formulations dissolved too rapidly while other formulations dissolved in situ with desired slow and controlled kinetics. Chitosan+50 mg/mL sucrose, chitosan+50 mg/mL sorbitol, and chitosan+50 mg/mL trehalose dissolved instantly upon contact with blood and could not be deposited in a controlled fashion in the bleeding drill hole (see FIGS. 4D, 4K & 4F). Chitosan-alone (5 mg/mL or 10 mg/mL), could be deposited into the bleeding defect and dissolved during 1 to 2 minutes (FIG. 4G). This slow in situ dissolving was preferred to the very rapid-dissolving formulations with lyoprotectant, because it was not possible to press-fit the very rapidly dissolving formulations in the hole or guide the chitosan to be deposited in the bone drill hole. Chitosan-Dextran-5 (with 5 mg/mL chitosan) and Dextran-5 (50 mg/m L) also showed good handling properties and dissolved in situ with an extended time (around 1 minute, FIG. 4F-4I). The property of slow in situ rehydration was used to determine pass-fail criteria (see criterion "S", Table 1 above).

Figure 5:
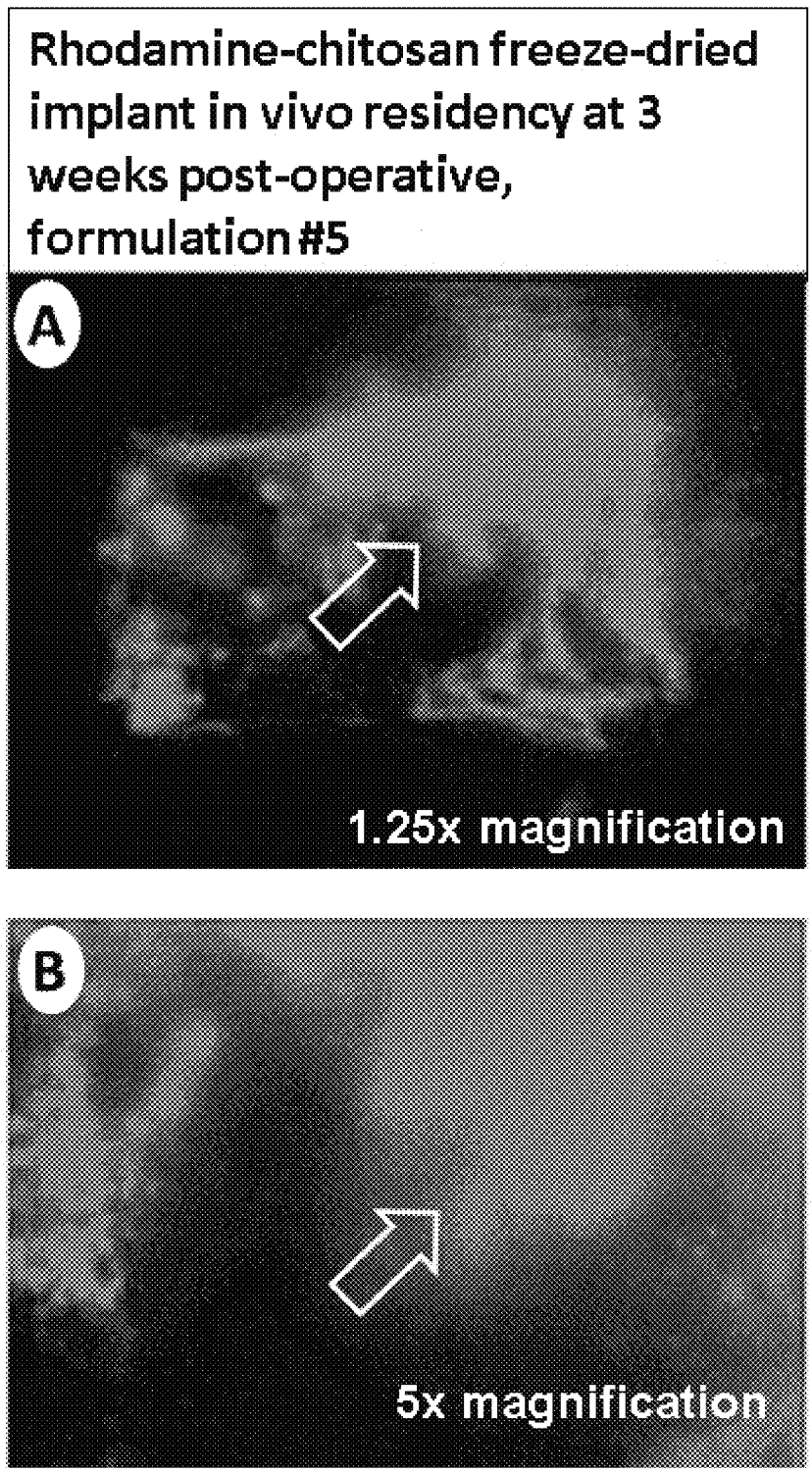
FIG. 5 shows a lyophilized polysaccharide scaffold implant applied to a bleeding osteochondral defect in rabbits is still partly resident at 21 days post-operative (5A), and that selected formulations have elicited therapeutic responses including the local accumulation of macrophages and alternatively activated arginase-1+ macrophages and angiogenic blood vessels 5C-5H). Freeze-dried chitosan scaffold implants are retained up to 21 days post-operative in treated rabbit trochlear knee cartilage defects, as shown in 5A & 5B where the white hue represents the red epifluorescent signal of resident rhodamine-chitosan in the rectangular full-thickness cartilage defect; the implants also attract alternatively activated arginase-1+ macrophages (5C) and macrophages (RAM-11+, 5D), and elicit angiogenic blood vessels (5E-5F) in granulation tissues formed in freeze-dried chitosan scaffold-treated microdrill holes. The formulations that elicited angiogenesis in this figure are 80% DDA chitosan, 10 kDa, dissolved in dilute HCl at 5 mg/mL or 10 mg/mL followed by a controlled freeze-dry process (formulations #4 and #5). 5G and 5H show that the lyophilized polysaccharide scaffold implant Dextran-5 alone, and combined Dextran-5 and chitosan, respectively, applied to a bleeding osteochondral defect in rabbits stimulates at day 21 post-operative the formation of an angiogenic granulation tissue in the healing drill hole.
Figure 5:
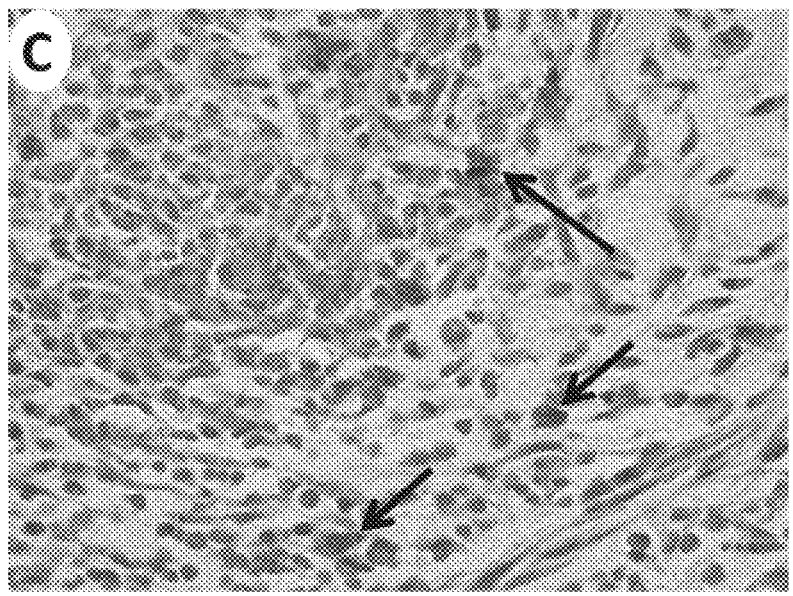
Figure 5:
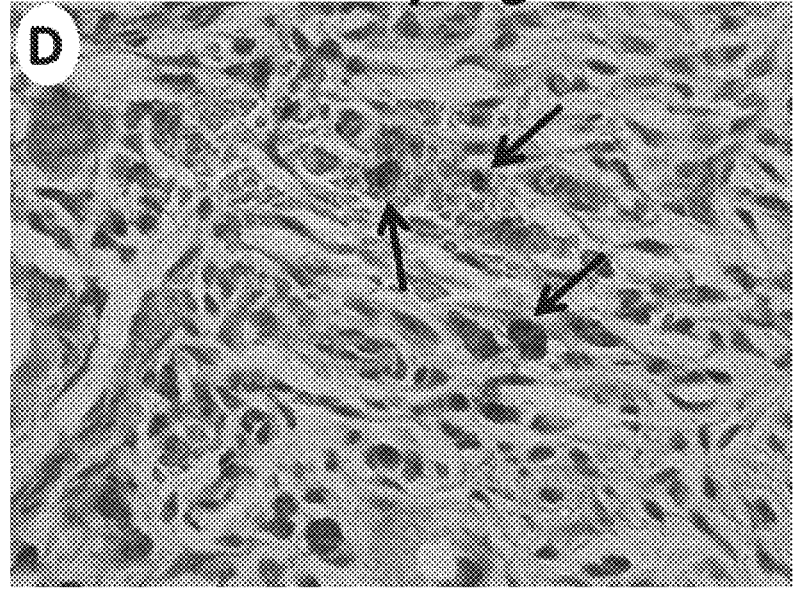
Figure 5:
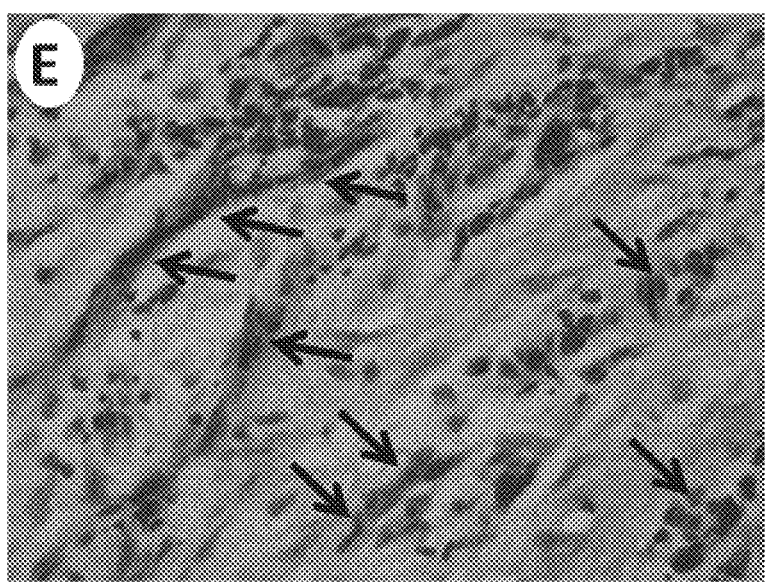
Figure 5:
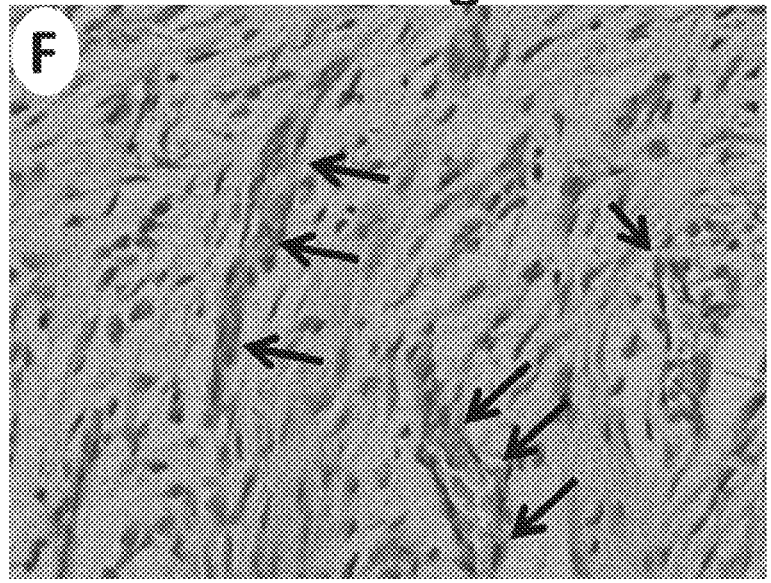
Figure 5:
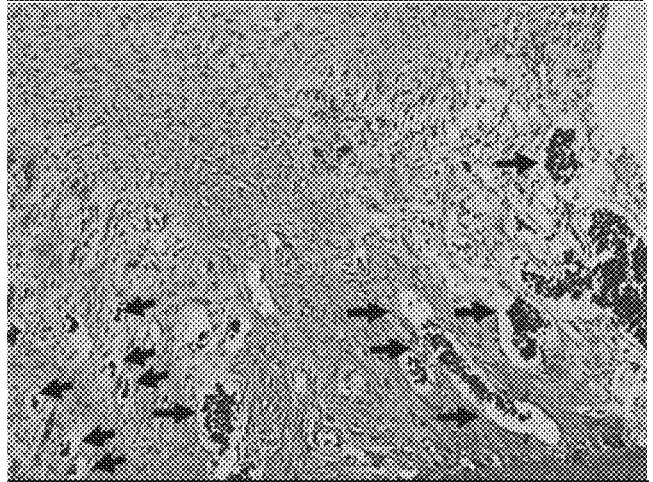
Figure 5:
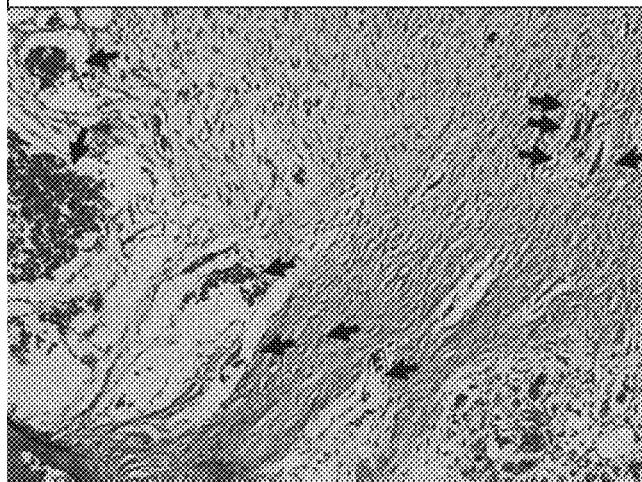
Figure 6:
FIG. 6 is a macroscopic and histological comparison of the repair response in drilled rabbit cartilage defects treated or not with chitosan scaffold with controlled rehydration. Polysaccharide freeze-dried scaffold implants elicited angiogenesis and suppressed fibrocartilage formation in rabbit osteochondral defects at 21 days post-operative while drill-only elicits fibrocartilage. Fibrocartilage is shown by the presence of a macroscopic white tissue (6A), containing glycosaminoglycan (6C) and collagen type I (fibrotic tissue) near the articular surface (6D). By comparison, at 21 days post-operative in the contraleral knee, drill holes treated with freeze-dried chitosan implant (lyophilization method A, 10 kDa chitosan-HCl pH 5.5, 5 mg/mL or 10 mg/mL proximal and distal holes respectively), are filled with angiogenic tissues as shown by the dark grey macroscopic appearance in the drill hole (6B), representing the reddish hue of highly vascularized granulation tissue (6E) and lack of collagen type I deposition or fibrosis (6E). The drill-only defects were filled at 21 days post-operative with a poorly integrated fibrocartilage repair tissue (6C). The 10K chitosan-only and dextran-5 implants elicited local angiogenesis and suppressed fibrocartilage synthesis (6D, 6F). Arrows in (6E) indicate individual blood vessels.
Figure 6:
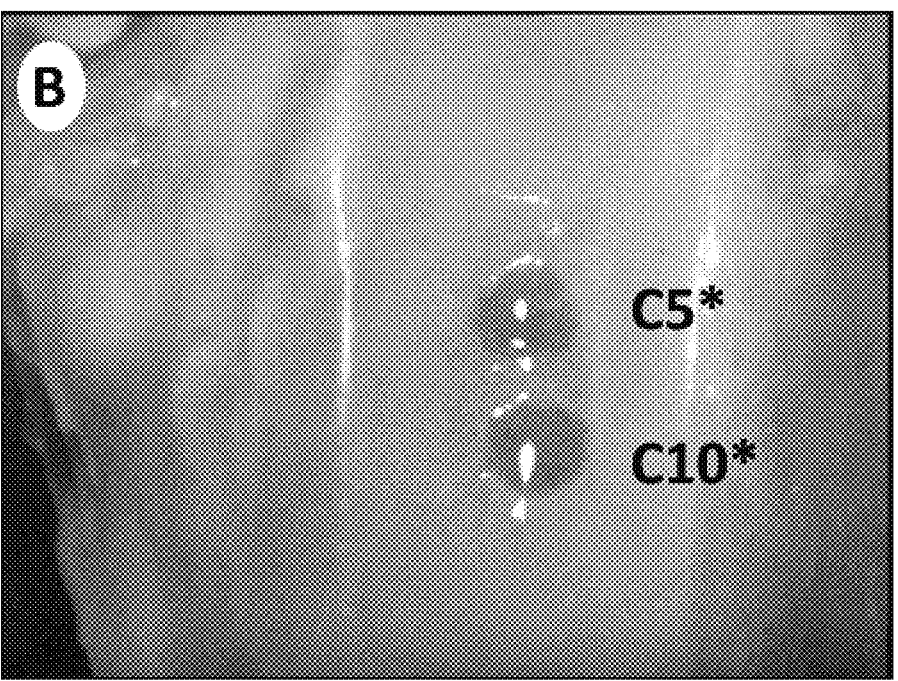
Figure 6:
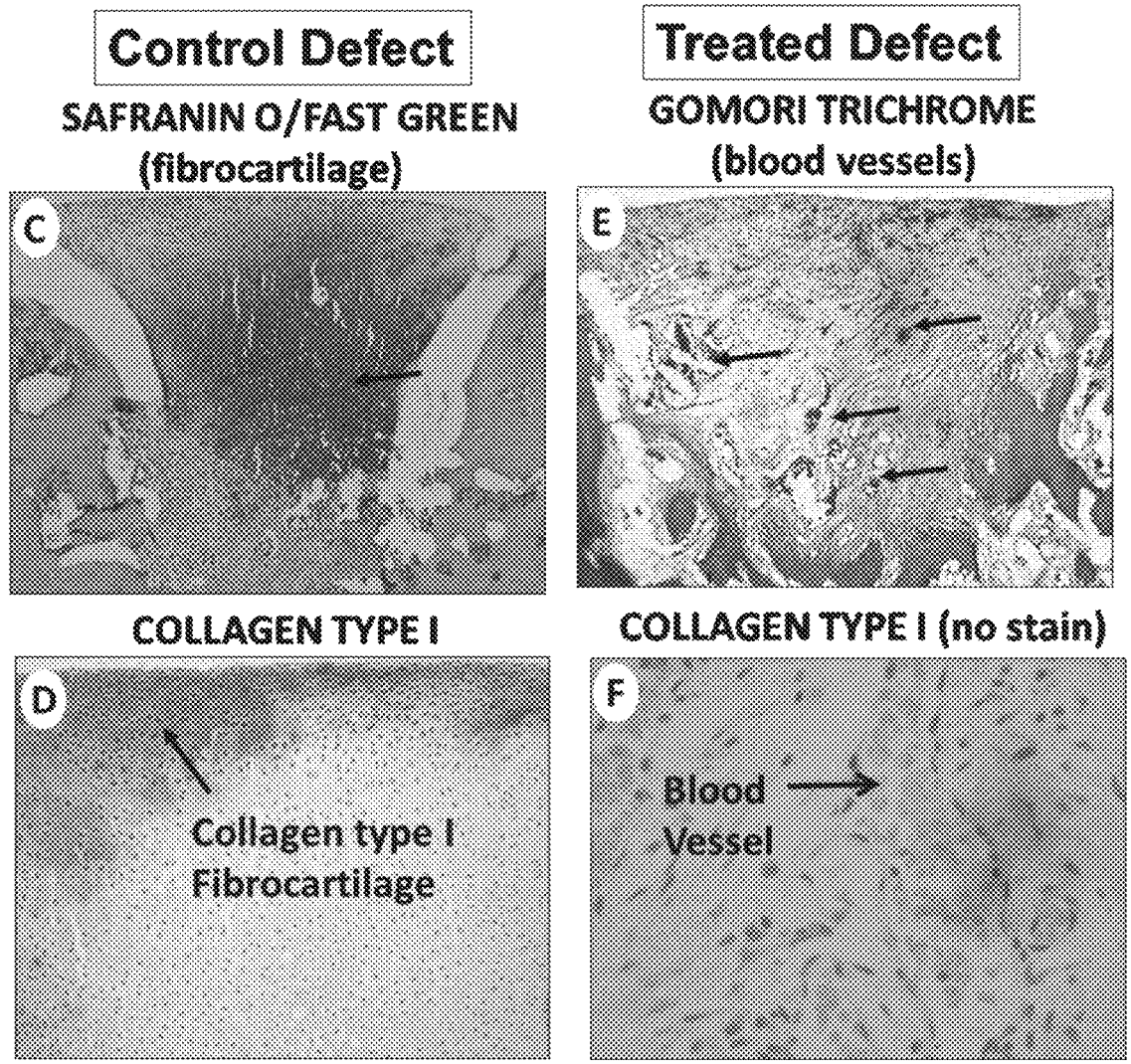
Figure 7:
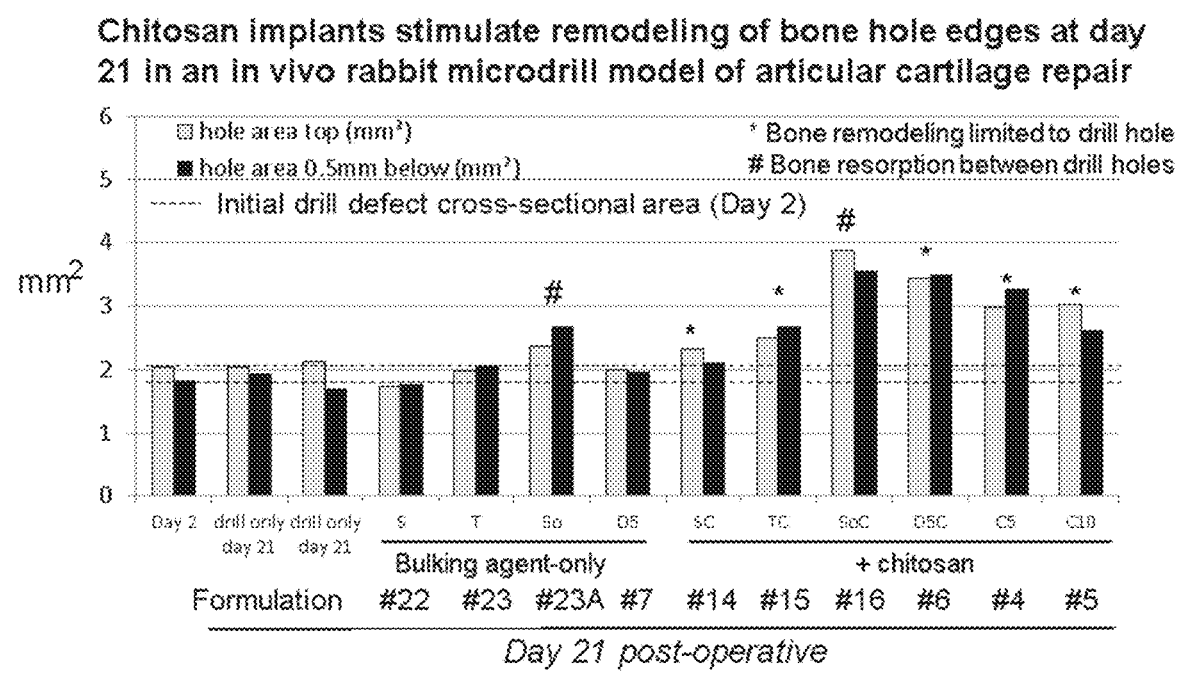
FIG. 7 is a comparison of the ability of lyophilized chitosan-containing implants versus dextran-5 and lyoprotectant-only to stimulate bone remodeling in an in-vivo rabbit model for cartilage repair. The graph shows the drill hole cross-sectional area at the top (grey bar) and at 0.5 mm below the top (black bar) of a microdrill hole at 21 days post-operative, as measured from the hole circumferences in 2D calibrated micro-computed tomography coronal images of the healing distal femur ends. The data show that lyophilized polysaccharide scaffold implants can be designed to stimulate remodeling at the edge of the bone hole by addition of chitosan (but not dextran-5 and not by sucrose or trehalose lyoprotectant-only). Dextran-5 (50 mg/mL in water, formulation #7, lyophilization method A) elicited angiogenesis (as shown in FIG. 5G) without inducing bone resorption. Bone remodeling is demonstrated by widening of the drill hole average diameter at the top of the hole (light grey bar) and 0.5 mm below the top (black bar), The scaffolds that induced bone remodeling have a hole cross-sectional area greater than 2 mm (above the dotted line). It is noted that implants containing sorbitol (conditions "So" and "SoC") showed catabolic bone resorption of bone bridging the drill holes, an undesired effect (symbol # in FIG. 7, formulations #23A and #16). The scaffolds that induced bone remodeling are highlighted by the symbol (*). All chitosan implants in this experiment contained 10 kDa 80% DDA and protonation level 80% pH 4.5 with and without bulking agent and were sterilized prior to lyophilization by method A (see Tables 1 and 3). Symbols: S=50 mg/mL sucrose; CS=2.4 mg/mL chitosan+50 mg/mL sucrose; So=50 mg/mL sorbitol; SoC=2.4 mg/mL chitosan+ 50 mg/mL sorbitol; T=50 mg/mL Trehalose; TC=5 mg/mL chitosan+50 mg/mL Trehalose; D5=50 mg/mL dextran-5; D5C=5 mg/mL chitosan+50 mg/mL Dextran-5; C5=5 mg/mL chitosan-HCl; 010=10 mg/mL chitosan-HCl.

Biological response: The chitosan implants were retained in the defects, as shown by the presence of residual rhodamine-chitosan tracer in the 3 week repair tissues (FIG. 5A-B). The chitosan particles have a favorable effect in attracting macrophages to the granulation tissues (FIG. 5C, 5D). It was discovered that all formulations containing sugar or polysaccharide suppressed fibrocartilage formation at 3 weeks post-operative. This is a therapeutic effect because rapid fibrocartilage formation is known to impede chondroinduction and cartilage regeneration at later timepoints (Mathieu C, Chevrier A, Lascau-Coman V, Rivard G E, Hoemann C D: Stereological analysis of subchondral angiogenesis induced by chitosan and coagulation factors in microdrilled articular cartilage defects, Osteoarthritis Cartilage 2013, 21:849-859; Chevrier A, Hoemann C D, Sun J, Buschmann M D: Temporal and spatial modulation of chondrogenic foci in subchondral microdrill holes by chitosan-glycerol phosphate/blood implants, Osteoarthritis Cartilage 2011, 19:136-144). Selected chitosan formulations elicited angiogenesis at 3 weeks post-operative (arrows, FIG. 5E, 5F). Angiogenesis was determined by the macroscopic reddish hue of the granulation tissue represented by the grey appearance of the drill holes (FIG. 6B), and by the histological appearance of blood vessels filled with erythrocytes in Gomori-stained histology sections (represented by dark grey structures, FIG. 6E, 6F), and used as a pass-fail criteria (Table 1). Holes treated with 10 kDa chitosan-HCl alone (without lyoprotectant) showed the strongest angiogenic response at 3 weeks (FIG. 5E, 5F, 6B, 6E, 6F). The repair response was highly similar to the angiogenic response previously elicited by in situ-solidified chitosan-GP/blood implant (Mathieu C, Chevrier A, Lascau-Coman V, Rivard G E, Hoemann C D: Stereological analysis of subchondral angiogenesis induced by chitosan and coagulation factors in microdrilled articular cartilage defects, Osteoarthritis Cartilage 2013, 21:849-859). The microdrill hole treated with dextran-5-only also showed an angiogenic response (Table 1). Dextran-5 is a 5 kDa polymeric oligosaccharide. Several defects treated with lyoprotectant-alone showed signs of foreign body giant (FBG) cell formation (trehalose, sorbitol: potentially due to the crystals). No foreign body giant cells were observed in chitosan-only treated bone drill holes. The influence of FBG cell formation in granulation tissue on connective tissue repair is unknown and may not detract from repair. Holes treated with chitosan implant showed accumulation of macrophages and alternatively activated arginase-1+ macrophages (FIGS. 5C & 5D). Bone remodeling was scored by an increased microdrill bone hole diameter in 3D reconstructed micro-computed tomography scans, as a consequence of osteoclast-mediated bone resorption. All holes treated with chitosan showed evidence of bone remodeling at the hole edge (FIG. 7). Only sorbitol showed bone remodeling accompanied by pathological bone resorption of bone bridging the drill holes (FIG. 7, conditions So and SoC, #). This experiment revealed that freeze-dried chitosan-only 10 kDa implants inserted directly into bleeding osteochondral defects reside in situ and have therapeutic anabolic effects on wound remodeling and repair.

Example 4

In Vivo Proof-of-Concept in a Skeletally Aged Sheep Model: Lyophilized In Situ Chitosan Implants with High Molecular Weight Chitosan have a Therapeutic Effect Two of the freeze-dried chitosan formulations were identified with therapeutic angiogenic effects in a rabbit model using ultra-low molecular mass chitosan (formulations C5* and 010*, Table 5). However osteochondral repair in large animals is delayed compared to rabbit (Bell A D, Lascau-Coman V, Sun J, Chen G, Lowerison M W, Hurtig M B, Hoemann C D: Bone-Induced Chondroinduction in Sheep Jamshidi Biopsy Defects with and without Treatment by Subchondral Chitosan-Blood Implant: 1-Day, 3-Week, and 3-Month Repair, Cartilage 2013, 4:131-143; Bell A, Hurtig M, Rivard G E, Hoemann, CD. Effect of bone marrow surgical approach and rapidly degrading presolidified subchondral chitosan/blood implant on resurfacing of chondral defects in a sheep model. Transactions OARSI, April 2014, Paris), and requires a higher molecular weight chitosan to elicit chondrogenesis in sheep defects using presolidified chitosan-NaCl/blood implants (Bell A D, Lascau-Coman V, Sun J, Chen G, Lowerison M W, Hurtig M B, Hoemann C D: Bone-Induced Chondroinduction in Sheep Jamshidi Biopsy Defects with and without Treatment by Subchondral Chitosan-Blood Implant: 1-Day, 3-Week, and 3-Month Repair, Cartilage 2013, 4:131-143; Bell A, Hurtig M, Rivard G E, Hoemann, C D. Effect of bone marrow surgical approach and rapidly degrading presolidified subchondral chitosan/blood implant on resurfacing of chondral defects in a sheep model. Transactions OARSI, April 2014, Paris). These data suggested that an in vivo chitosan implant with a slower degradation rate is preferred for large animals to accommodate the slower osteochondral repair progression compared to small animals or to accommodate the denser subchondral bone requiring longer remodeling times. Therefore, 3 freeze-dried chitosan formulations were evaluated with higher molecular weight chitosan (85 kDa), at 3 different concentrations and 98% protonation prior to freeze-drying using Lyophilization method (A) (Table 5). Some implants were freeze-dried with rhodamine-chitosan tracer of matching molecular mass to document in vivo clearance. The study design used skeletally aged sheep, 9 years old, with N=2 sheep (day 1), N=5 sheep (3 months), and N=5 sheep (9 months). Using a small arthrotomy approach, one knee at a time, a medial femoral condyle full-thickness cartilage defect was created with a curette 10×10 mm, and then 3 vertical rows of ~4 mm deep micro-drilled holes were created (1.5 mm drill burr diameter, 11 holes total). Each vertical row of drill holes in one knee was treated with one formulation of distinct chitosan concentration by inserting a cylinder of lyophilized implant, with a tweezers into each bleeding hole (FIG. 8B). The contralateral knee drill holes were created in the same fashion and left to bleed as surgery-only control defects (FIG. 8C).

TABLE 5

Freeze-dried chitosan formulations tested in vivo in small and large animal cartilage repair models.

| Formulation Name (# from Tables 1 & 2) | Chitosan solution name | Mn (g/mol) | Mw (g/mol) | PDI | HMW (%) | pH prior to lyophilization (litmus paper) | Osmolality prior to lyophilization (mOsm) |
|---|---|---|---|---|---|---|---|
| C5* (#4) | 10K03 (5 mg/mL) | 7,451 | 25,100 | 3.4 | 1.2% | 4.0-5.5 (80% protonation) | 68 |
| C10* (#5) | 10K03 (10 mg/mL) | 7,451 | 25,100 | 3.4 | 1.2% | 4.0-5.5 (80% protonation) | 68 |
| A (#29) | 80M8 (5 mg/mL) | 52,590 | 85,380 | 1.6 | — | 2.5-3.0 (98% protonation) | 10 |
| B§ (#33) | 80M8 (10 mg/mL) | 52,590 | 85,380 | 1.6 | — | 2.5-3.0 (98% protonation) | 25 |
| C§ (#34) | 80M8 (20 mg/mL) | 52,590 | 85,380 | 1.6 | — | 2.5-3.0 (98% protonation) | 46 |

*good handling and performance properties for treating defect drill holes in small joints;
§best handling and performance properties for treating large defect drill holes.
HMW: high molecular weight fraction.

Figure 8:
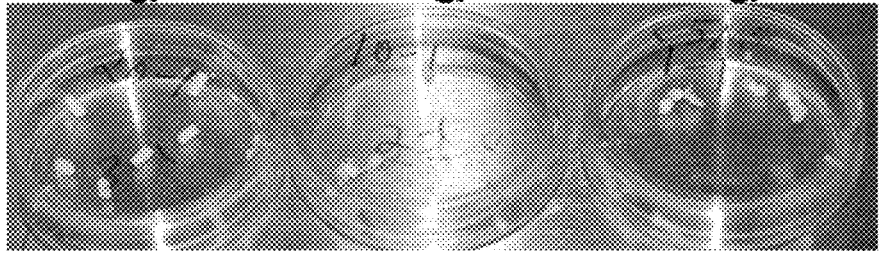
FIG. 8 is a comparison of lyophilized chitosan implants (formulations #29, #33, and #34) after coring from a rigid cake and implanting in drilled sheep osteochondral holes. These data show that freeze-dried chitosan implants (8A, 85 kDa chitosan-HCl, about pH 2.5, at 5, 10, and 20 mg/mL, formulations #29, #33, and #34, respectively) can be cored from the rigid freeze-dried scaffold and implanted in drilled sheep osteochondral holes in a cartilage defect of the medial femoral condyle (8B, skeletally aged sheep). Bleeding microdrill holes without implant are shown in panel (8C). The average increase in surgery time due to implant treatment was 7 minutes which is considerably shorter compared to 15 minutes for pre-solidified chitosan/blood implant and 20 to 30 minutes for in situ-solidifying chitosan-GP/blood implant (8D). At 1 day post-operative, the data also show that the treated drill holes were filled with a hybrid blood clot at day 1 (8E, macroscopic appearance) containing chitosan scaffold in the holes as revealed by epifluorescence microscopy of rhodamine-chitosan tracer (white signal in macroscopic view, 8F).
Figure 8:
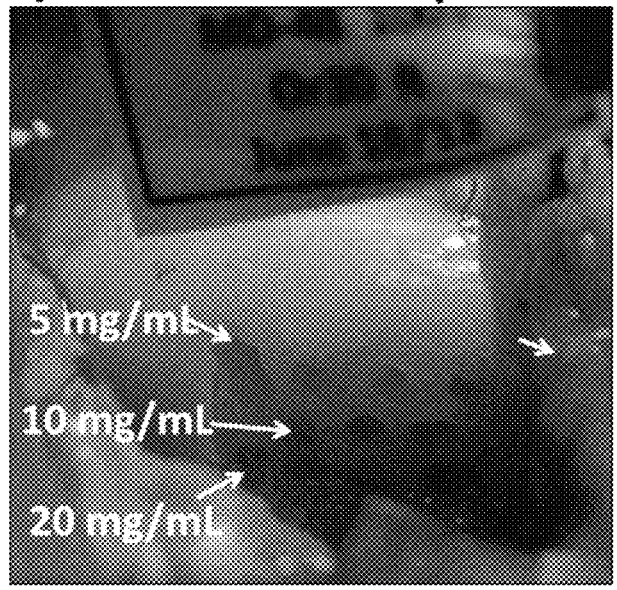
Figure 8:
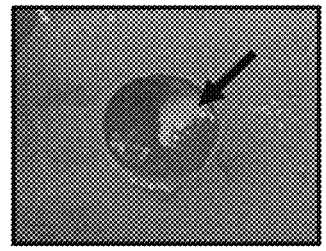
Figure 8:
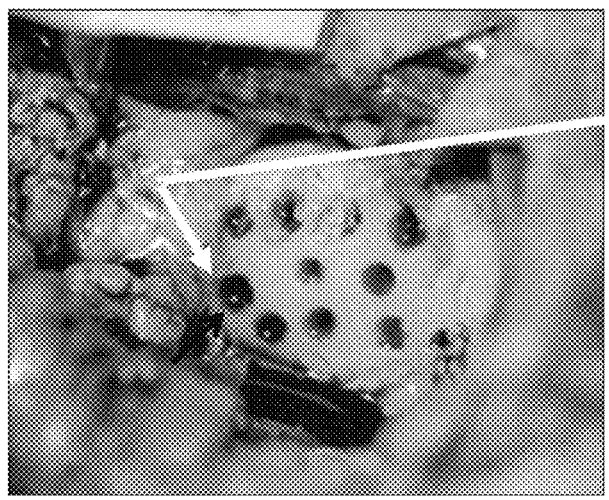
Figure 8:
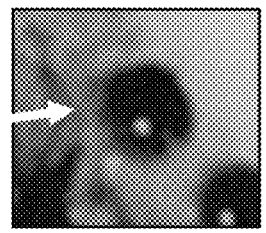
Figure 8:
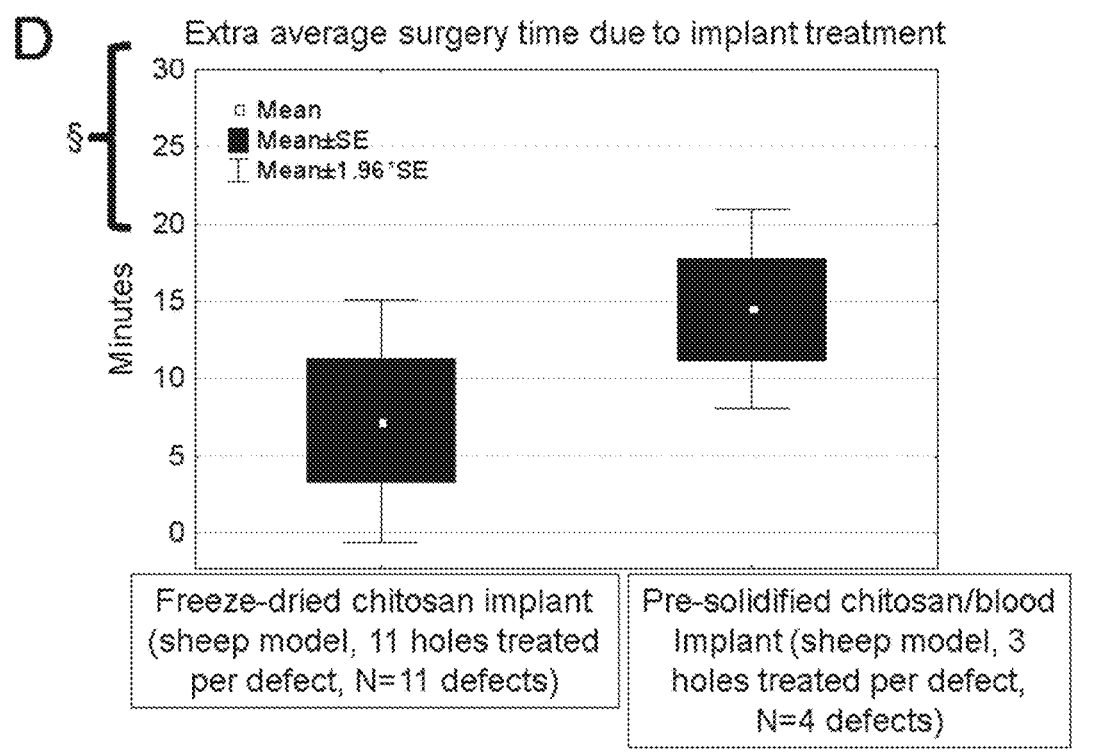
Figure 8:
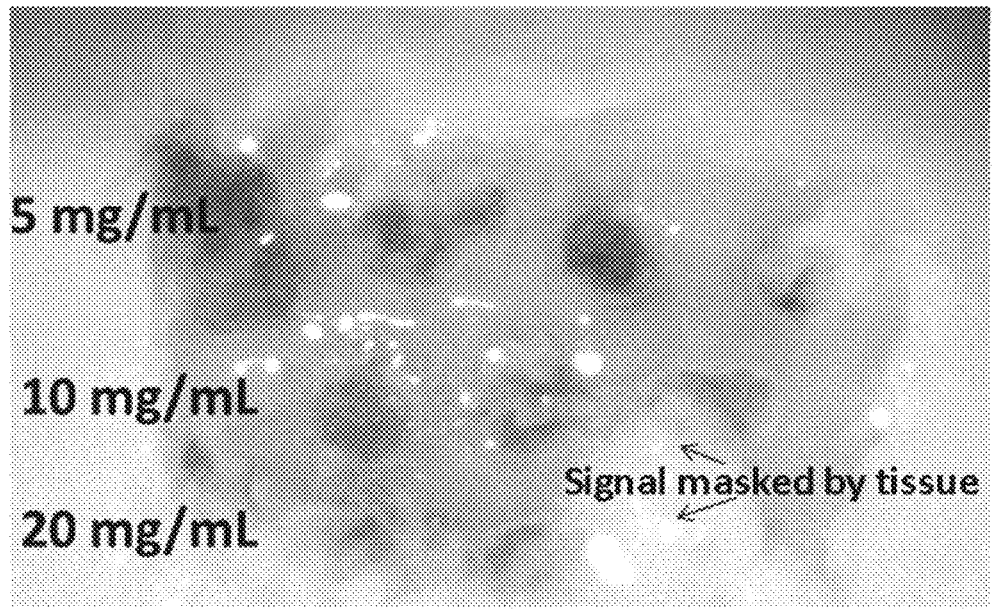
Figure 8:
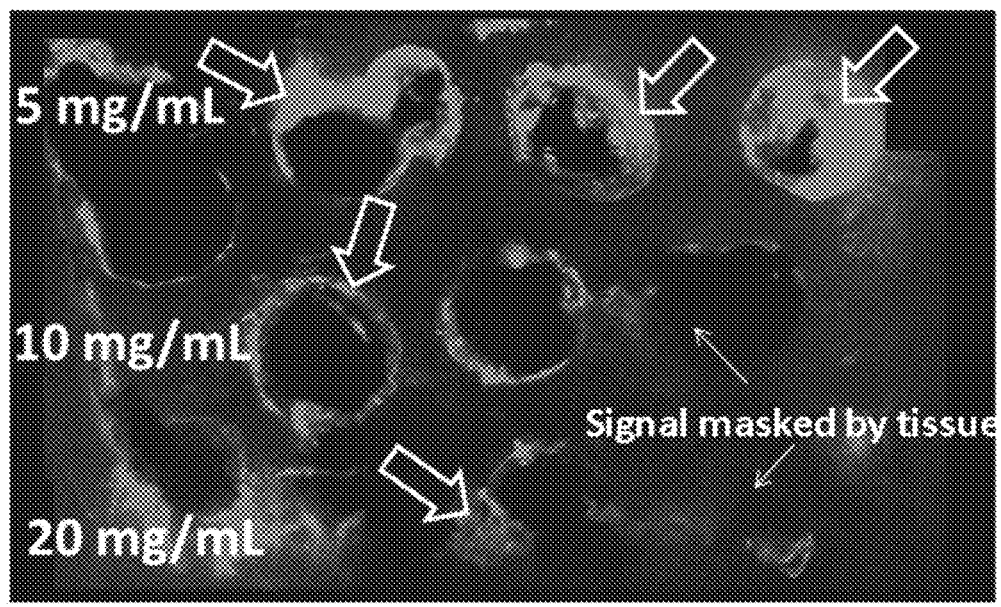
Figure 8:
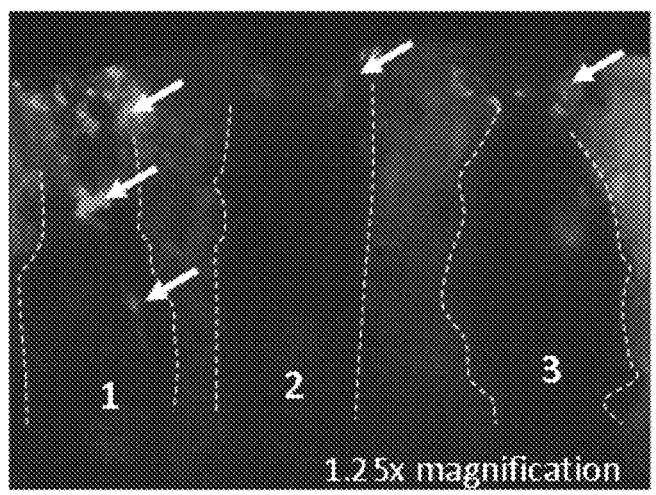
Figure 8:
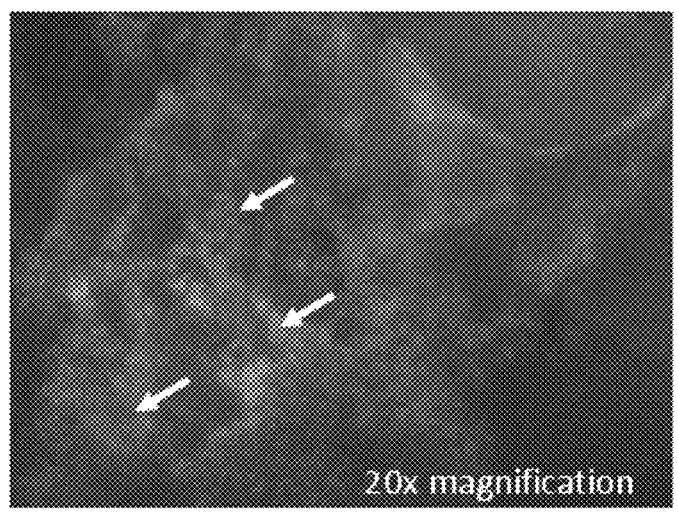
Figure 9:
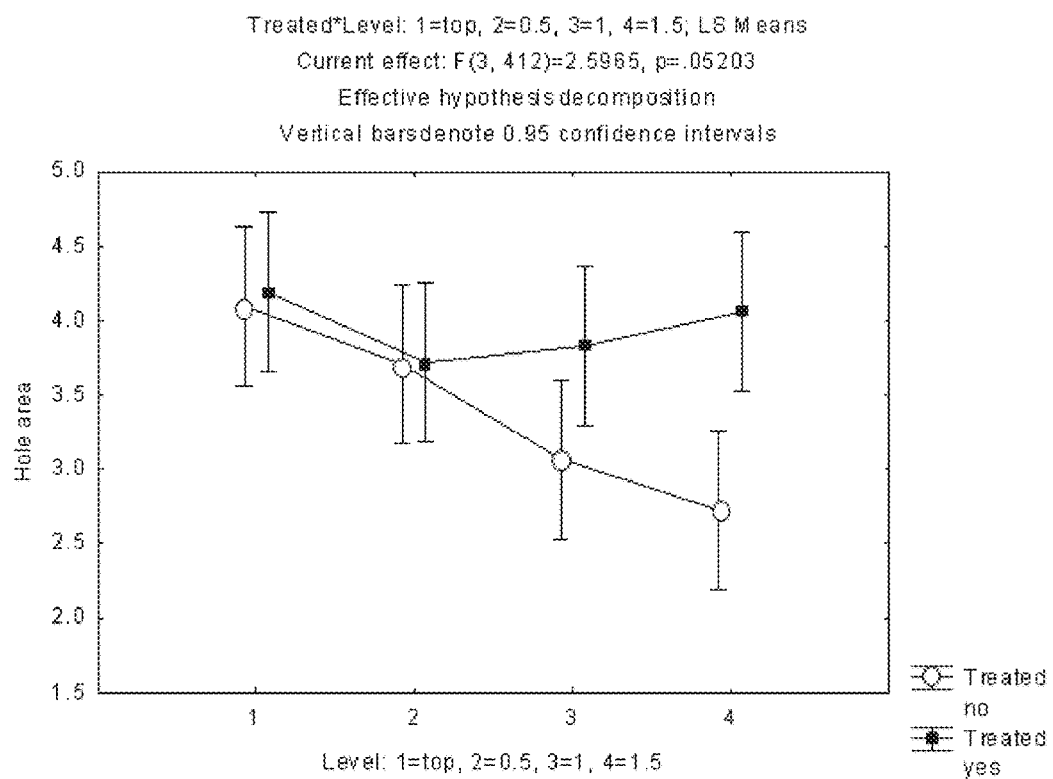
FIG. 9 contains 2 charts showing implant-induced bone remodeling and repair, at 3 and 9 months post-operative. The data show micro-computed tomography measures of the average residual microdrill hole cross-sectional area at different depths from the top of the drill hole, at 1 day, 3 months, and 9 months post-operative for drilled defects (control) versus drilled defects treated with in situ-rehydrating chitosan scaffold (formulations #29, #33, and #34). (9A) shows depth-dependent drill hole cross-sectional area at 3 months post-operative and (9B) shows micro-CT measures of residual bone hole area near the top of the drill hole over time. Microdrill holes at day 1 had a uniform cross-sectional area of $2.0 \pm 0.5$ mm$^2$ (9B). The data show that treated and untreated holes had some bone remodeling near the top of the drill hole, because the average hole diameter at 3 months is 4 mm$^2$ (see 9A, level 1, and 9B, $p<0.0001$, 3 months versus day 1). Treated holes showed a greater cross-sectional area deeper in the microdrill holes compared to drill-only defects ($p=0.052$, 9A) reflecting bone remodeling which permits more cell migration from the deeper marrow into the microdrill hole. A more complete bone hole repair was found at 9 months in treated versus drill-only defects ($p=0.03$, 9B).
Figure 9:
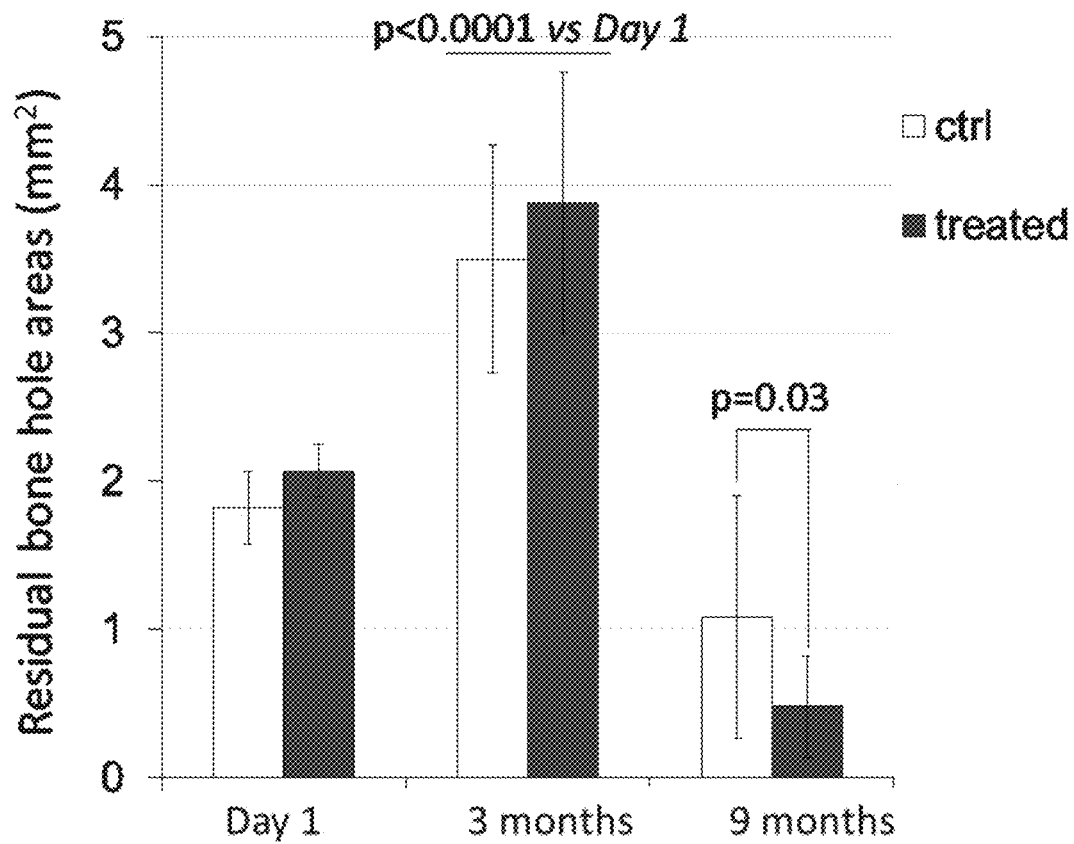
Figure 10:
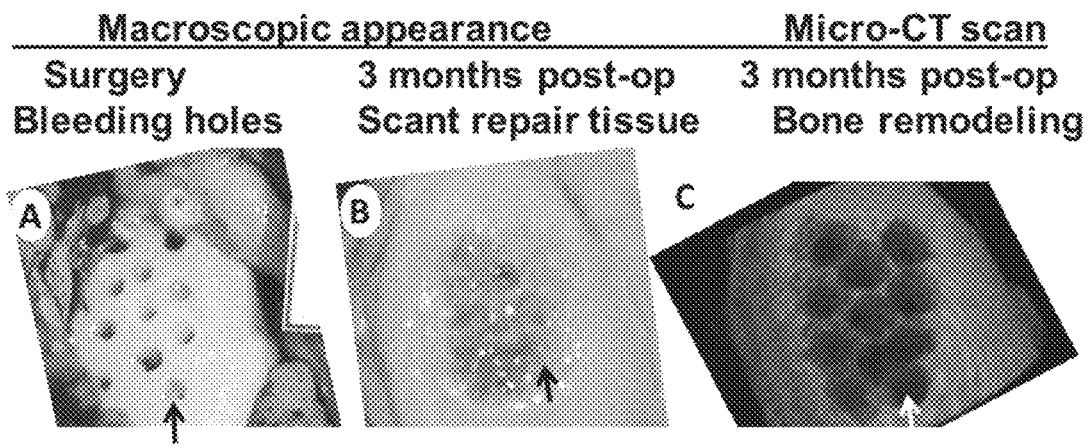
FIG. 10 shows macroscopic and histological cartilage repair at 3 months post-operative in an aged sheep model where a 10×10 mm full thickness cartilage defects were created in each medial femoral condyle and treated with 11 microdrill holes then further treated in one knee with sterile lyophilized chitosan (formulations #29, #33, and #34). In the example sheep repair shown in (10A-10C) and (10D-10F), one knee condyle defect was drilled with no further treatment (10A) and the contralateral cartilage defect was drilled and treated with chitosan scaffold (10D). At 3 months post-operative, drill-only cartilage defects contained almost no soft repair tissue (10B, macroscopic, and 10C corresponding micro-CT scan showing residual bone holes). Drill holes treated with in situ rehydrating chitosan scaffold show a dark repair tissue hue in the drill hole representing red angiogenic granulation tissue (10E, arrows pointing to holes treated by 10 mg/mL and 5 mg/mL implant), as well as some cartilage repair tissue (10E, arrows pointing to holes treated with 20 mg/mL implant), and a more porous bone structure surrounding the drill hole edges (10F, corresponding micro-CT scan of healing bone holes). This scaffold-induced bone remodeling is a desired repair response in "marrow stimulation" therapies. (10G & 10H) show histology of 3 month callus and granulation repair tissues resulting from microdrilling alone, compared to highly vascularized granulation tissue near the synovial cavity, and evidence of woven bone repair below in drill holes treated with freeze-dried chitosan implant (5, 10, or 20 mg/mL, 80 kDa, pH 2.5).
Figure 10:
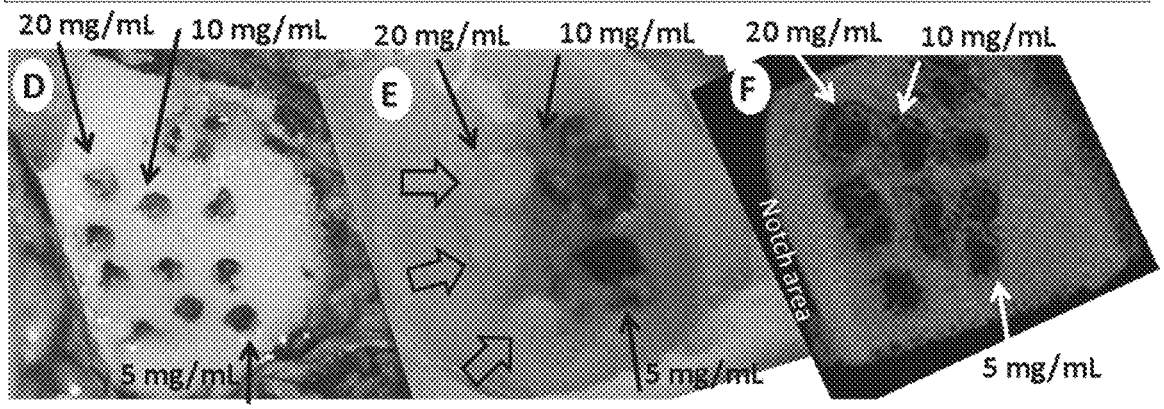
Figure 10:
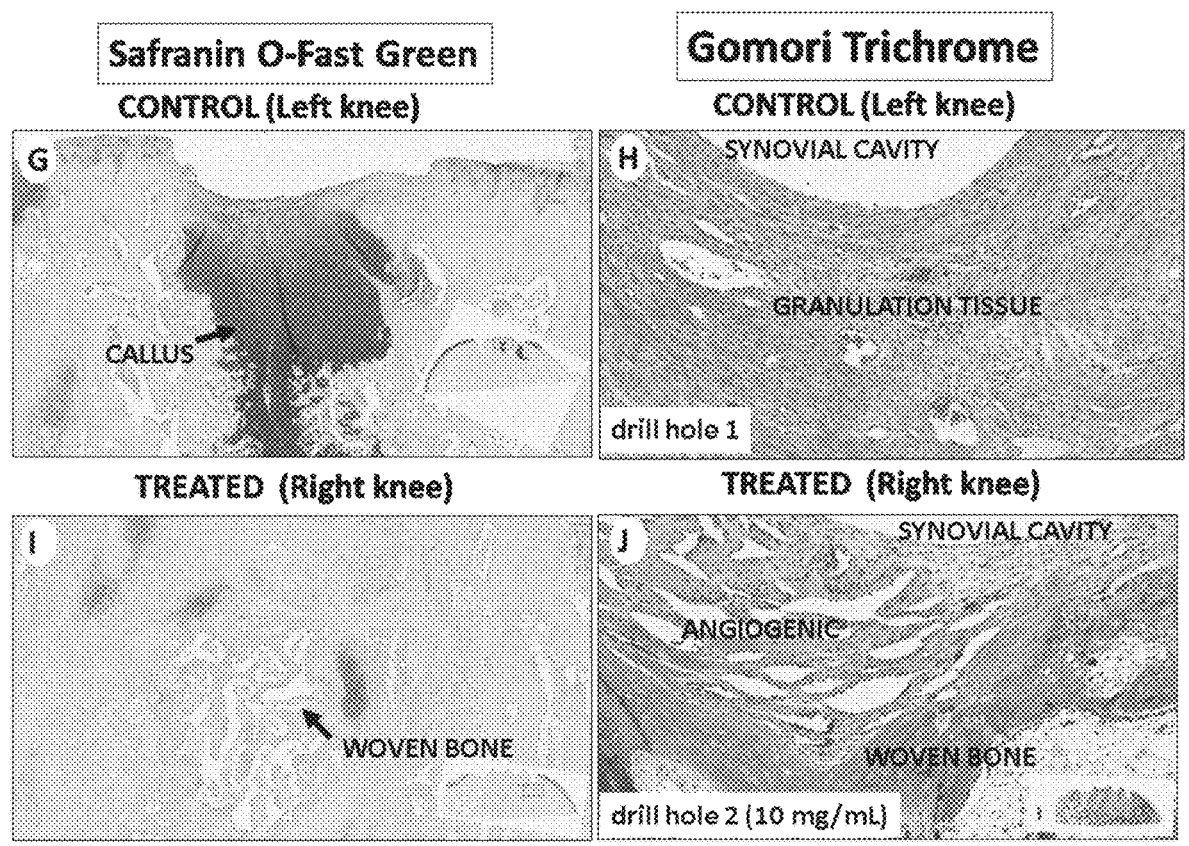
Figure 11:
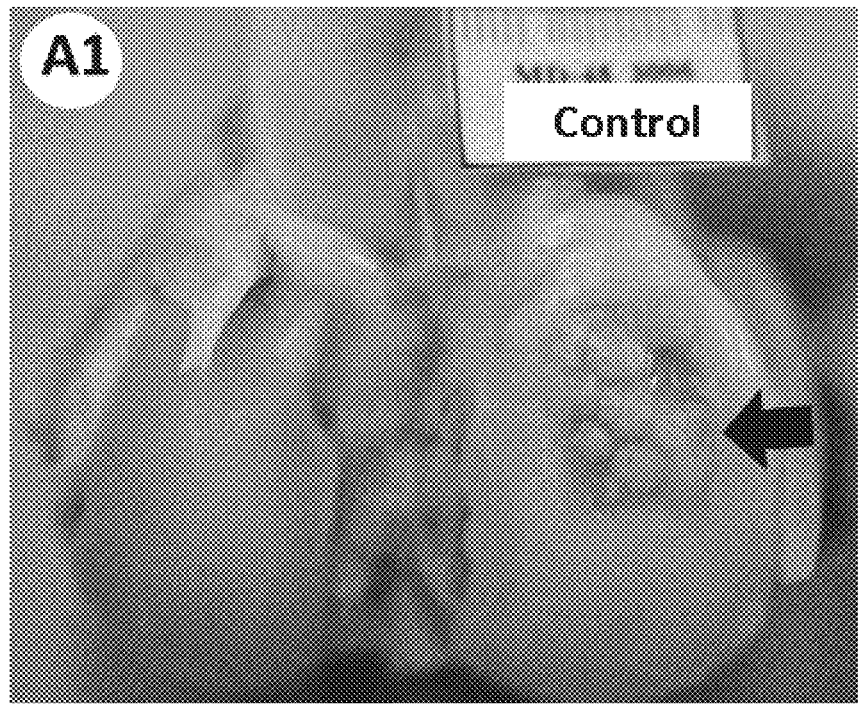
FIG. 11 shows greater cartilage resurfacing 9 months post-operative in drill holes treated with lyophilized chitosan scaffold compared to drilling-only in a large animal model. Treated sheep defects show better soft tissue resurfacing of the cartilage defect and less exposed bone than drill-only contralateral control defects at 9 months post-operative.
Figure 11:
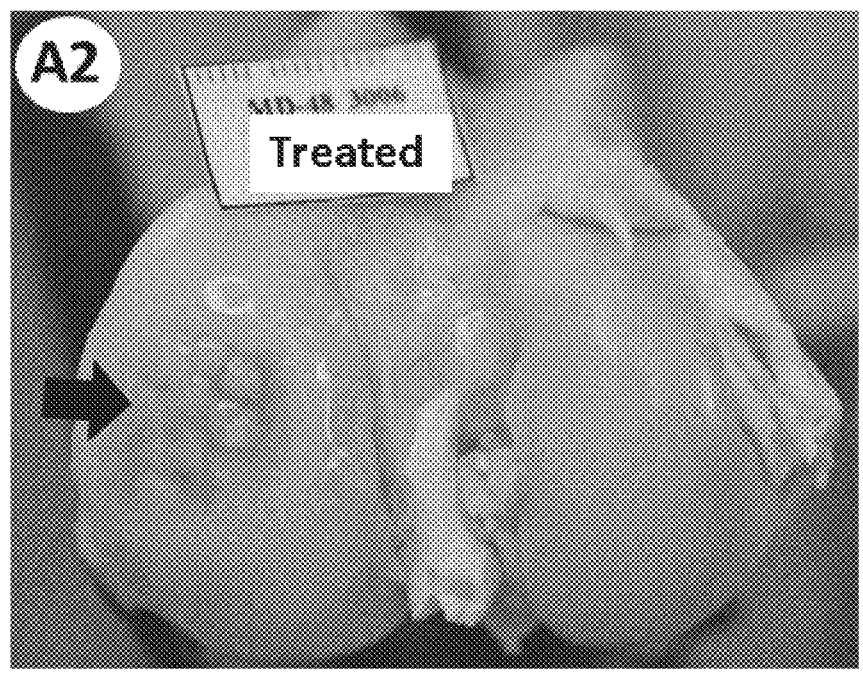
Figure 11:
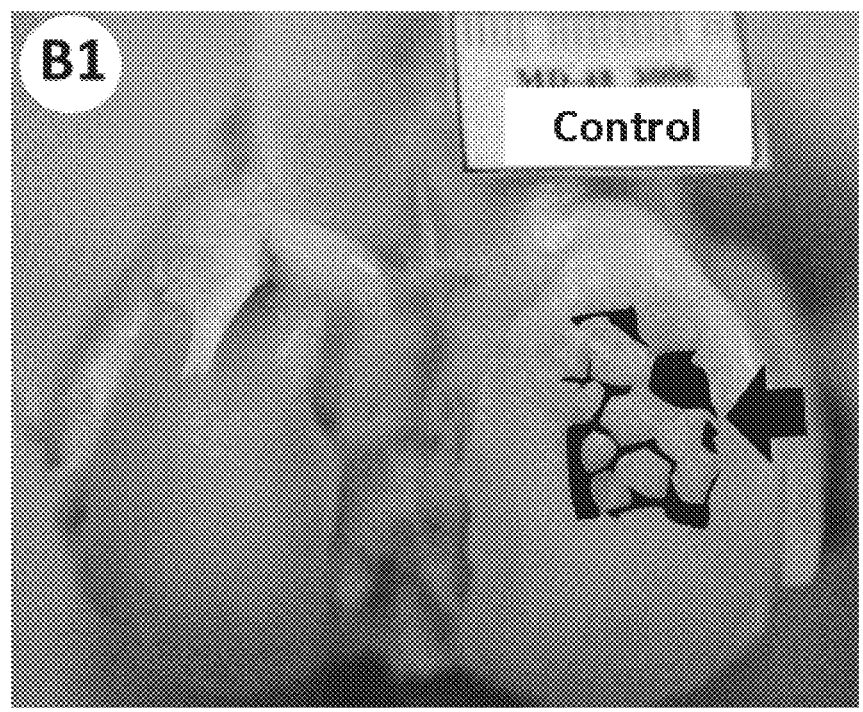
Figure 11:
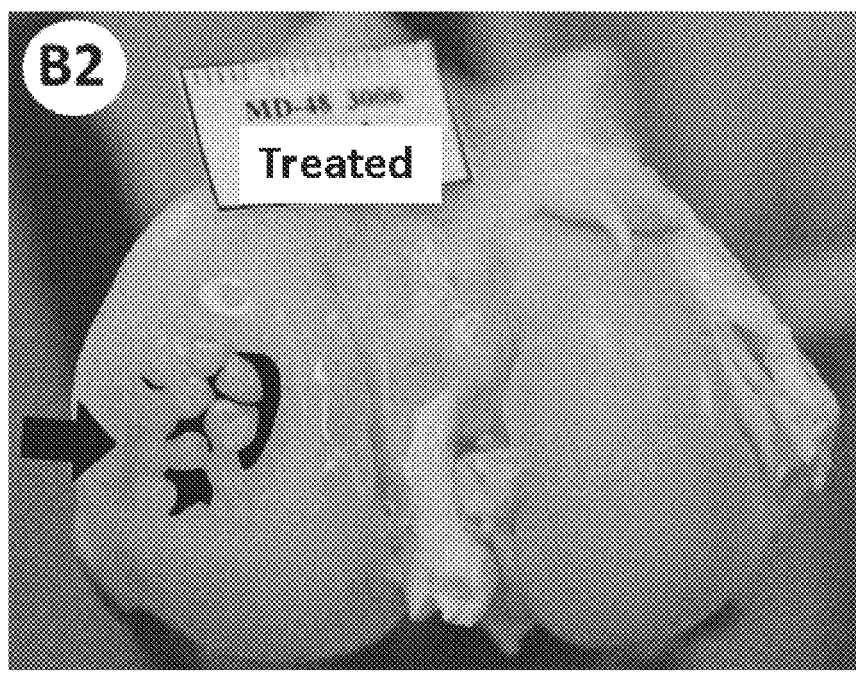
Figure 11:
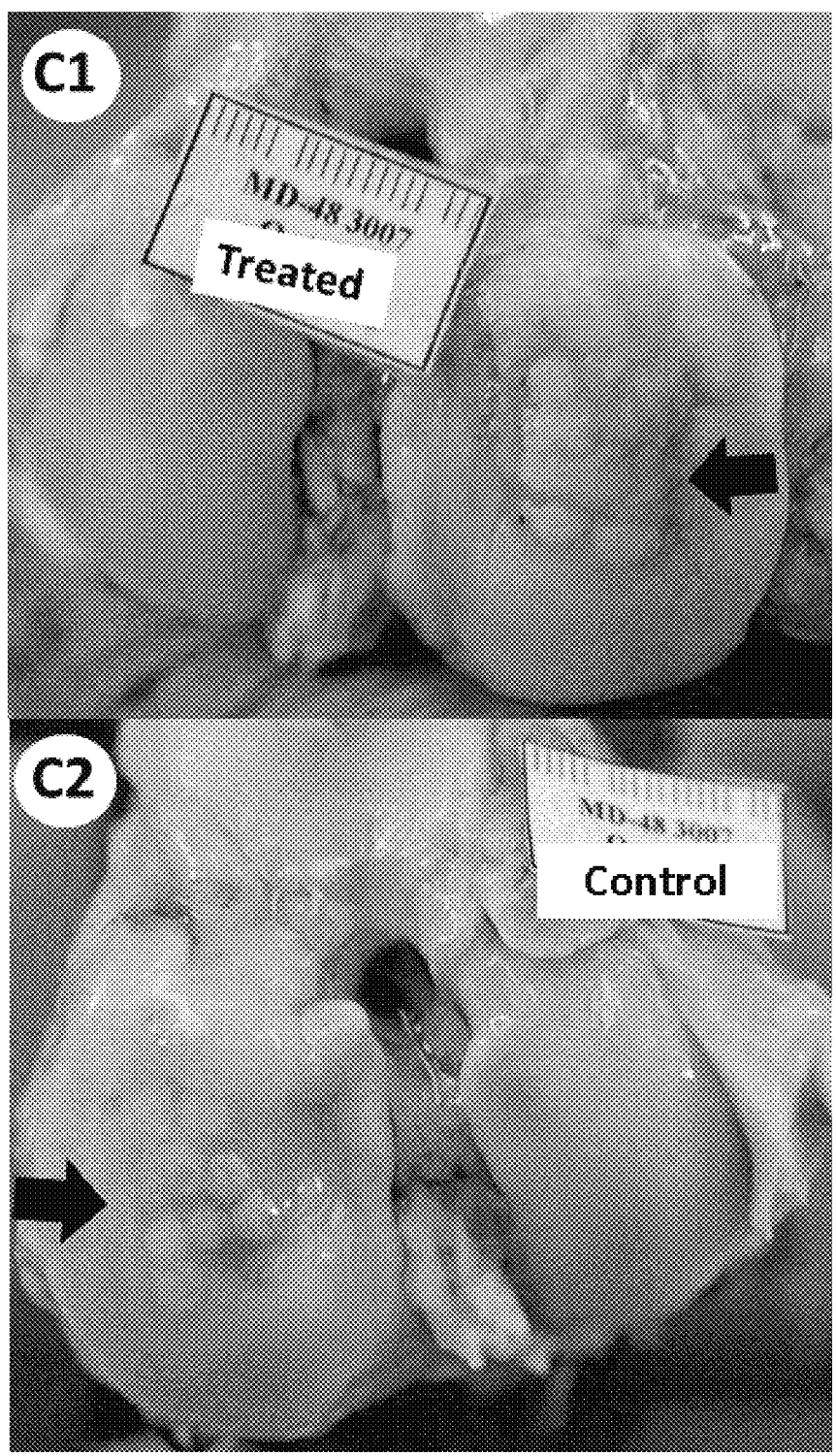
Figure 11:
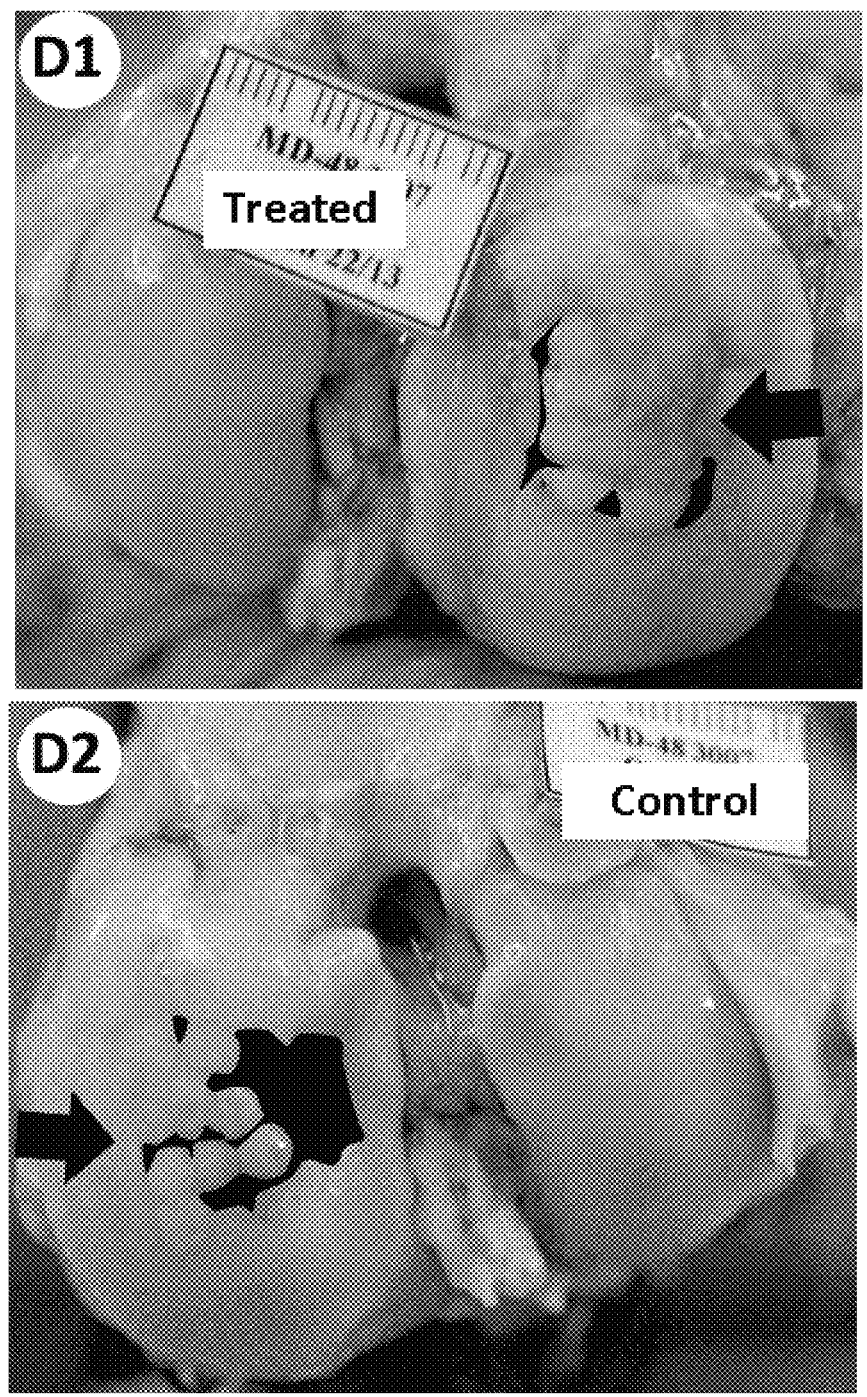
Figure 11:
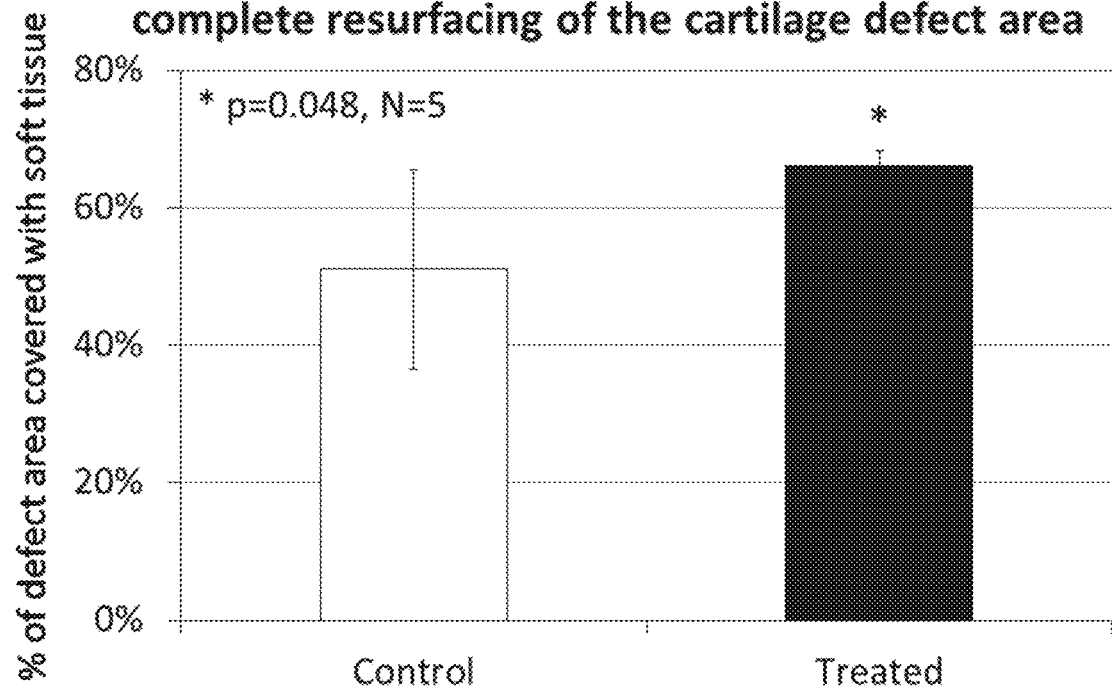
Figure 12:
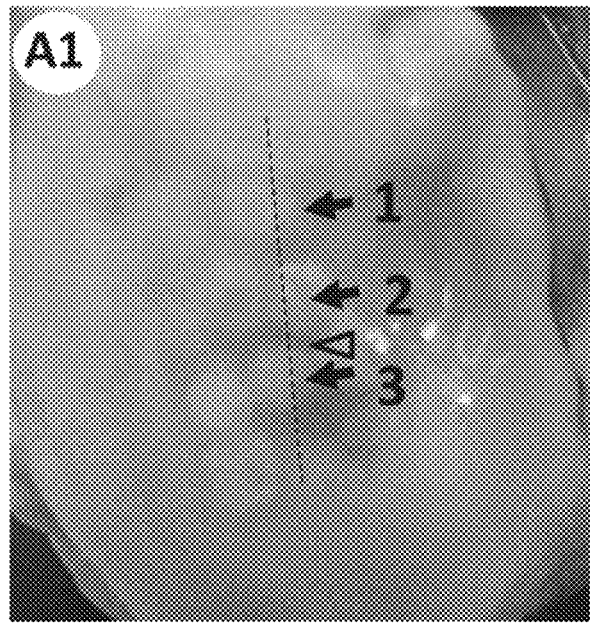
FIG. 12 shows example macroscopic appearance and corresponding histology of repair tissues formed at 9 months post-surgery, and demonstrates by quantitative histomorphometry of histological sections that a superior resurfacing is induced by microdrilling and freeze-dried chitosan implant compared to microdrilling alone. (12A1 and 12B1) show repair tissues formed a 9 months in the same sheep, where 1 knee cartilage defect was drilled (12A1) and the contralateral knee cartilage defect was drilled and treated with in situ lyophilized implant (formulations #29, #33, and #34, 12B1). Numbers 1, 2, and 3 refer to distinct drill holes analyzed in the histology section collected along the dotted line in (12A1 and 12B1). (12A2-12A3 and 12B2-12B3) show less exposed bone in the treated defect (12B2, 12B3) compared to the control defect (12A2, 12A3). (12A4 and 12B4) show that in this sheep, both control and treated microdrill holes were repaired by hyaline-like cartilage tissue. (12C) shows quantitative histomorphometry measures of defect resurfacing and that treated defects contain more soft integrated cartilage repair tissue and less exposed bone compared to control microdrill defects (N=5 defects with N=3 sections analyzed per defect).
Figure 12:
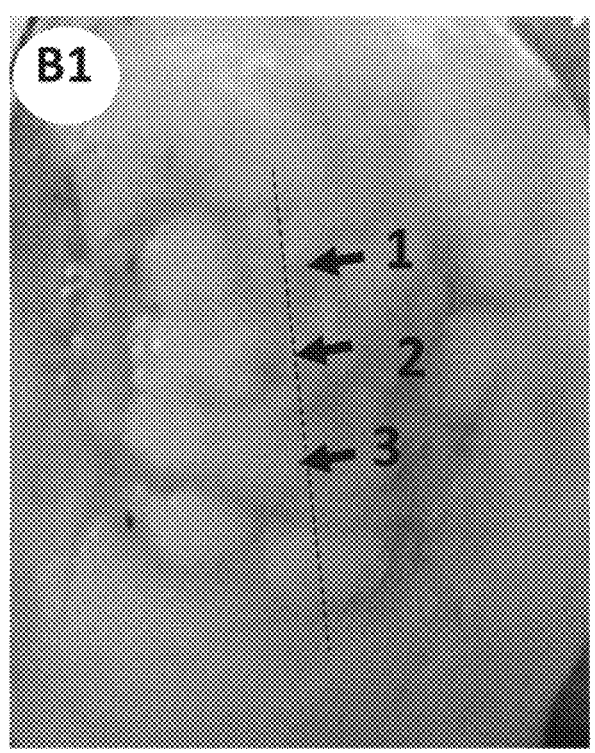
Figure 12:
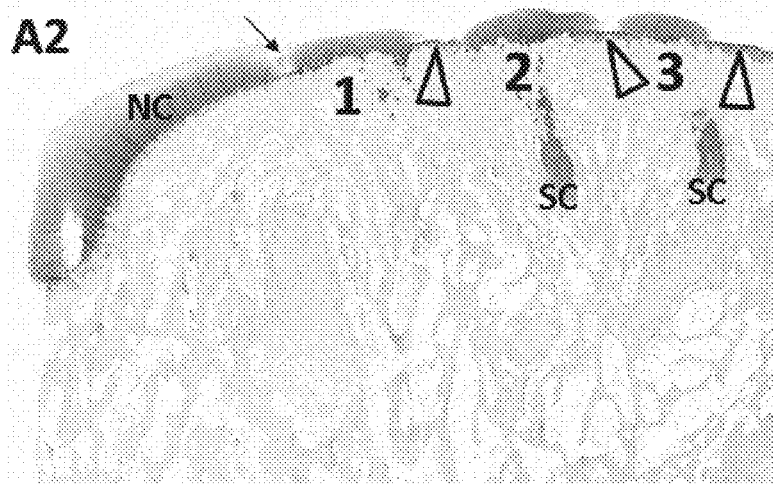
Figure 12:
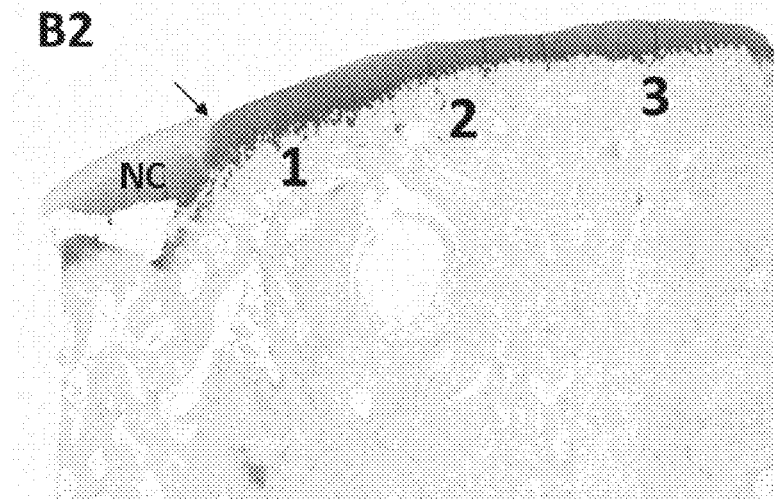
Figure 12:
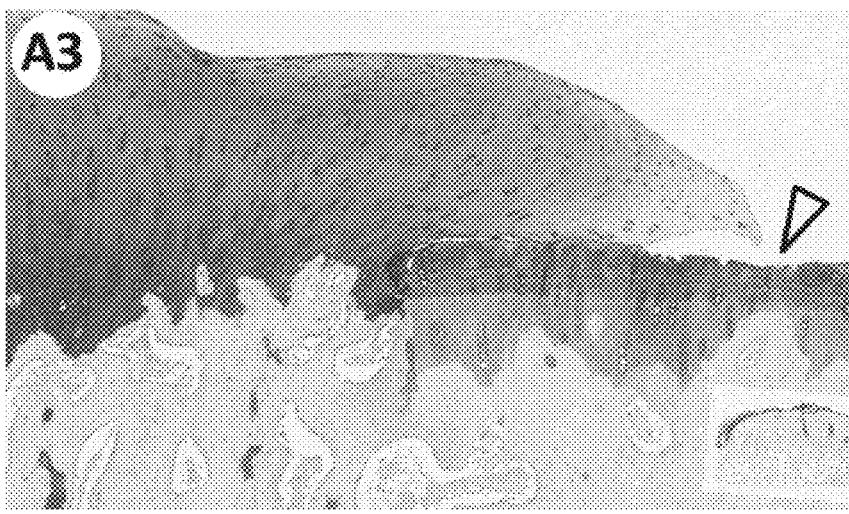
Figure 12:
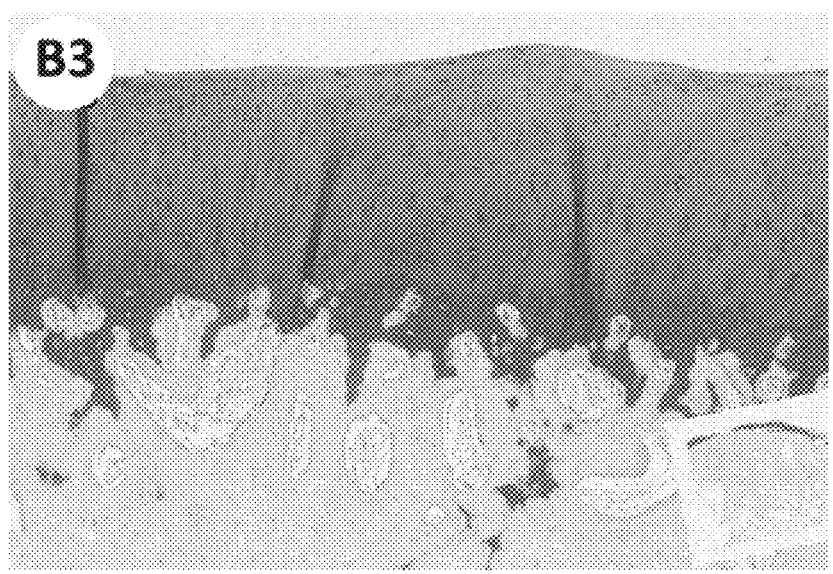
Figure 12:
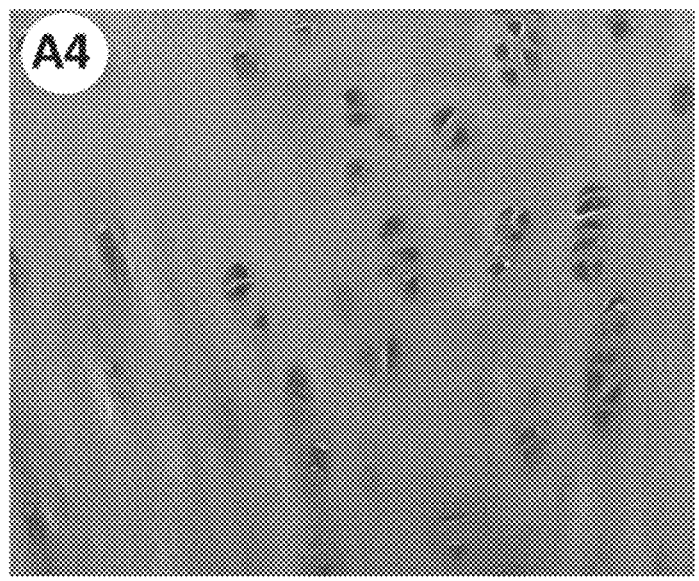
Figure 12:
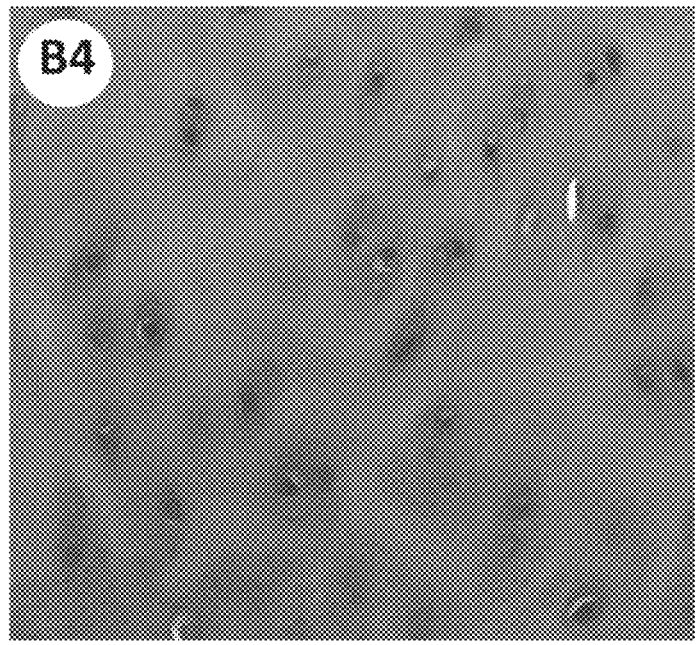
Figure 12:
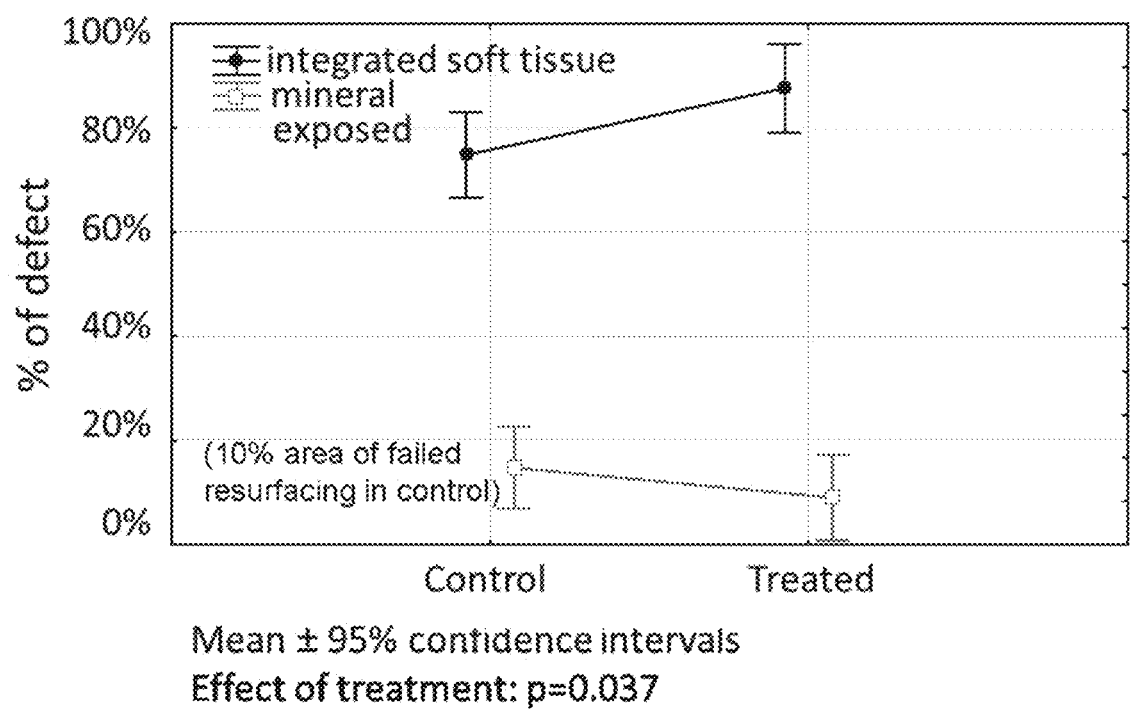

Results: Handling properties were found to be superior for 10 and 20 mg/m L freeze-dried scaffolds compared to 5 mg/mL chitosan scaffold as they were easily cored with a biopsy punch and retained a cylindrical shape. The 5 mg/mL scaffold was difficult to core with a biopsy punch and more difficult to implant in the bleeding osteochondral defect. Day 1 fluorescence images of treated drill holes show implant retention at day 1 for all 3 formulations, mainly at the edges of the holes (FIG. 8, 8B). Note that the blood coagulum that fills the holes at day 1 also contains red blood cells which can block fluorescence. At day 1 post-operative, the initial drill holes were analyzed for dimensions by micro-computed tomography and found to be 4±1.2 mm deep and 2±0.5 mm$^2$ in cross-sectional area (N=17 drill holes measured). After 3 months of repair, bone holes in all defects are slightly deeper, 5.1±1.8 mm (control) and 5.7±1.8 mm (treated). Treated drill holes showed evidence of "wound bloom", or early bone remodeling (i.e., woven bone resorption and repair), as shown by larger drill hole cross-sectional area below the subchondral bone plate compared to initial drill holes, along with more woven bone repair deeper in the treated residual bone holes compared to control drill holes (FIGS. 9A and 10I). Some treated drill holes were resurfaced with cartilage repair tissue at 3 months post-operative (FIG. 10E, 20 mg/mL chitosan-treated holes), but most treated drill holes at 3 months contained angiogenic granulation tissue and woven repair bone deeper in the 3 holes (FIG. 10H-I). At 9 months of repair, more tissue resurfaced the full-thickness cartilage defects treated by microdrilling and implant compared to drill-only controls (FIG. 11A-11E) and the repair tissues were mainly hyaline-like cartilage (FIG. 12A-12C).

Formulations targeted for therapeutic activity in human joints may show therapeutic effects using formulations covering those that were shown here to be effective in rabbit and sheep cartilage repair models. Formulations include a biodegradable chitosan (80% DDA, molecular weight 10 to 150 kDa) prepared as a solution at pH 2.5, 20 mg/mL and 45 to 68 mOsm, or 10 mg/mL and 25 mOsm or 5 mg/mL and 10 mOsm. The formulation may be adjusted to permit an in vivo clearance rate that is optimal for meniscal repair, rotator cuff repair, bone fracture repair, or other connective tissue repair, depending on the size of the lesion, and the physiological rate of granulation tissue formation and subsequent connective tissue formation. The formulation may also be adjusted to promote angiogenesis with only minor bone remodeling for applications involving tendon insertion site repair, and sinus bone augmentation procedures.

The scope of the claims should not be limited by preferred embodiments set forth in the examples, but should be given the broadest interpretation consistent with the description as a whole.

The invention claimed is:

1. A lyophilized mechanically rigid, 3-dimensional solid macroscopically visible scaffold intra-articular implant composition comprising at least one polysaccharide selected from the group consisting of chitosan, dextran and combinations thereof, wherein said mechanically rigid, 3-dimensional solid, macroscopically visible scaffold intra-articular implant has a solid state capable of being formed into a desired shape, and a microparticle dispersion state when said mechanically rigid, 3-dimensional solid scaffold intra-articular implant is contacted with at least one of a neutral aqueous solution, blood, blood derived fluid and combinations thereof; wherein the at least one polysaccharide contains free amine groups and has a protonation level between 70% and 100% protonation of said free amine groups resulting in controlled rehydration of said mechanically rigid, 3-dimensional solid macroscopically visible scaffold intra-articular implant in a time interval between 1 and 60 minutes, said mechanically rigid, 3-dimensional solid macroscopically visible scaffold intra-articular implant contacted with said at least one of a neutral aqueous solution, blood, blood derived fluid and combinations thereof exhibiting at least one of the following:
    i) stimulates tissue remodeling;
    ii) stimulates anabolic wound repair;
    iii) stabilizes a clot, a fibrin clot, blood clot or combination thereof;
    iv) stimulates neutrophil chemotaxis;
    v) stimulates macrophage chemotaxis;
    vi) stimulates angiogenesis;
    vii) stimulates mesenchymal cell chemotaxis;
    viii) suppresses fibrosis;
    ix) stimulates osteoclast formation and bone resorption;
    x) stimulates woven bone repair; and combinations thereof.

2. The lyophilized mechanically rigid, 3-dimensional solid macroscopically visible scaffold intra-articular implant composition of claim 1further comprising chitosan oligomers, monomeric glucosamine, N-acetyl glucosamine, hydrochloric acid, lactic acid, acetic acid and combinations thereof.

3. The lyophilized mechanically rigid, 3-dimensional solid macroscopically visible scaffold intra-articular implant composition of claim 1 wherein the chitosan has a molecular weight from about 5,000 Da to about 400,000 Da.

4. A lyophilized mechanically rigid, 3-dimensional solid macroscopically visible scaffold intra-articular implant composition comprising chitosan wherein said lyophilized mechanically rigid, 3-dimensional solid macroscopically visible scaffold intra-articular implant is solid and capable of being formed into a desired shape, and a microparticle dispersion when said scaffold is contacted with at least one of a neutral aqueous solution, blood, blood derived fluid and combinations thereof; wherein the chitosan contains free amine groups and has a protonation level between 70% and 100% protonation of said free amine groups resulting in controlled rehydration of said scaffold in a time interval between 1 and 60 minutes, said lyophilized mechanically rigid, 3-dimensional solid macroscopically visible scaffold intra-articular implant contacted with said least one of a neutral aqueous solution, blood, blood derived fluid and combinations thereof:
  i) stimulates tissue remodeling;
  ii) stimulates anabolic wound repair;
  iii) stabilizes a clot, a fibrin clot, blood clot or combination thereof;
  iv) stimulates neutrophil chemotaxis;
  v) stimulates macrophage chemotaxis;
  vi) stimulates angiogenesis;
  vii) stimulates mesenchymal cell chemotaxis;
  viii) suppresses fibrosis;
  ix) stimulates osteoclast formation and bone resorption;
  x) stimulates woven bone repair; and combinations thereof.

5. The lyophilized mechanically rigid, 3-dimensional solid macroscopically visible scaffold intra-articular implant composition of claim 4 wherein the chitosan has a molecular weight from about 5,000 Da to about 400,000 Da.

6. The lyophilized mechanically rigid, 3-dimensional solid macroscopically visible scaffold intra-articular implant composition of claim 4 further comprising chitosan oligomers, monomeric glucosamine, N-acetyl glucosamine, hydrochloric acid, lactic acid, acetic acid and combinations thereof.

7. The lyophilized mechanically rigid, 3-dimensional solid macroscopically visible scaffold intra-articular implant composition of claim 1 further comprising at least one of a biological protein or lipid which stimulates acute innate immune would repair responses.

8. The lyophilized mechanically rigid, 3-dimensional solid macroscopically visible scaffold intra-articular implant composition of claim 7 further comprising at least one of the following:
  i) a cationic amphiphilic anti-microbial peptide;
  ii) a biomimetic peptide that activates cell migration; and
  iii) a polypeptide or subfragment of: SDF-1/CXCL 12, chemokines, CXCL 1010/IP-10, IL-1 receptor antagonist, a bioactive lipid.

9. The lyophilized mechanically rigid, 3-dimensional solid macroscopically visible scaffold intra-articular implant composition of claim 8 further comprising a factor that activates neutrophil chemotaxis without inducing degranulation.

10. The lyophilized mechanically rigid, 3-dimensional solid macroscopically visible scaffold intra-articular implant composition of claim 8 wherein the bioactive lipid is selected from LTB4, and the biological protein is selected from the group consisting of G-CSF, GM-CSF, M-CSF, interferon beta, interferon alpha, IL-4, IL-14, IL-10 and combinations thereof.

11. The lyophilized mechanically rigid, 3-dimensional solid macroscopically visible scaffold intra-articular implant composition of claim 1 further comprising at least one biological therapeutic factor that stimulates angiogenesis.

12. The lyophilized mechanically rigid, 3-dimensional solid macroscopically visible scaffold intra-articular implant composition of claim 11 wherein the at least one biological therapeutic factor that stimulates angiogenesis is selected from the group consisting of recombinant factor VIIa (rhFVIIa), thrombin, Tissue Factor, VEGF, tryptase, MMP-13, IL-8, MCP-1 and combinations thereof.

13. The lyophilized mechanically rigid, 3-dimensional solid macroscopically visible scaffold intra-articular implant composition of claim 1 further comprising a mineral selected from the group consisting of calcium carbonate, calcium phosphate, polytriphosphate, hydroxyapatite and combinations thereof.

14. The lyophilized mechanically rigid, 3-dimensional solid macroscopically visible scaffold intra-articular implant composition of claim 9 wherein the factor is selected from the group consisting of LTB4, G-CSF, GM-CSF, M-CSF, interferon beta, interferon alpha, IL-4, IL-14, IL-10 and combinations thereof.

15. The lyophilized mechanically rigid, 3-dimensional solid macroscopically visible scaffold intra-articular implant composition of claim 1 wherein the composition is a rigid 3-dimensional structure maintaining structural integrity prior to contact with said at least one of a neutral aqueous solution, blood, blood derived fluid and combinations thereof.

16. The lyophilized mechanically rigid, 3-dimensional solid macroscopically visible scaffold intra-articular implant composition of claim 4 wherein the composition is a rigid 3-dimensional structure maintaining structural integrity prior to contact with said at least one of a neutral aqueous solution, blood, blood derived fluid and combinations thereof.

17. The lyophilized mechanically rigid, 3-dimensional solid macroscopically visible scaffold intra-articular implant composition of claim 1 wherein the composition is shaped with a biopsy punch and a scalpel in the shape of a cone or cylinder prior to contact with said at least one of a neutral aqueous solution, blood, blood derived fluid and combinations thereof.

18. The lyophilized mechanically rigid, 3-dimensional solid macroscopically visible scaffold intra-articular implant composition of claim 4 wherein the composition is shaped with a biopsy punch and a scalpel in the shape of a cone or cylinder prior to contact with said at least one of a neutral aqueous solution, blood, blood derived fluid and combinations thereof.

19. The lyophilized mechanically rigid, 3-dimensional solid macroscopically visible scaffold intra-articular implant composition of claim 1 or 4, wherein the composition contacted with said at least one of a neutral aqueous solution, blood, blood derived fluid and combinations thereof:

a) loses mechanical integrity as a microparticle dispersion;

between 1 and 60 minutes of contact with said at least one of a neutral aqueous solution, blood, blood derived fluid and combinations thereof.

20. The lyophilized mechanically rigid, 3-dimensional solid macroscopically visible scaffold intra-articular implant composition of claim 1 or 4, wherein the composition contacted with said at least one of a neutral aqueous solution, blood, blood derived fluid and combinations thereof:

a) loses said rigid 3-dimensional scaffold solid structure as a microparticle dispersion;

between 1 and 60 minutes of contact with said at least one of a neutral aqueous solution, blood, blood derived fluid and combinations thereof.

* * * * *